(12) United States Patent
Ciriello et al.

(10) Patent No.: US 12,016,653 B2
(45) Date of Patent: Jun. 25, 2024

(54) OPTICAL COHERENCE TOMOGRAPHY SCANNING SYSTEM AND METHODS

(71) Applicant: Cyberdontics (USA), Inc., Boston, MA (US)

(72) Inventors: Christopher John Ciriello, Boston, MA (US); Wei Kang, Newton Center, MA (US); Phillip Getto, Wellesley, MA (US); Angela Zhang, Stow, MA (US); Justin LaRue, Cambridge, MA (US); Victor Grinberg, Waltham, MA (US)

(73) Assignee: Perceptive Technologies, Inc., Boston, MA (US)

( * ) Notice: Subject to any disclaimer, the term of this patent is extended or adjusted under 35 U.S.C. 154(b) by 0 days.

(21) Appl. No.: 18/464,014

(22) Filed: Sep. 8, 2023

(65) Prior Publication Data

US 2024/0081650 A1  Mar. 14, 2024

Related U.S. Application Data

(60) Provisional application No. 63/499,210, filed on Apr. 28, 2023, provisional application No. 63/383,858, (Continued)

(51) Int. Cl.
*A61B 5/00* (2006.01)

(52) U.S. Cl.
CPC .......... *A61B 5/0066* (2013.01); *A61B 5/0088* (2013.01)

(58) Field of Classification Search
CPC .............................. A61B 5/0066; A61B 5/0088
See application file for complete search history.

(56) References Cited

U.S. PATENT DOCUMENTS 5,343,391 A   8/1994  Mushabac
6,802,713 B1  10/2004 Chishti et al.
(Continued)

FOREIGN PATENT DOCUMENTS

DE    10145104 A1   1/2003
EP    2459115 A2    6/2012
(Continued)

OTHER PUBLICATIONS

Fried et al.: Ablation of Dental Hard Tissues with a Microsecond Pulsed Carbon Dioxide Laser Operating at 9.3-μm with an Integrated Scanner. Proc SPIE Int Soc Opt Eng. 6843:16 pages (2008).
(Continued)

*Primary Examiner* — Jonathan Cwern
(74) *Attorney, Agent, or Firm* — George Jakobsche Patent Counsel PLLC

(57) ABSTRACT

An optical coherence tomography scanning system traverses its respective scan pattern quickly, typically completing an entire two-dimensional frame faster than a conventional raster scanner completes one raster line segment. To traverse the scan pattern quickly, the system takes fewer A-scans per length of scan pattern than a conventional OCT scanner. To compensate for the sparsity of the sample points along the respective scan line segments, and for gaps between respective line segments of the trajectory, the system acquires and combines several partially overlapping frames for each study.

25 Claims, 28 Drawing Sheets

Related U.S. Application Data filed on Nov. 15, 2022, provisional application No. 63/380,161, filed on Oct. 19, 2022, provisional application No. 63/378,482, filed on Oct. 5, 2022, provisional application No. 63/410,155, filed on Sep. 26, 2022, provisional application No. 63/374,991, filed on Sep. 8, 2022.

(56) References Cited

U.S. PATENT DOCUMENTS

| | | | |
|---|---|---|---|
| 6,845,190 B1 | 1/2005 | Smithwick et al. | |
| 8,251,984 B2 | 8/2012 | Monty | |
| 9,408,673 B2 | 8/2016 | Monty | |
| 9,622,833 B2 | 4/2017 | Monty | |
| 9,675,419 B2 | 6/2017 | Akeel et al. | |
| 9,788,915 B2 | 10/2017 | Monty et al. | |
| 10,016,242 B2 | 7/2018 | Salcedo et al. | |
| 11,497,402 B2 | 11/2022 | Fan et al. | |
| 2003/0135092 A1 | 7/2003 | Cline et al. | |
| 2006/0127848 A1 | 6/2006 | Sogo et al. | |
| 2007/0115481 A1 | 5/2007 | Toth et al. | |
| 2007/0134615 A1* | 6/2007 | Lovely | A61B 1/063 382/128 |
| 2009/0154768 A1 | 6/2009 | Bell | |
| 2009/0186318 A1 | 7/2009 | Assa et al. | |
| 2010/0172567 A1* | 7/2010 | Prokoski | A61B 5/0064 348/47 |
| 2011/0313825 A1 | 12/2011 | Wilhelm et al. | |
| 2012/0113280 A1 | 5/2012 | Stupak et al. | |
| 2013/0010079 A1 | 1/2013 | Zhang et al. | |
| 2013/0021447 A1 | 1/2013 | Brisedoux et al. | |
| 2013/0322719 A1 | 12/2013 | Dekel et al. | |
| 2015/0176775 A1 | 6/2015 | Gu et al. | |
| 2015/0320320 A1 | 11/2015 | Kopelman et al. | |
| 2015/0365604 A1 | 12/2015 | Griffith et al. | |
| 2016/0248994 A1 | 8/2016 | Liu | |
| 2016/0338803 A1 | 11/2016 | Pesach | |
| 2018/0028065 A1* | 2/2018 | Elbaz | A61B 5/7435 |
| 2019/0029524 A1 | 1/2019 | Kopelman et al. | |
| 2019/0038367 A1 | 2/2019 | Ciriello et al. | |
| 2019/0049232 A1* | 2/2019 | Vakoc | G01B 9/02091 |
| 2019/0076026 A1 | 3/2019 | Elbaz et al. | |
| 2019/0281272 A1* | 9/2019 | Babayoff | G01J 3/10 |
| 2020/0000551 A1 | 1/2020 | Li et al. | |
| 2020/0163729 A1 | 5/2020 | Ciriello et al. | |
| 2020/0315754 A1 | 10/2020 | Ciriello et al. | |
| 2020/0390518 A1 | 12/2020 | Ciriello et al. | |
| 2021/0228317 A1 | 7/2021 | Ciriello et al. | |
| 2021/0251721 A1 | 8/2021 | Ciriello et al. | |
| 2022/0087599 A1* | 3/2022 | Goldman | A61B 5/489 |
| 2022/0183789 A1 | 6/2022 | Ciriello et al. | |
| 2022/0189611 A1* | 6/2022 | Farkash | A61B 1/0684 |
| 2022/0354623 A1 | 11/2022 | Ciriello et al. | |
| 2023/0200934 A1 | 6/2023 | Ciriello et al. | |

FOREIGN PATENT DOCUMENTS

| | | |
|---|---|---|
| WO | WO-2011014802 A2 | 2/2011 |
| WO | WO-2016022347 A1 | 2/2016 |
| WO | WO-2017100828 A1 | 6/2017 |
| WO | WO-2017130060 A1 | 8/2017 |
| WO | WO-2018154485 A1 | 8/2018 |
| WO | WO-2019215511 A2 | 11/2019 |
| WO | WO-2019215512 A1 | 11/2019 |
| WO | WO-2021044218 A1 | 3/2021 |
| WO | WO-2021155045 A1 | 8/2021 |
| WO | WO-2021257708 A1 | 12/2021 |
| WO | WO-2022051516 A1 | 3/2022 |
| WO | WO-2022060800 A1 | 3/2022 |
| WO | WO-2022212507 A1 | 10/2022 |

OTHER PUBLICATIONS

Fried et al.: Frailty in older adults: evidence for a phenotype. J Gerontol A Biol Sci Med Sci.; 56(3):M146-56 (2001).

Kim et al.: Improved accuracy in periodontal pocket depth measurement using optical coherence tomography. J Periodontal Implant Sci. 47(1):13-19 (2017).

Le et al.: A non-invasive imaging and measurement using optical coherence tomography angiography for the assessment of gingiva: An in vivo study. J Biophotonics. 11(12) (2018).

PCT/IB2020/000729 International Search Report and Written Opinion dated Dec. 31, 2020.

PCT/US2021/015555 International Search Report and Written Opinion dated Apr. 14, 2021.

PCT/US2021/048893 International Search Report and Written Opinion dated Dec. 7, 2021.

PCT/US2022/022550 PCT International Search Report and Written Opinion dated Aug. 16, 2022.

PCT/US2022/022550 PCT Invitation to Pay Additional Fees dated Jun. 3, 2022.

Tsubokawa et al.: In vitro and clinical evaluation of optical coherence tomography for the detection of subgingival calculus and root cementum. J Oral Sci. 60(3):418-427 (2018).

URL https://en.wikipedia.org/wiki/Smoothness, printed Sep. 11, 2023, 9 pages.

U.S. Appl. No. 18/177,691 Office Action dated May 18, 2023.

Visuri et al.: Shear Strength of Composite Bonded to Er:YAG Laser-prepared Dentin. J Dent Res; 75(1):599-605 (1996).

Yuan et al.: An automatic tooth preparation technique: A preliminary study; Scientific Reports|6:25281|DOI: 10.1038/srep25281, pp. 1-9 (2016).

* cited by examiner

OPTICAL COHERENCE TOMOGRAPHY SCANNING SYSTEM AND METHODS

CROSS-REFERENCE TO RELATED APPLICATIONS

This application claims the benefit of U.S. Provisional Application No. 63/374,991, filed on Sep. 8, 2022, U.S. Provisional Application No. 63/410,155 filed on Sep. 26, 2022, U.S. Provisional Application No. 63/378,482, filed on Oct. 5, 2022, U.S. Provisional Application No. 63/380,161, filed on Oct. 19, 2022, U.S. Provisional Application No. 63/383,858, filed on Nov. 15, 2022, and U.S. Provisional Application No. 63/499,210, filed on Apr. 28, 2023, the content of which is incorporated herein in its entirety.

BACKGROUND

Dental caries is a common disease that affects more than 90% of American adults. Despite advances in preventive measures, dental caries continues to be a primary reason for invasive treatment to restore teeth. Over 35% of Americans do not see a dentist in any given year, and the United States Centers for Disease Control and Prevention (CDC) indicate that about 28% have untreated tooth decay. Of the patients that visit dentists, Dental Service Organizations (DSOs) indicate that patient acceptance of an ideal dental treatment plan occurs only about 30% of the time and state that the main reasons for this low acceptance rate are: cost of care, inconvenience of multiple and lengthy dental appointments, and poor case acceptance by both patients and insurance carriers.

Avoiding dentists for these reasons usually results in dental disease progression, periodontal disease, and other oral problems, e.g., lack of detection of oral cancers, which have been associated with numerous adverse medical impacts, including eating disorders, speech difficulties, poor social interactions, reduced employment potential, and an increased risk of systemic diseases, such as diabetes, cardiovascular disease, such as stroke and heart attacks, and Alzheimer's disease. Health issues resulting from poor oral health have been shown to culminate in over $45B of lost productivity in the United States and over 34M lost school hours for young adults. There is, therefore, a critical unmet need for affordable and efficient dental health care.

To address these problems and increase access to dental care, a means is needed to lower treatment costs, shorten appointments, and improve case acceptance by patients and insurers. Treatment costs can be lowered, and appointments can be shortened, by improving prevention and reducing the costs of restorative intervention. Increased early and accurate diagnosis would improve preventative care. Automation of tooth preparation or restorative treatment would shorten dentist time and decrease associated costs and appointment times.

In early stages of dental caries, loss of minerals in a tooth can be reversed when there is a sufficient supply of calcium, phosphate, and fluoride ions in the mouth. These ions help to re-mineralize the tooth. Early and accurate diagnosis of dental caries lowers dental treatment costs, as it allows for the use of non-invasive treatment methods to prevent or forestall the onset and progression of the disease. Automation of dentist labor for restorative treatment via the use of robotics lowers treatment cost and shortens appointment times for dental disease that has progressed beyond the point of re-mineralization. However, such an approach requires an improved imaging modality that offers both true tooth geometry and high sensitivity and specificity, beyond the capabilities of radiographs, to guide robots. Neither dental radiographs nor cone-beam computed tomography (CBCT) is sufficiently accurate to replace intraoral scanners (IOS) for restorative dentistry. This is evidenced by the fact that dentists must use real-time visual and tactile feedback during tooth preparation to localize and remove all tooth decay.

To improve case acceptance by patients and insurers, a more sensitive and specific imaging modality that is easy to read by both patients and insurers is needed. Today, patients are unaccustomed to interpreting two-dimensional (2D) radiographs and thus are unable to independently verify the need for care without a provider's interpretation. Three-dimensional (3D) radiographs, such as CBCT, circumvent this problem, according to DSOs, and improve overall case acceptance. Insurers rely on a variety of inputs to validate the need for care, including clinical notes and radiographs. However, radiographs have their own inherent limitations, including low sensitivity and specificity and an inability to image soft tissue and cracks in teeth. This low sensitivity and specificity of radiographs often creates discrepancies between providers and payers, resulting in patients not being covered by insurance, and discrepancies between providers, which lowers trust in the profession and, thus, case acceptance.

Optical coherence tomography (OCT) is an excellent imaging candidate technology as it offers several advantages over radiographs for dental applications. Optical coherence tomography (OCT) uses near infrared light to capture 3D images in biological tissues. Compared to X-ray and Computed Tomography, OCT uses non-ionizing radiation usually at a low power level, thus may be safer for operators and patients during operation. Exemplary advantages of OCT include fast 3D imaging, non-ionizing radiation, high dental sensitivity and specificity, and high spatial resolution (currently about 1-20 µm). However, OCT has limitations that restrict its use in dentistry, such as limited penetration depth, a small field of view (FOV) that prevents full arch imaging, a long capture time that can cause motion distortion within a single volume, and a need for complex registration to achieve surface trueness required of an intraoral scanner (IOS) or to guide automated tooth preparation surgery.

SUMMARY

The present disclosure provides improved optical coherence tomography (OCT) systems and methods. In some embodiments of the present disclosure, a tomography system is provided. The system may comprise a probe housing, an optical coherence tomography system, a moveable mirror, a motor, and a controller. The probe housing defines a window and is configured to be translated along a path proximate an anatomical item in a live patient. The path need not be straight. The anatomical item has a surface.

The optical coherence tomography system includes a sample arm and an optical detector. A portion of the sample arm extends outside the probe housing, in free space, via the window.

The moveable mirror system is disposed within the probe housing and is configured to redirect the sample arm. The motor is disposed within the probe housing and is coupled to the mirror system. The controller is configured to automatically drive the motor to repeatedly alter orientation of the mirror system about two different axes to thereby repeatedly scan the surface of the anatomic item with light of the sample arm along a trajectory according to a deterministic smooth two dimensional scan pattern.

Trajectory means relative to the housing. Thus, the trajectory does not change from scan to scan, even though different portions of the anatomical item may be scanned by successive scans. Traversal means a complete repetition of the scan pattern, although the scan pattern may not form a closed loop.

Successive means one after the other without interruption, but not necessarily including the first (traversal).

The anatomic item can have a three-dimensional surface, but the light of the sample arm is scanned in two dimensions, as viewed down the axis of the scanner, toward the item (not counting the depth scanning provided by the OCT).

Smooth functions have a unique defined first derivative (slope or gradient) at every point. Graphically, a smooth function of a single variable can be plotted as a single continuous line with no abrupt bends or breaks. In some embodiments, the scan pattern is at least C0 smooth. (See https://en.wikipedia.org/wiki/Smoothness).

Scan means one complete traversal of the two-dimensional scan pattern, although the traversal may not result in a closed loop, for example due to movement of the housing during the scan.

Each traversal of the scan pattern defines a respective two-dimensional scan area outer boundary on a respective portion of the surface of the anatomic item. Each traversal of the scan pattern defines a plurality of gaps between respective line segments of the trajectory. The gaps are unilluminated by the light during the traversal. Successive traversals of the scan pattern, in which respective scans are performed from different locations along the path, and each such scan has a respective scan area outer boundary that partially overlaps a scan area outer boundary of at least one other such scan, illuminate respective portions of at least some of the gaps defined by at least one other such traversal of the scan pattern.

For each traversal, the controller is configured to receive pixel image data from the optical detector. The pixel image data contains information about the respective portion of the surface of the anatomic item. The pixel image data of each traversal contains a first number of pixels.

For a plurality of successive traversals, in which respective scans are performed from different locations along the path, and each such scan has a respective scan area outer boundary that partially overlaps a scan area outer boundary of at least one other such scan, the controller is configured to stitch together the pixel image data of the plurality of successive traversals to thereby generate a stitched surface image having a number of pixels greater than the first number of pixels.

In any embodiment, the controller may be configured to analyze image features of the pixel image data of the plurality of successive traversals to thereby estimate respective displacements of ones of the respective scan area outer boundaries from other of the respective scan area outer boundaries.

Displacement, represented by a vector, essentially is an amount and direction by which the scan area outer boundaries (bounding boxes) of two successive scans do not overlap each other. That vector represents movement of the scanning wand between the two scans.

In any embodiment, the scan pattern may include a Lissajous figure. In any embodiment, the scan pattern may be anisotropic.

In any embodiment, the controller may be configured, for each traversal, to receive voxel subsurface data from the optical detector. The voxel subsurface data includes information about a respective subsurface portion of the anatomic item. The voxel subsurface data of each traversal contains a second number of voxels. The controller may be configured, for the plurality of successive traversals, to stitch together the voxel subsurface data of the plurality of successive traversals to thereby generate a stitched subsurface three-dimensional volume image having a number of voxels greater than the second number of voxels.

In any embodiment, the controller may be configured to use the pixel image data to detect a tooth surface (e.g., an enamel/air boundary, air/dentin boundary, air/cementum boundary, also the air/gingiva boundary, air/decay boundary, enamel/dentin boundary, dentin/pulp boundary, restoration/tooth boundary, gingiva/tooth boundary and the air/bone boundary, etc.) of the anatomical item. The controller may be configured to estimate an amount of refraction of the light at the enamel/air boundary based on a difference between a refractive index of enamel and a refractive index of air. The controller may be configured to alter coordinates of the voxel subsurface data to at least partially compensate for the refraction of the light at the enamel/air boundary.

In any embodiment, the controller may be configured to use the voxel subsurface data to detect an enamel surface of the anatomical item. The controller may be configured to use the voxel subsurface data to detect an enamel/dentin boundary within the anatomical item. The controller may be configured to estimate a thickness of the enamel between the enamel surface and the enamel/dentin boundary. The controller may be configured to estimate an amount of refraction of the light within the enamel based on (a) the thickness of the enamel and (b) a predetermined index of refraction of enamel. The controller may be configured to alter coordinates of the voxel subsurface data to at least partially compensate for the refraction of the light within the enamel.

In any embodiment, the mirror system may have a resonant frequency. The controller may be configured to drive the motor to repeatedly alter orientation of the mirror system at a frequency within 50% of the resonant frequency.

In any embodiment, the controller may be configured to drive the motor to repeatedly alter orientation of the mirror system at a frequency within 30% of the resonant frequency.

In any embodiment, the controller may be configured to drive the motor to repeatedly alter orientation of the mirror system at a frequency within 20% of the resonant frequency.

Another embodiment of the present invention provides a tomography system. The system includes a probe housing defining a window and configured to be translated along a path proximate an anatomical item in a live patient, the anatomical item having a surface. An optical coherence tomography system includes a sample arm and an optical detector, wherein a portion of the sample arm extends outside the probe housing, in free space, via the window. A moveable mirror system is disposed within the probe housing and is configured to redirect the sample arm. A motor is disposed within the probe housing and is coupled to the mirror system.

A controller is configured to automatically drive the motor to repeatedly alter orientation of the mirror system about two different axes to thereby repeatedly scan the surface of the anatomic item with light of the sample arm along a trajectory according to a deterministic two-dimensional scan pattern. Each traversal of the scan pattern defines a respective two-dimensional scan area outer boundary on a respective portion of the surface of the anatomic item. Each traversal of the scan pattern defines a plurality of gaps between respective line segments of the trajectory, wherein the gaps are unilluminated by the light during the traversal. Successive traversals of the scan pattern, in which respective scans are performed from different locations along the path, and each such scan has a respective scan area outer boundary that partially overlaps a scan area outer boundary of at least one other such scan, illuminate respective portions of at least some of the gaps defined by at least one other such traversal of the scan pattern.

For each traversal, the controller is configured to receive pixel image data from the optical detector, about the respective portion of the surface of the anatomic item, wherein the pixel image data of each traversal contains a first number of pixels. The controller is further configured, for a plurality of successive traversals, in which respective scans are performed from different locations along the path, and each such scan has a respective scan area outer boundary that partially overlaps a scan area outer boundary of at least one other such scan, to stitch together the pixel image data of the plurality of successive traversals to thereby generate a stitched surface image having a number of pixels greater than the first number of pixels.

In any embodiment, the scan pattern may include a raster.

Yet another embodiment of the present invention provides a tomography system. The system includes a probe housing defining a window and configured to be translated along a path proximate an anatomical item in a live patient. The anatomical item has a surface.

An optical coherence tomography system includes a sample arm and an optical detector, wherein a portion of the sample arm extends outside the probe housing, in free space, via the window. A moveable mirror system is disposed within the probe housing and is configured to redirect the sample arm. A motor is disposed within the probe housing and is coupled to the mirror system.

A controller configured to automatically drive the motor to repeatedly alter orientation of the mirror system about two different axes to thereby repeatedly scan the surface of the anatomic item with light of the sample arm along a trajectory according to a scan pattern that is smooth along at least 80% of the trajectory. Each traversal of the scan pattern defines a respective two-dimensional scan area outer boundary on a respective portion of the surface of the anatomic item. Each traversal of the scan pattern defines a plurality of gaps between respective line segments of the trajectory, wherein the gaps are unilluminated by the light during the traversal. Successive traversals of the scan pattern, in which respective scans are performed from different locations along the path, and each such scan has a respective scan area outer boundary that partially overlaps a scan area outer boundary of at least one other such scan, illuminate respective portions of at least some of the gaps defined by at least one other such traversal of the scan pattern.

For each traversal, the controller is configured to receive pixel image data from the optical detector, about the respective portion of the surface of the anatomic item, wherein the pixel image data of each traversal contains a first number of pixels. The controller is configured, for a plurality of successive traversals, in which respective scans are performed from different locations along the path, and each such scan has a respective scan area outer boundary that partially overlaps a scan area outer boundary of at least one other such scan, to stitch together the pixel image data of the plurality of successive traversals to thereby generate a stitched surface image having a number of pixels greater than the first number of pixels.

In any embodiment, the scan pattern may include a spiral.

In any embodiment, the mirror may include a first mirror and a second mirror. The motor may be configured to continually alter orientation of the first mirror along a first axis and to continually alter orientation of the second mirror along a second axis, different from the first axis.

In any embodiment, collectively the mirror and the motor may include a dual-axis microelectro-mechanical system.

Any embodiment may include a memory storing calibration data that characterizes per tomography system optical nonidealities. The controller may be configured to alter data received from the optical detector to at least partially compensate for the optical nonidealities.

In any appropriate embodiment, the optical nonidealities may include at least one of: lens aberration, deformation of the mirror due to being driven by the motor, and optical misalignment.

In any embodiment, the controller may be configured to drive the motor to alter the orientation of the mirror system along the two axes to thereby repeatedly scan the item along a first closed-loop two-dimensional scan trajectory and a second closed-loop two-dimensional scan trajectory, wherein the first closed-loop two-dimensional scan trajectory provides more sample points than the second closed-loop two-dimensional scan trajectory.

Any embodiment may include a motion detector mechanically coupled to the probe housing and configured to detect motion of the probe housing. The controller may be configured to automatically detect when the probe housing motion is less than a predetermined value. The controller may be configured to automatically control the motor such that: when the probe housing motion is less than the predetermined value, the motor alters the orientation of the mirror to scan the tooth along the first closed-loop two-dimensional scan trajectory; and when the probe housing motion is not less than the predetermined value, the motor alters the orientation of the mirror to scan the tooth along the second closed-loop two-dimensional scan trajectory.

Optionally, the controller may be configured to alert an operator prior to commencing a dense scan, switch between dense and sparse scans in response to user input, and/or perform a dense scan periodically between sparse scans (such as after every 50 sparse scans).

Any embodiment may include a pulsed-to-continuous wave light buffer. The buffer includes a laser configured to output a series of pulses. Each pulse has a pulse width. An N-way optical splitter is coupled to an output of the laser, where N>1. The buffer includes at least N−1 delay lines. A respective input of each delay line of the N−1 delay lines is coupled to a respective output of the N-way splitter. The buffer includes an N-way optical combiner. A respective output of each delay line is coupled to a respective input of the N-way optical combiner. Each delay line is configured to impart a delay equal to about a different integral multiple of the pulse width, plus a constant k (k>=0).

Optionally, in any embodiment with a pulsed-to-continuous wave light buffer, the laser may be configured to output light according to a duty cycle (D). N=(1/D)−1. Optionally, in any embodiment with a pulsed-to-continuous wave light buffer, the laser may be configured to output light according to a duty cycle (D). N=1/D. Optionally, any embodiment with a pulsed-to-continuous wave light buffer may include a polarization detector optically coupled to an output of the N-way optical combiner. A polarization controller is optically coupled between the laser and one input of the N-way optical combiner. The polarization controller is communicatively coupled to the polarization detector. The polarization controller is configured to adjust polarization of light passing therethrough to match polarization of light delivered to another input of the N-way optical combiner.

In some embodiments, provided herein is an optical coherence tomography system for tooth imaging comprising a laser source with sufficient A-scan rate to reduce motion artifacts and providing synchronization signals for each OCT A-scan. In some embodiments, the system comprises a beam steering subsystem which provides a synchronized scanning pattern of the scanning beam. In some embodiments, the system comprises an optical arrangement providing sufficient optical performance for intraorally imaging the teeth. In some embodiments, the system comprises a motion tracking subsystem synchronically tracing the relative motion between the beam steering subsystem and the target to be imaged. In some embodiments, the system comprises a handheld probe that encloses at least a portion of the beam steering subsystem, the optical arrangement and the motion tracking subsystem. In some embodiments, the system comprises a digitizer which sufficiently samples the OCT signal whose bandwidth is determined by the laser source and the optical arrangement.

In some embodiments provided herein is a method to reconstruct a 3D optical coherence tomography image data for a tooth comprising a beam steering subsystem which provides a known scanning pattern of a scanning beam and a motion tracking subsystem which provides/estimates the relative motion between the beam steering subsystem and the target to be imaged. In some embodiments, the method comprises a step to combine the scanning pattern and the relative motion to correct for the motion artifact within a scan volume. In some embodiments, the method comprises a step to calculate the spatial relationship between consecutive scan volumes. In some embodiments, the method comprises a step to calculate the true optical paths of the imaging beam which is affected by different refractive indices in the scan field. In some embodiments, the method comprises a step to stitch multiple scan volumes.

In some embodiments, provided herein is an optical coherence tomography system for scanning a sample and producing imaging data of a target, the system comprising: a swept source laser configured to generate an output laser beam having a range of light wavelengths; a beam splitter configured to receive the laser beam from the swept source laser and split the laser beam into a sample arm and a reference arm; a handheld probe configured to be inserted into a patient's mouth, the probe enclosing: a collimating element configured to receive the laser beam from the beam splitter; a beam steering subsystem comprising a plurality of mirrors configured to change the direction of the laser beam; and a focusing element configured to receive the laser beam from the beam steering subsystem; an optical camera positioned within optical focus of the target and configured to be colinear with an imaging path of the laser beam and record optical data of the target; and a digitizer configured to receive analogue image data from the sample arm and the reference arm, and convert the image data into digitized image data.

In some embodiments, the laser is configured to operate at a sweeping duty cycle from about 35% to about 55%. In some embodiments, the laser is configured to operate at a sweeping duty cycle from about 35% to about 75%. In some embodiments, the laser is configured to operate at a sweeping duty cycle of about 75%. In some embodiments, the system corrects for motion of the handheld probe by providing an A-scan rate of at least 100,000 Hz and providing synchronization signals, reference signals, or trigger signals for each A-scan. In some embodiments, the system corrects for motion of the handheld probe by providing an A-scan rate of at least 150,000 Hz and providing synchronization signals, reference signals, or trigger signals for each A-scan. In some embodiments, the system corrects for motion of the handheld probe by providing an A-scan rate of at least 200,000 Hz and providing synchronization signals, reference signals, or trigger signals for each A-scan. In some embodiments, the system corrects for motion of the handheld probe by providing an A-scan rate of at least 100,000 Hz or 200,000 Hz, and providing synchronization signals, reference signals, or trigger signals for each A-scan. In some embodiments, the synchronization signals for each A-scan comprise the time when each A-Scan is started. In some embodiments, the reference signals comprise data showing a sweep path of the laser vs time. In some embodiments, the reference signals comprise Mach-Zehnder signals, Interferometer Reference signals, K-clock signals, or combinations thereof. In some embodiments, the beam steering subsystem comprising a plurality of mirrors comprises a fast scanning subsystem. In some embodiments, the fast scanning subsystem comprises a resonant scanner. In some embodiments, the plurality of mirrors comprises a galvo mirror system. In some embodiments, the plurality of mirrors comprises a polygon mirror scanner. In some embodiments, the plurality of mirrors comprises a micro-electromechanical system micromirror scanner (MEMS). In some embodiments, a scanning speed of the system ranges from 100 Hz to 20,000 Hz, or from 1500 Hz to 10,000 Hz.

In some embodiments, the system corrects for motion of the handheld probe by providing synchronization signals, reference signals, or trigger signals for each A-scan. In some embodiments, the system corrects for motion of the handheld probe by providing a synchronized scanning pattern of the laser beam. In some embodiments, the system corrects for motion of the handheld probe by providing a known time and a known position of the plurality of mirrors at a given point when reflecting the laser beam. In some embodiments, the synchronized scanning pattern comprises a raster scanning pattern. In some embodiments, the system corrects for motion of the handheld probe by determining the relative movement of the handheld probe with the optical camera. In some embodiments, the system corrects for motion of the handheld probe by correcting the digitized image data to account for the relative movement of the handheld probe when producing the image data of the target. In some embodiments, correcting the digitized image data to account for the relative movement of the handheld probe comprises applying a block-matching algorithm, contour tracking algorithm, a cross-correlation, an optical flow algorithm, a feature based algorithm, a morphological iterative closest point algorithm, a normal distribution transformation algorithm, a coherent point drift algorithm, or a combination thereof.

In some embodiments, the system is configured to operate at a sweeping duty cycle of about 50%. In some embodiments, the system further comprises a buffering system configured to increase the duty cycle of the laser, the buffering system comprising: a first delay module configured to receive a first portion of a split laser beam; a second delay module configured to receive a second portion of a split laser beam, wherein the first delay module and the second delay module are configured to delay the first portion of the split laser beam and the second portion of the split laser beam such that they do not simultaneously strike the target. In some embodiments, duty cycle of the laser is doubled.

In some embodiments, the system further comprises a polarization controller configured to tune the first portion of the split laser beam and the second portion of the split laser beam such that they have a same polarization state. In some embodiments, the system further comprises a polarization detection module. In some embodiments, the system further comprises an optical amplifier configured to increase a power level of the laser beam.

In some embodiments, the beam steering subsystem is configured to operate with a mechanical scanning angle of an additional 5% to 50% of the minimally required angle. In some embodiments, the probe further encloses a dichroic mirror configured to guide an amount of light from the laser and an amount of light in a visible wavelength to the optical camera. In some embodiments, the optical camera further comprises a lens system, wherein the lens system is configured to match the focal plane and the depth of focus of the laser profile. In some embodiments, the aperture of the OCT lens system in the handheld probe is from about 2 mm to about 15 mm in dimension (e.g., diameter). In some embodiments, the OCT lens system is configured to achieve telecentric scanning of the laser beam. In some embodiments, the aperture of the OCT lens system in the handheld probe is from about 5 mm to about 15 mm in diameter. In some embodiments, the OCT lens system is configured to vary aperture diameter by plus or minus 5 mm to achieve telecentric scanning of the laser beam. In some embodiments, the OCT objective lens is configured to be in focus of the target when it is within a range of about 1 mm to about 125 mm of the target. In some embodiments, the optical camera is configured to be in focus of the target it is when within a range of about 1 mm to about 125 mm of the target. In some embodiments, the OCT objective lens is configured to be in focus of the target when it is within a range of about 50 mm to about 125 mm of the target. In some embodiments, the optical camera is configured to be in focus of the target when it is within a range of about 50 mm to about 125 mm of the target. In some embodiments, the digitizer is a 2 channel signal digitizer.

In some embodiments, the laser is configured to operate at from about 800 nm to about 2100 nm. In some embodiments, the laser is configured to operate at 1310 nm or 1700 nm. In some embodiments, the plurality of mirrors comprises mirrors with a size from about 1 mm to about 10 mm.

Provided herein are embodiments of a method of producing an optical coherence tomography system image of a target to correct for relative motion comprising: operating an optical coherence tomography system comprising a swept source laser and generating an output laser beam having a range of light wavelengths; splitting the laser beam into a sample arm and a reference arm, steering the laser beam in a scanning pattern over the target; obtaining optical image data from an optical camera positioned within optical focus of the target configured to be colinear with an imaging path the laser beam and recording optical data of the target; receiving OCT data from the optical coherence tomography system based upon data received from the sample arm and the reference arm; receiving the optical imaging data from the optical camera; and correcting the OCT imaging data to account for relative motion of at least a portion of the OCT system by one of the following: utilizing the imaging data from the optical camera to correct determine a relative movement of a handheld probe comprising the optical camera and an output of the laser beam, and correcting the OCT imaging data based upon the determined relative movement of the handheld probe; determining relative motion from the volumetric data set by matching consecutive surface topographies of the target; or collecting motion data from one or more sensors, the one or more sensors comprising an inertial measurement unit (IMU), accelerometer, gyroscope, magnetometer, electromagnetic navigation system, or optical navigation system.

In some embodiments, the method further comprises stitching the OCT imaging data and the imaging data from the optical camera together to produce combined imaging data comprising a high resolution image of the target including volumetric data below a surface of the target. In some embodiments, the method further comprises displaying an integrated optical image on a visual interface. In some embodiments, the laser is configured to operate at a sweeping duty cycle from about 35% to about 55%. In some embodiments, the laser is configured to operate at a sweeping duty cycle from about 35% to about 75%. In some embodiments, the laser is configured to operate at a sweeping duty cycle of about 75%.

In some embodiments, operating the optical coherence tomography system comprises operating the handheld probe at a plurality of positions and a plurality of orientations. In some embodiments, obtaining optical image data from the optical camera comprises operating the handheld probe at a plurality of positions and a plurality of orientations. In some embodiments, operating the optical coherence tomography system comprises operating the OCT system at a plurality of positions and a plurality of orientations, and wherein obtaining optical image data from the optical camera comprises operating the optical camera at a plurality of positions and a plurality of orientations.

In some embodiments, the method further comprises: converting the OCT imaging data into a digitized electrical signal; and producing a volumetric data set from the digitized electrical signal. In some embodiments, the method further comprises: correcting for scan field distortion in the volumetric data set using pre-calibrated reference data to determine the true optical path of each scanning beam. In some embodiments, the method further comprises: determining features of the target based upon the volumetric data set; and segmenting the volumetric data set based upon the features of the target. In some embodiments, the method further comprises determining relative motion from the volumetric data set by matching consecutive surface topographies of the target.

In some embodiments, matching consecutive surface topographies comprises applying an algorithm comprising an Iterative Closest Points, Coherent Point Drift, Normal Distribution Transformation, or a combination thereof. In some embodiments, the method further comprises collecting motion data from one or more sensors, the one or more sensors comprising an inertial measurement unit (IMU), accelerometer, gyroscope, magnetometer, electromagnetic navigation system, or optical navigation system. In some embodiments, the optical image data comprises motion information including one or more of: the orientation, position, linear or angular velocity, linear or angular acceleration of the handheld probe.

In some embodiments, utilizing the optical image data from the optical camera to determine relative movement of the handheld probe comprises determining a true path of the laser beam based upon the motion information, and updating the volumetric data set. In some embodiments, utilizing the optical image data from the optical camera to determine relative movement of the handheld probe comprises applying a block matching algorithm, a contour tracking algorithm, a contour tracking algorithm, a cross correlation, an optical flow, or a feature based method.

In some embodiments, updating the volumetric data set comprises updating an A-scan, a B-Scan, or a C-Scan. In some embodiments, updating the volumetric data set comprises updating the A-scan based upon determining a change in position, and a change in orientation of the laser beam. In some embodiments, updating the volumetric data set comprises updating the C-scan based upon determining a change in position, and a change in orientation of the laser beam.

In some embodiments, the method further comprises correcting the volumetric data set for motion artifacts. In some embodiments, the method further comprises correcting the volumetric data set for refractive indices of the target. In some embodiments, correcting the volumetric data set for refractive indices comprises accounting for a ray shortening effect by calculating plane normal at each point on the target surface, calculating a local slope using surrounding points, and then applying Snell's law to calculate ray direction. In some embodiments, the target is a tooth, and wherein the refractive indices of the tooth are due to enamel or dentin on the tooth. In some embodiments, the target is a tooth, and wherein the refractive indices of the tooth are due to gingiva on the tooth. In some embodiments, correcting for the refractive index of the enamel improves the image of the tooth topography, or the image of the tooth below the surface of the tooth. In some embodiments, correcting for the refractive index of the enamel comprises: detecting the enamel edge in two volumetric data sets; producing a first and second array of 3D coordinates identifying the enamel edge; applying a transformation matrix to the first array to match the second array by applying deformable registration under constraints; generating a first modified array and a second array by removing outliers to create the first modified array and the second modified array; combining the first modified array and the second modified array to produce a stitched image. In some embodiments, the method further comprises applying a second transformation matrix to the first modified array and the second modified array to improve point matching.

Provided herein are embodiments of a dental optical coherence tomography system for performing an intraoral scan of a tooth and producing imaging data of the tooth, the system comprising: a swept source laser configured generate an output laser beam having a range of light wavelengths; a beam splitter configured to receive the laser beam from the swept source laser and split the laser beam into a sample arm and a reference arm, a handheld probe configured to be inserted into a patient's mouth, the probe enclosing: a collimating element receiving the laser beam from the beam splitter; a beam steering subsystem comprising one or more mirrors configured to change the direction of the laser beam; and a focusing element receiving the laser beam from the beam steering subsystem; an optical camera positioned within optical focus of the tooth colinear with an imaging path of the laser beam and record optical data of the tooth; a digitizer receiving analogue image data, and converting the image data into digitized image data; and one or more computer processors configured to implement a method comprising one of the following processes to correct for motion artifacts: correcting the OCT imaging data to account for relative motion of at least a portion of the OCT system by utilizing the imaging data from the optical camera to correct determine a relative movement of a handheld probe comprising the optical camera and an output of the laser beam, and correcting the OCT imaging data based upon the determined relative movement of the handheld probe; determining relative motion from the volumetric data set by matching consecutive surface topographies of the tooth and correcting the OCT imaging data based upon the determined relative movement of the handheld probe; or collecting motion data from one or more sensors, the one or more sensors comprising an inertial measurement unit (IMU), accelerometer, gyroscope, magnetometer, electromagnetic navigation system, or optical navigation system and correcting the OCT imaging data based upon the determined relative movement of the handheld probe; or applying a scanning pattern comprising steering the laser beam in a raster sawtooth unidirectional scanning path, a raster scanning triangular unidirectional path, a raster scanning bi-directional scanning path, a raster scanning sinusoidal unidirectional path, a raster scanning sinusoidal bi-directional scanning path, a raster scanning arbitrary waveform unidirectional path, a raster scanning arbitrary waveform or bi-directional scanning path, a Lissajous scanning path, a spiral scanning path, a circular scanning path, or a radial path, thereby capturing a multiplicity of frames in an irregular pattern, and stitching the multiplicity of frames into a single image to increase sampling density.

In some embodiments, the system corrects for motion of the handheld probe by providing an A-scan rate of at least 100,000 Hz and providing synchronization signals, reference signals, or trigger signals for each A-scan. In some embodiments, the reference signals comprise data showing a sweep path of the laser vs time. In some embodiments, the reference signals comprise Mach-Zehnder signals, Interferometer Reference signals, K-clock signals, or combinations thereof. In some embodiments, the beam steering subsystem comprising a one or more mirrors comprises a fast scanning subsystem comprising a resonant scanner a galvo mirror system, a polygon mirror scanner, a micro-electromechanical system, a micromirror scanner (MEMS), or combinations thereof.

In some embodiments, the system corrects for motion of the handheld probe by correcting the digitized image data to account for the relative movement of the handheld probe when producing the image data of the tooth. In some embodiments, correcting the digitized image data to account for the relative movement of the handheld probe comprises applying a block-matching algorithm, contour tracking algorithm, a cross-correlation, an optical flow algorithm, a feature based algorithm, a morphological iterative closest point algorithm, a normal distribution transformation algorithm, a coherent point drift algorithm, or combinations thereof.

In some embodiments, the system further comprises a buffer system configured to increase the duty cycle of the laser, the buffering system comprising: a first delay module configured to receive a first portion of a split laser beam; a second delay module configured to receive a second portion of a split laser beam, wherein the first delay module and the second delay module are configured to delay the first portion of the split laser beam and the second portion of the split laser beam such that they do not simultaneously strike the tooth.

In some embodiments, the system further comprises a polarization controller configured to tune the first portion of the split laser beam and the second portion of the split laser beam such that they have a same polarization state. In some embodiments, the probe further encloses a dichroic mirror configured to guide an amount of light from the laser and an amount of light in a visible wavelength to the optical camera. In some embodiments, the optical camera further comprises a lens system, wherein the lens system is configured to match the focal plane and the depth of focus of the laser profile, wherein the aperture of the OCT lens system in the handheld probe is from about 5 mm to about 15 mm, wherein the OCT lens system is configured to achieve telecentric scanning of the laser beam. In some embodiments, the aperture of the OCT lens system in the handheld probe is from about 5 mm to about 15 mm, wherein the OCT lens system is configured to vary aperture by plus or minus 5 mm to achieve telecentric scanning of the laser beam. In some embodiments, the OCT objective lens is configured to be in focus of the tooth when with a range of about 1 mm to about 125 mm of the tooth. In some embodiments, the process to correct for motion artifacts comprises performing (i), (ii), and (iii) of step (e). In some embodiments, the process to correct for motion artifacts comprises utilizing optical image data from the optical camera while operating the handheld probe at a plurality of positions and a plurality of orientations. In some embodiments, the process to correct for motion artifacts further comprises correcting for scan field distortion in the volumetric data set using pre-calibrated reference data to determine the true optical path of each scanning beam.

In some embodiments, the system further comprises: determining features of the tooth based upon the volumetric data set, and segmenting the volumetric data set based upon the features of the tooth. In some embodiments, the system further comprises: determining relative motion from the volumetric data set by matching consecutive surface topographies of the tooth. In some embodiments, matching consecutive surface topographies comprises applying an algorithm comprising an Iterative Closest Points, Coherent Point Drift, Normal Distribution Transformation, or combinations thereof. In some embodiments, the process to correct for motion artifacts further comprises further comprises correcting the volumetric data set for refractive indices of the tooth. In some embodiments, the process to correct for motion artifacts further comprises further comprises accounting for a ray shortening effect by calculating plane normal at teach point on the tooth surface, calculating a local slope using the surrounding points, and then applying Snell's law to calculate ray direction. In some embodiments, the system further comprises correcting for the refractive index of the enamel improves the image of the tooth topography, or the image of the tooth below the surface of the tooth.

In some embodiments, correcting for the refractive index of the enamel comprises: detecting the enamel edge; producing a first and second array of 3D coordinates identifying the enamel edge; applying a mask to the second array to correct for the refractive index of the enamel to modify the second array to produce a modified second array; applying a transformation matrix to the first array using data from the modified second array to produce a third modified array; refining the third modified array by removing outliers and applying deformable registration under constraints; and combining the first modified array and the third modified array to produce a stitched image.

In some embodiments, the one or more computer processors are further configured to implement a method comprising: steering the laser beam in a raster sawtooth unidirectional scanning path, a raster scanning triangular unidirectional path, a raster scanning bi-directional scanning path, a raster scanning sinusoidal unidirectional path, a raster scanning sinusoidal bi-directional scanning path, a raster scanning arbitrary waveform unidirectional path, a raster scanning arbitrary waveform or bi-directional scanning path, a Lassijous scanning path, a spiral scanning path, a circular scanning path, or a radial path. In some embodiments, the method further comprises capturing a multiplicity of frames and stitching the multiplicity of frames into a single image to increase sampling density. In some embodiments, the beam steering subsystem comprising the one or more mirrors configured to change the direction of the laser beam comprises a set of dual x-y resonant scanners.

In some embodiments, the beam steering subsystem comprising the one or more mirrors configured to change the direction of the laser beam comprises a one mirror system comprising one mirror, wherein the one mirror are actuated by a multi-axis actuator, a micro Electro-Mechanical System (MEMS) actuator, a piezoelectric actuator, or a voice coil actuator. In some embodiments, the beam steering subsystem comprising the one or more mirrors configured to change the direction of the laser beam comprises a two mirror system comprising two mirrors, wherein a rotational axis of the two mirrors are not in parallel. In some embodiments, the two mirrors are actuated by a multi-axis actuator, a micro Electro-Mechanical System (MEMS) actuator, a piezoelectric actuator, or a voice coil actuator. The system of claim 102, wherein the two mirrors are actuated by a galvo scanner, a resonant scanner, a polygon mirror scanner, a rotary scanner, an acousto-optic scanner, or a electro-optic scanner. In some embodiments, the beam steering subsystem comprises deformable lenses with actuators. In some embodiments, the beam steering subsystem comprises a Risley-Prism-based beam steering system. In some embodiments, the beam steering subsystem comprising the one or more mirrors configured to change the direction of the laser beam comprises a micro Electro-Mechanical System (MEMS) actuator with a single mirror and a two axis actuator. In some embodiments, the swept source laser is configured to generate the output laser beam at a small size which reduces the back-scattering photon collection efficiency, which reduces OCT signal to noise ratio, or both. In some embodiments, a diameter of the single mirror is about the diameter of the laser beam, is from about 0.5 mm to about 6 mm, or is from about 2 mm to about 3 mm. In some embodiments, the method further comprises operating the system at a scan speed from about 100 Hz to about 5000 Hz, or from about 500 Hz to about 1000 Hz. In some embodiments, the method further comprises steering the laser beam about two scanning axes with two sinusoidal waveforms with at least a first frequency and a second frequency. In some embodiments, the method further comprises configuring the greatest common divisor (GCD) of the two scanning frequencies to be around 50 Hz to 3,000 Hz, or about 100 to 1000 Hz. In some embodiments, a ratio of the first frequency to the second frequency is greater than 0.5, is about 0.66, is about 0.75, or is about 0.8. In some embodiments, the beam steering subsystem comprising the one or more mirrors configured to change the direction of the laser beam comprises two galvo scanners each comprising a motor attached to the one or more mirrors. In some embodiments, the method further comprises calibrating for a Lissajous scanning pattern, the method further comprising: synchronizing an A-scan rate with a Lissajous scan rate; locking a Lissajous scanning drive waveform to an A-scan by detecting a timing of an A-scan trigger; removing a jitter in the A-scan trigger; sampling the trigger to produce a jitterless clock; and generating a scanner drive waveform with the jitterless lock. In some embodiments, the A-scan trigger is a start-of-sweep signal or an optical feedback when the light source sweeps to a predefined wavelength. In some embodiments, removing the jitter is performed by a phase lock loop chip, or a microcontroller. In some embodiments, the method comprise sampling a number of A-scans which is less than a number of scans of a Lissajous scan to form beam spots, wherein a coordinate position of the beam spots are known, identifying the special position of the laser beam when at each of the beam spots, thereby calibrating the Lissajous scanning pattern. In some embodiments, there is an imaging sensor, wherein the imaging sensor is sensitive to a wavelength of the laser beam, optionally, wherein the wavelength is infrared and wherein the imaging sensor comprises InGaAs or Ge. In some embodiments, the imaging sensor comprises a diameter greater than or equal to a field of view of the system. In some embodiments, the imaging sensor is positioned within a field of view of the system, near a focal plane of the system.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Optical Coherence Tomography (OCT) systems employ imaging technology that guides a probing optical beam onto an object and detects backscatter. They usually employ a point scanning mechanism which forms the sampling light into a single beam in open air. When the sampling beam is incident upon the object surface, the beam may also propagate into the object and form an optical path. OCT captures information from the optical path. The point scanning mechanism then moves the beam to a different location on the object surface and forms a different optical path. The points on the object surface are sampled sequentially, after which some information of the object can be recorded.

Common requirements for the scanning path are high geometric accuracy, high repeatability, high duty cycle, evenly distributed scan pattern and high speed. High geometric accuracy is required to recover the true structure. Sometime calibration of scanning path is also highly desired to increase accuracy. High repeatability is required for the accurate reconstruction of the object geometry when there are repeating scans. High duty cycle is desired to scan as many sample points as possible. A roughly even scan pattern is desired to reduce sampling error for complex structures. High speed is desired or even required when the object has movement with respect to the scanner.

This disclosure describes some exemplary embodiments of OCT scanning systems for ultrafast scan speed, high repeatability, and high geometric accuracy, with consideration on scan point distribution and duty cycle.

There are technical constraints to obtain OCT images of high quality. Firstly, OCT usually has a short working distance on the order of millimeters, and a tissue penetration depth of 1 to 10 millimeters. Unlike X-ray or CT where the imager can be placed extraorally, OCT scanner typically has an intraoral portion close to the teeth during scanning. In some embodiments, a handheld design is desired, in which case there are limitations on the weight and dimensions of the scanner. Secondly, OCT is usually used in a laser scanning configuration. Although a state-of-the-art OCT may be able to provide a high A-scan rate, operator or patient motion can introduce noticeable image distortion. Careful decisions should be made to minimize and correct for such motion artifacts. Thirdly, owing to the limited dimension of the intraoral portion and the sampling density, the field of view of OCT scanning is typically around 10 by 10 by 10 cubic millimeters. Variation applies for different system designs. The volume where OCT acquires data from is referred to as an OCT scan volume throughout the specification. To scan a whole tooth or multiple teeth may require taking multiple scan volumes and the volume data need to be stitched (e.g., registered and fused) together. System hardware and software need to be carefully designed to facilitate such a stitching algorithm.

Figure 1:
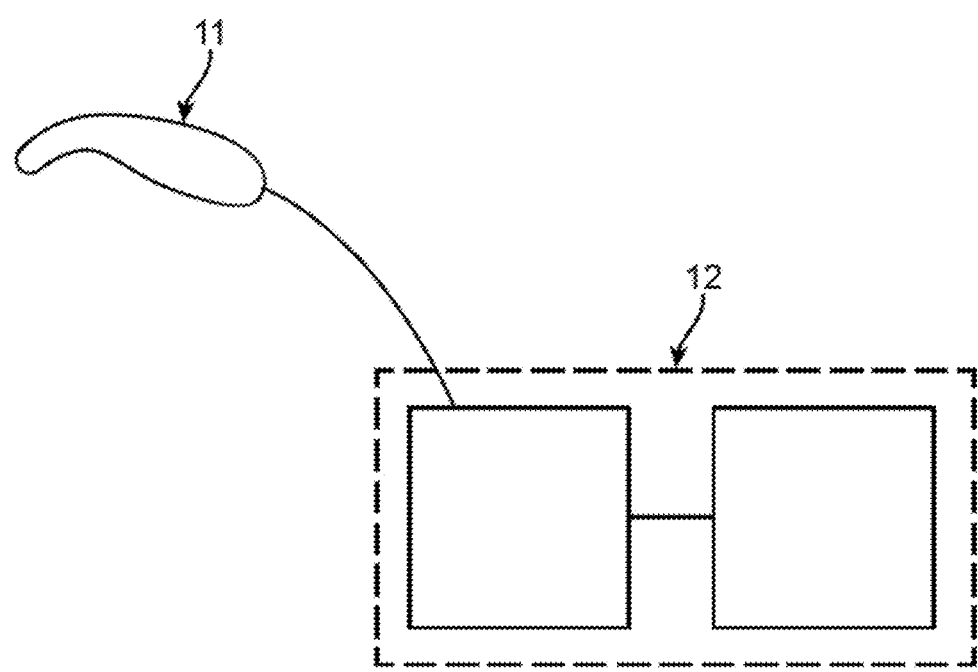
FIG. 1 depicts an exemplary embodiment of the OCT system architecture, according to some embodiments.

FIG. 1 depicts an exemplary embodiment of the OCT system architecture. In some embodiments, the system comprises a handheld scanning probe 11 and a system engine 12. In some embodiments, the handheld scanning probe encloses the sample arm of an OCT system. In some embodiments, a probing beam profile is formed to meet certain characteristics and rapidly modify the beam in a predefined pattern, such that the acquired image data may be used for reconstruction. In some embodiments, photons backscattered from the tissue surface carry information used to reconstruct the surface topography. Photons backscattered from the internal tissue may carry information which is used to visualize the internal tissue structure or function. The system engine may also include a reference arm, interferometer, light source, detection subsystems and their respective control module(s). The image data may then be digitized and streamed to a computer for further analysis and visualization.

Figure 2A:
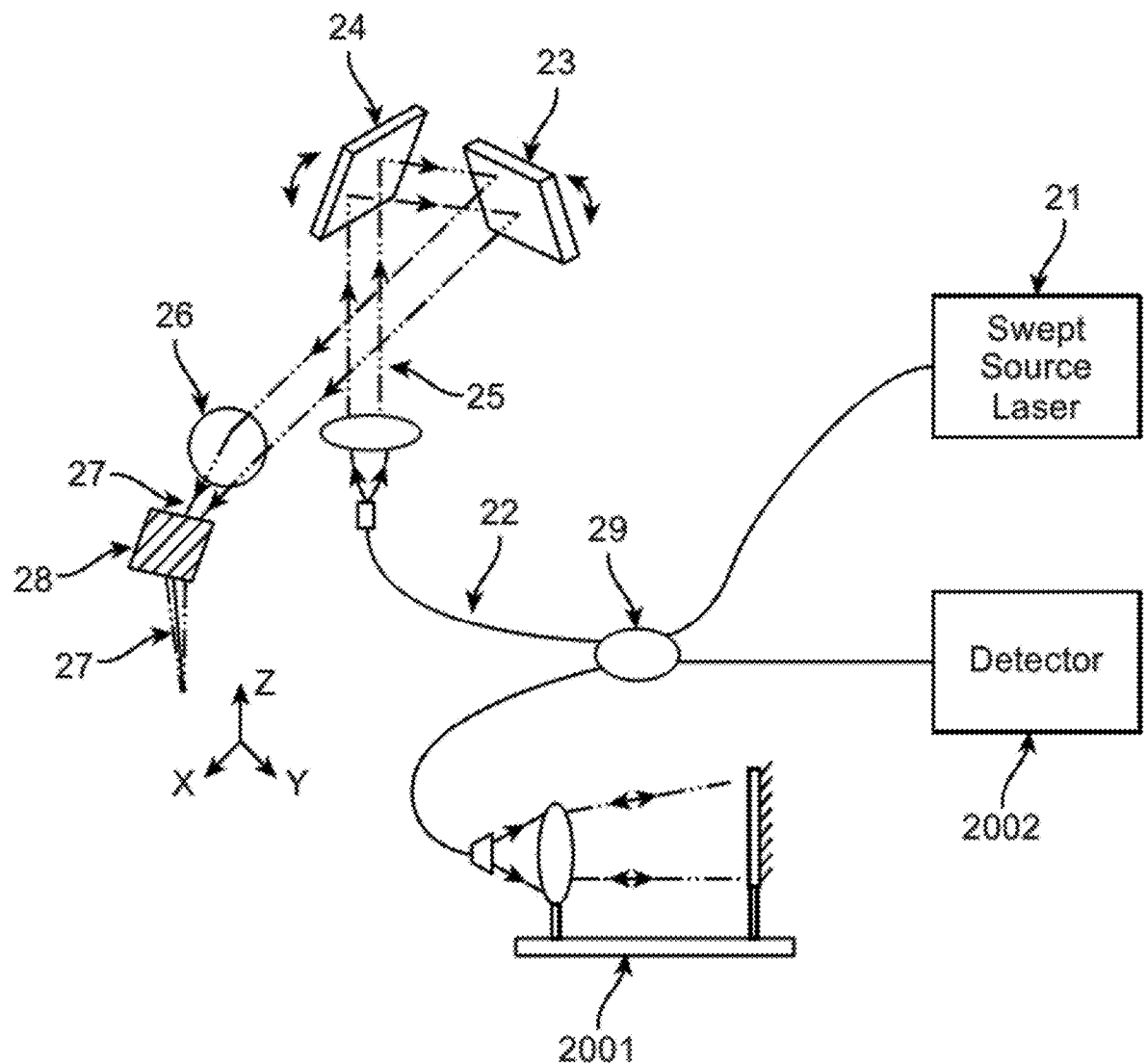
FIG. 2A depicts an exemplary embodiment of a Swept Source OCT system with a volumetric scanning probe design, according to some embodiments.

The present disclosure may address the above needs by providing an OCT scanning system with ultrafast scan speed thereby reducing motion artifacts. FIG. 2A depicts an exemplary embodiment of a Swept Source OCT system with a volumetric scanning probe design, according to some embodiments. A swept source OCT system usually has a higher volumetric scanning rate, which may reduce motion artifacts. Some embodiments of a swept source OCT system involve a long coherence length, which may allow for minimum signal-to-noise ratio falloff and a long imaging range. In some embodiments, it allows for capturing the whole anatomy of the teeth which have a height change more than 10 mm. In some embodiments, the swept source 21 emits light sweeping in a certain wavelength range into a beam splitter 29. In some embodiments, the light is then split into the sample arm 22 and the reference arm 2001. In some embodiments, the sample arm 22 includes a collimating element 25, two mirrors 23 and 24 with non-parallel rotating axes, which steer the collimated beam to follow a raster scanning pattern or any other appropriate pattern. In some embodiments, the beam is then refocused by a focusing element 26 in order to improve the lateral resolution of OCT imaging. A mirror 28 may be installed to bend the scanning beam 27 at a desired angle. In some embodiments, the backscattered light from the subject travels backwards along the incident optical path. In some embodiments, the backscattered light then interferes with the light which comes back from the reference arm 2001 at the coupler 29. The interference signal is then collected by the detection module 2002 for further analysis.

Figure 2B:
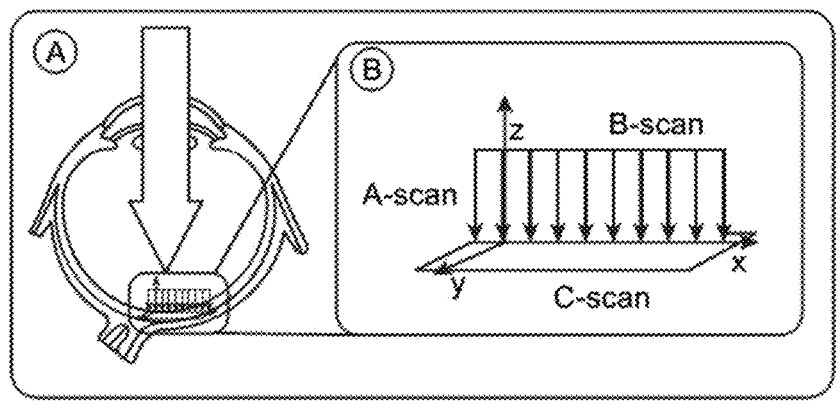
FIGS. 2B-2D depict swept scanning methods, according to some embodiments.
Figure 2C:
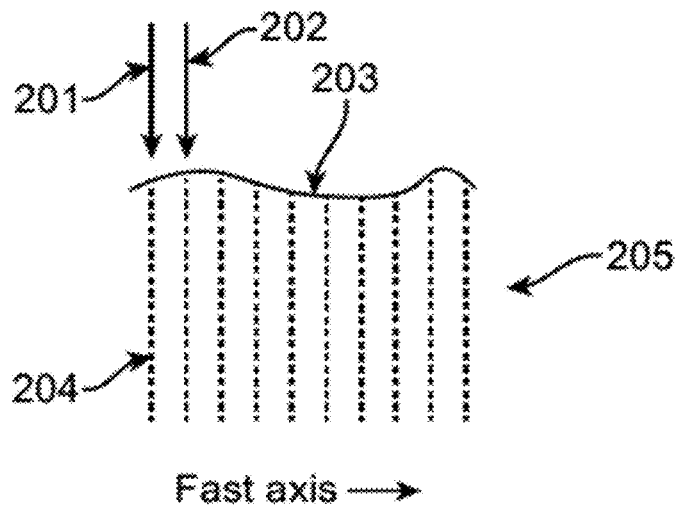
Figure 2D:
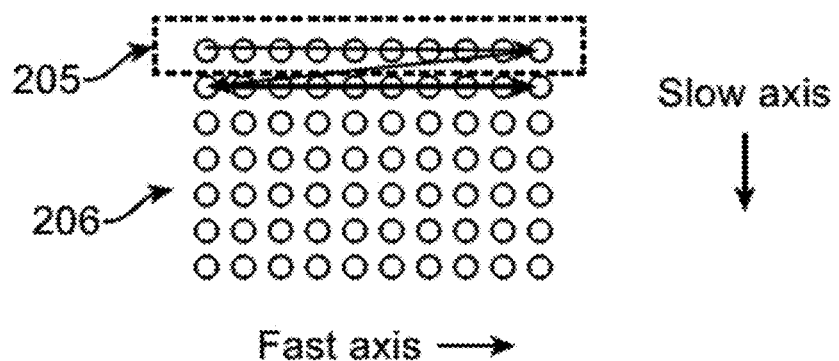

FIGS. 2B-2D depict embodiments of swept scanning methods and explain some terminologies used in the OCT scanning system. Beam 201 may represent the OCT scanning beam position and orientation at time t, and is incident onto tissue surface 203. As the beam propagates along a path in the tissue, it may be partially backscattered, propagate backwards, and be detected by the OCT system. This path may be referred to as an A-scan. Each A-scan may correspond to one laser sweep along the sweeping wavelength. The direction of the A-scan is usually called the axial direction or the Z direction. The beam may then be moved to the next position 202 at time $t_0+\Delta t$ to capture the next A-scan. The scanning may continue so that a group of A-scans is captured, which represents a cross-section 205 of the tissue, and may be referred to as a B-scan. The B-scan scanning direction is lateral with respect to the A-scan and may be called the fast axis. The remaining direction in the 3D space, which is perpendicular to the axial direction and the fast axis, may be referred to as the slow axis. Conventional OCT scanning techniques are further described with respect to FIGS. 19-24. In a raster scanning method, as depicted in FIG. 2D, the beam can follow a zig-zag pattern so that each B-scan is offset with respect to the prior B-scan. A group of B-scans forms a volumetric data, called a C-scan 206 or a volume scan.

In some embodiments, the beam profile 27, depicted in FIG. 2A, is a Gaussian profile. In some embodiments, the focal plane is the lateral plane (with respect to the beam propagation direction) where the beam waist lies. The $1/e^2$ diameter at the beam waist, also known as the spot size, may range from 1 μm to 50 μm. When an even spaced lateral scan is performed, the distance between two neighboring sampling points may range from 1 μm to 200 μm.

In some embodiments, the OCT system architecture may be configured to utilize the light more efficiently to increase the signal-to-noise ratio. In some other embodiments, the OCT system can be configured to utilize the polarization state of the light to extract tissue characteristics and to improve the image quality.

Figure 3:
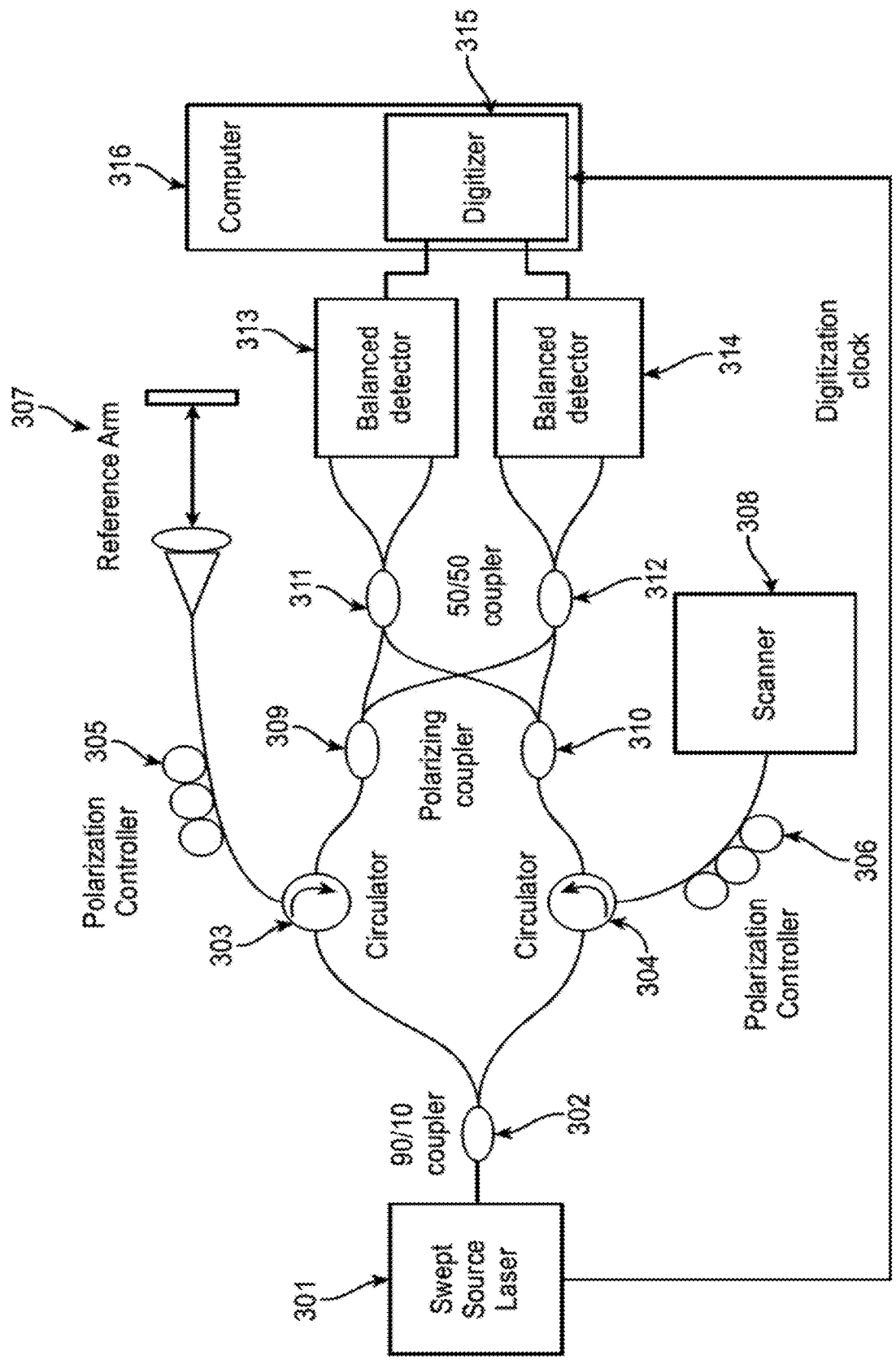
FIG. 3 depicts an OCT system, according to some embodiments.

FIG. 3 depicts an exemplary embodiment of an OCT system for the polarization state extraction. A polarization sensitive OCT system may be particularly useful for imaging the enamel because it is birefringent material. Polarization-sensitive OCT may detect the birefringence, or may be used to remove birefringence artifacts in the image to easily detect other features in the enamel. In some embodiments, the swept source laser 301 is connected to a coupler 302. In some embodiments, to be power efficient, more power may be delivered to the sample arm to increase the signal strength, while keeping the emission under the Accessible Emission Limits (AEL) safety limit and leaving sufficient optical power in the reference arm to make use of the full dynamic range of the detection module in the system. AEL is the maximum accessible level of laser radiation permitted within a particular laser class. In some embodiments, the split ratio of the coupler ranges from 99%/1% to 70%/30%. In some embodiments, the split ratio of the coupler ranges from 95%/5% to 90%/10%. Polarization controllers 305 and 306 may be added to the sample arm and the reference arm respectively to adjust the polarization states of light for the extraction of polarization sensitive information. Additional polarization controllers (not shown) may be added before the polarizing couplers 309 and 310. These polarizing couplers may split the light from the sample and reference arms into orthogonal states, which then independently interfere at the 50/50 couplers 311 and 312 and are detected by independent detectors 313 and 314. In some embodiments, a two-signal channel digitizer 315 is used in the computer 316 to detect the signal. A two-signal channel digitizer may reduce the space requirement in the computer. Resampling the OCT signal may require a reference clock from the laser showing the sweeping wavelength versus time relationship. This reference clock is also fed to the digitizer 315.

In some embodiments, the swept-source is configured to specifically meet the need for teeth imaging. The accuracy of the OCT system may be sufficient to identify features of interest in the teeth, such as the topography or caries disease. Therefore, the 15 dB bandwidth of the light source may be greater than 50 nm so that the axial full-width at half maximum (FWHM) of the OCT imaging can be small enough.

In some embodiments, the center wavelength of the swept-source is in the near infrared regime, more specifically, from 800 um to 2.5 um, for instance, at 840 nm, 1060 nm, 1310 nm, 1700 nm, 2100 nm etc. In some embodiments, the center wavelength is about 1310 nm such that the system can usually penetrate deeper into the biological tissue compared to other shorter wavelengths. In some embodiments, the swept source around 1310 nm is more readily available. In some embodiments the center wavelength is around 1700 nm for lower water absorption.

Figure 4:
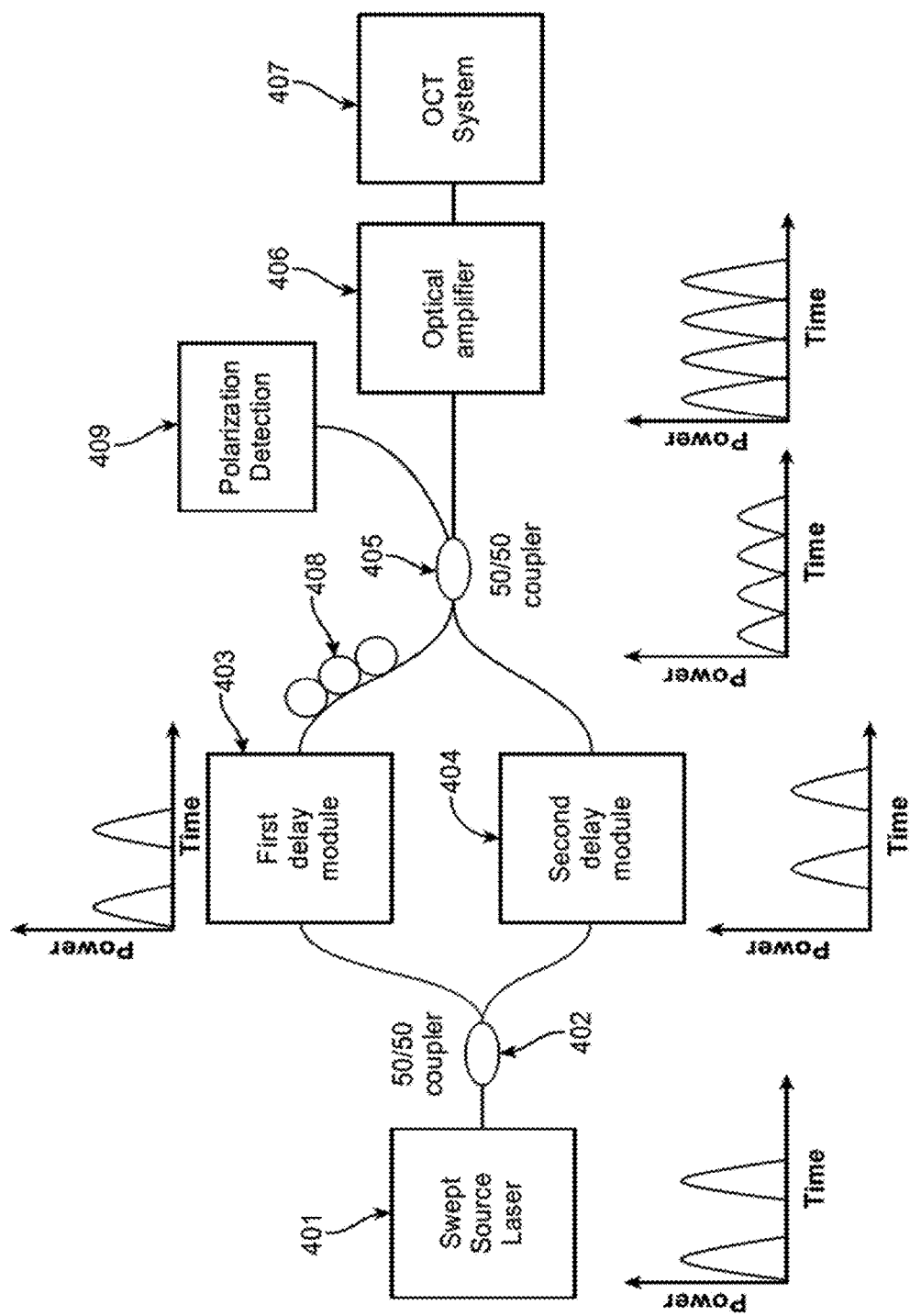
FIG. 4 depicts a buffer system used to increase the duty cycle of the light source, according to some embodiments.

In some embodiments, the swept-source laser comprises a wavelength sweeping duty cycle equal to or less than 50%. In other words, the swept-source laser may have lasing cycles, and the duration when the swept-source laser emits usable lights may be equal to or less than half of the cycle. In these lasers, a buffer system may be used to increase the duty cycle of the light source system and effectively the scan rate of the system, as depicted in FIG. 4. The power versus time graphs depict the timing and the power of the light emission at each component.

In some embodiments, the light from the swept source 401 may be split by a 50/50 coupler 402 into a buffer system. In some embodiments, the first portion of the split light travels through a first delay module 403. In some embodiments, the second portion of the split light travels through a second delay module 404. In some embodiments, the difference between the first delay and the second delay is configured such that when the light from the modules 403 and 404 are combined again in the second 50/50 coupler 405, the light with the first delay and the light with the second delay do not overlap temporally. In such a configuration, the combined duty cycle of the light source system is effectively doubled compared to the swept-source itself. In some embodiments, the optical delay can be introduced by a long waveguide such as an optical fiber spool.

In some embodiments, an optical amplifier can be used in conjunction with the light splitting configuration, so that the first portion and the second portion of the split light can be tuned to a desired power level. In some embodiments, a polarization controller 408 and a polarization detection module 409 are used in conjunction with the light splitting configuration, so that the first delayed portion and the second delayed portion of the split light can be tuned to the same polarization state. This may be particularly important for the teeth imaging because the enamel is birefringent material and sensitive to the polarization state of light. In some embodiments, the optical arrangement of the first delay module 403 and the second delay module 404 affects the output polarization states of light. In some cases, when the two portions of light have different polarization states without any compensation, the system emits light of alternating polarization states in every other A-scan, which introduces different polarization artifacts to every other A-scan in the image and creates image texture with artifacts.

Figure 5:
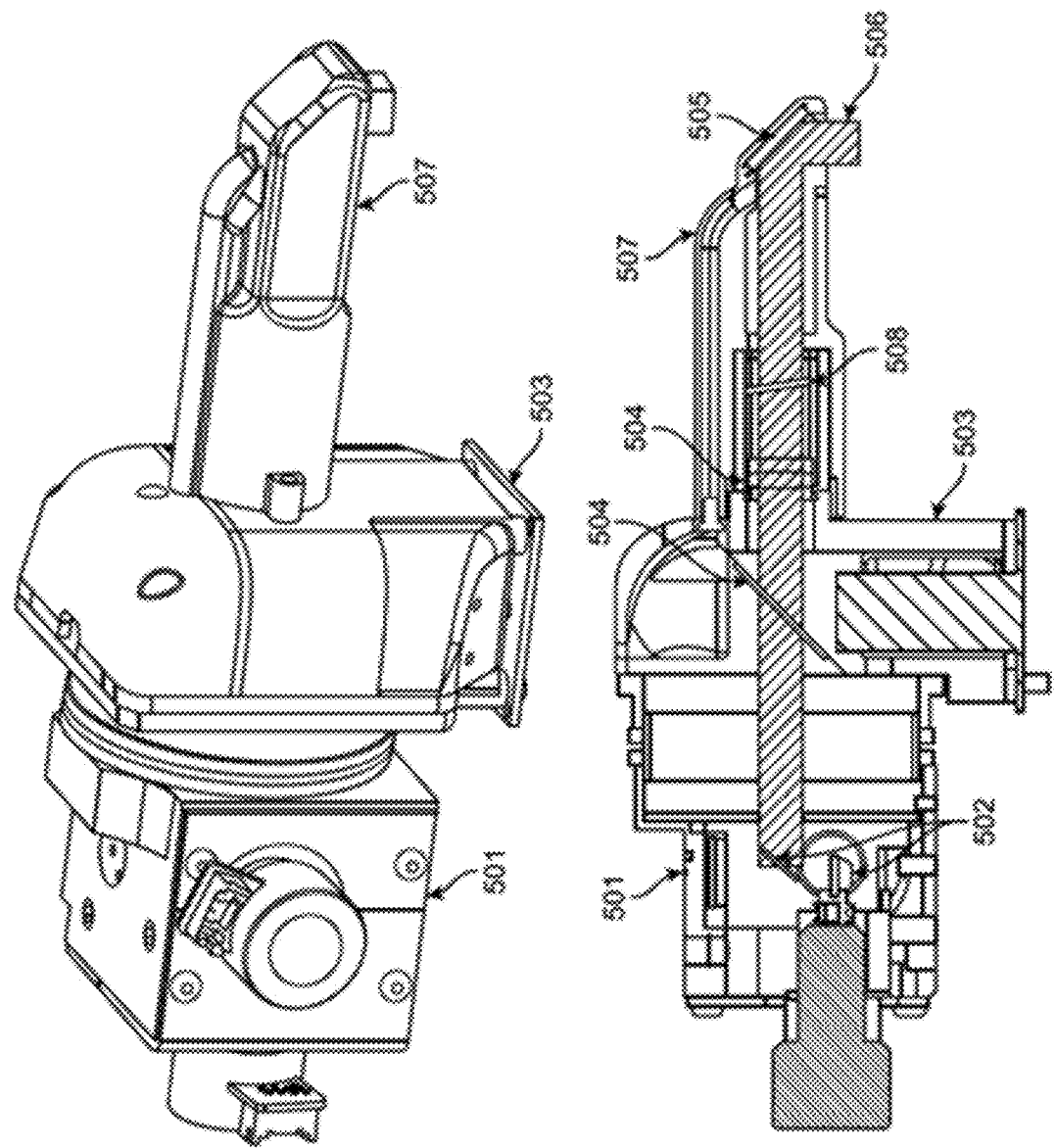
FIG. 5 depicts a scanning probe in a sample arm, according to some embodiments.

FIG. 5 depicts an exemplary embodiment of the scanning probe in the sample arm. The sample arm light may be collimated and guided into a beam steering module 501. The beam steering module 501 may have two mirrors 502 as the beam reflecting elements. In some embodiments, the mirrors 502 are mounted on oscillating components such as two galvo motors, which form a galvo mirror subsystem. The galvo mirror subsystem can be used for its deterministic motion feedback and control, and scanning linearity, which may be desirable for simplified data reconstruction in later processing stages. The oscillating axes of the two mirrors may be perpendicular for easy position control, so that one mirror controls the beam sweeping across one direction and the other mirror controls the orthogonal direction. In some embodiments, the galvo mirror subsystem is configured to scan as fast as possible, but also has minimum scan field distortion and high repeatability. Therefore, the subsystem may be configured to scan unidirectionally, and use only the linearly scanning portion. In some embodiments, the size of the collimated beam incident onto the galvo mirror determines the size of the mirror. In some embodiments, the size of the mirror determines the linear scanning frequency range, which in turn determines the maximum mechanical scanning speed. In some embodiments, the collimated beam size can be from 1 mm to 3 mm for sufficient lateral spot size in tissue scanning, which is beneficial for tissue feature recognition and measurement accuracy. In some embodiments, the galvo mirror's size is 3 mm to 7 mm. In some embodiments, the scanning frequency ranges from 100 Hz to 400 Hz so that the galvo motor is still in the linear scanning regime but as fast as the subsystem allows.

In some embodiments, the beam steered by the galvo mirror subsystem is then refocused by a lens system 504, reflected by a mirror 505 and exits through the imaging window 506. A transparent window 508 may be installed to prevent contamination of the lens system 504. In some exemplary embodiments, one may configure the OCT focal plane to be away from the outer surface of the sleeve 507 by 1 mm to 5 mm. This may allow for one to keep the sleeve 507 relatively close to the target tooth without stretching the subject's cheek or having the subject open the mouth wide. In some embodiments, it may be desired to maintain a low profile sleeve 507 for the comfort of the subject. To achieve a low sleeve profile, lenses of small aperture and long focal lengths may be used. In some embodiments, the aperture of the lens 504 is about 5 mm to 15 mm. In some embodiments, the focal length of the refocusing lens system is about 50 mm to 125 mm. In some embodiments, the galvo mirrors 502 are positioned away from the refocusing lens system 504 by the focal length within a +/−5 mm to achieve or approximate telecentric scanning of the OCT beam. The optical element in lens system 504 may be a single lens, achromatic lens, any combination of lens assembly, diffractive lens, metalens, or another suitable optical element. The optical element may be made from any suitable material.

In some embodiments, a video camera visualization of the tissue scanned by OCT is provided. OCT images require 3D reconstruction, and real-time OCT visualization may require high computational power. Therefore, visualizing OCT data in real time may not be cost-effective, and visualization generated by a video camera may supplement or substitute for real-time OCT visualization. In some embodiments, the system utilizes video camera motion tracking technology to correct for the motion distortion. FIG. 5 depicts a collinear video camera configuration with OCT imaging path, which is achieved by a dichroic mirror 504 and a video camera 503. The dichroic mirror 504 is configured to transmit OCT light and reflect visible light. In some embodiments, the visible light is reflected or scattered by the tooth and redirected to the camera 503. In some embodiments, the lens system in the camera 503 is configured to match the focal plane and the depth of focus of the OCT beam profile. For example, when the OCT focal plane is 2 mm away from the outer profile of the sleeve 507 and has a depth of field of 2 mm, the tooth surface of interest may be placed about 1 mm away from the sleeve 507, such that the depth of field is within the tooth. In such an example, the focal plane of the video camera may be provided 1 mm to 2 mm away from the sleeve 507, so that when the video camera image is in focus, the OCT imaging is close to its ideal range.

Scanner Actuators

In one embodiment, the control of the optical scanning beam is done by using at least one mirror. The scan path can be controlled by changing the orientation of the mirror and therefore the reflected direction of beam propagation. The mirror or mirrors can be motorized and be programmed to change the orientation of the mirror surface in a defined pattern.

In some embodiments, there can be one mirror system where the mirror can be mounted on a two-axis or multi-axis actuator, such as a Micro Electro-Mechanical System (MEMS) actuator, piezoelectric actuator, voice coil actuator, etc.

In some other embodiments, there can also be a two or more mirror system. The rotational axes of these mirrors need not necessarily be in perpendicular. The type of actuator for each mirror can be the same or different. The actuator can be one of the aforementioned ones. In addition, the actuator can also be a galvo scanner, resonant scanner, polygon mirror scanner, rotary scanner, acousto-optic scanner, electro-optic scanner etc.

In some other embodiments, the control of the optical scanning beam is done by using deformable lenses with actuators. In yet some other embodiments, the control of the optical scanning beam is done by Risley-Prism-based beam steering systems.

Scanning Patterns

In some embodiments, wherein the scanning pattern is raster scanning, a first galvo mirror scans along the fast axis, while a second galvo mirror scans along the slow axis. The OCT beam guided into the galvo mirror subsystem may be incident onto the first mirror on the fast axis, and then reflected onto the second mirror on the slow axis. In some embodiments, this allows the active area of the mirror to be reduced, hence a smaller mass oscillating along the fast axis, resulting in less mirror deformation and a higher scanning speed on the fast axis.

Ultrafast Scanning Path and Configuration

Ultrafast scanning speed is highly desired to reduce motion blur. It can be achieved by a combination of selecting high speed actuators, and employing linear or non-linear scanning trajectories, limiting actuator overshot or mirror deformation, selecting sampling density and the field of view (FOV), etc.

In some embodiments, ultrafast speed is achieved by having a fast scanning axis along with a high scanning frequency. The actuator for the fast axis mirror can be driven with a high frequency sinusoidal waveform. Other harmonics can be added to the drive waveform to improve linearity, as long as the actuator or the system overshot is acceptable. In one embodiment, a polygon mirror scanner is used in the fast axis.

In some embodiments, the other scan axis is a slower scanning actuator and mirror. The combination of a fast scanning axis and a slow scanning axis results in a raster scanning trajectory, which can be unidirectional or bi-directional. In some other embodiments, the other scan axis can also scan in high frequency but different from that of the first axis, which forms a Lissajous scanning pattern. In yet another embodiment, the two axes can be in the same high frequency but with varying scanning angle, which forms a spiral scanning pattern.

In some embodiments, wherein there is a need for high OCT volume rate, the mirror along the fast axis may need to scan up to 10,000 Hz. In some embodiments, the scanning probe design may take into consideration the laser A-scan rate, the incident parallel beam size and the scanning field of view. In some embodiments, the laser A-scan rate determines the maximum scan rate the system can achieve. In some embodiments, the beam size determines the scanning lateral resolution and the depth of field. In some embodiments, the scanning field of view determines the area one scan volume can cover. For example, in the Gaussian beam configuration, the projection of the mirror along the beam direction may be about $1/e^2$ the beam diameter. In some embodiments, the projection of the mirror along the beam direction may be about 1% the beam diameter. In some embodiments, the projection of the mirror along the beam direction may be about 0.1% beam diameter. In some embodiments, the mechanical beam steering angle should match the scanning field of view, scanning an additional angle for ease of optical alignment. In some embodiments, scanning an extra angle causes the laser not to scan the field of view and reduces the duty cycle. Therefore, the mechanical scanning angle may scan an extra 5% to 50% of the minimally required angle to achieve the field of view.

In some embodiments, the fast scanning mirror is mounted on a resonant scanner to achieve a higher speed. In some embodiments, the resonant scanner is utilized for its sinusoidal characteristics of the scanning angle. In some embodiments, the resonant scanner operates at a fixed frequency. In some embodiments, the frequency and the phase of the scanning sine wave can be used to calibrate the scanning nonlinearity. In some embodiments, the scanning frequency can be configured to 1,500 Hz to 10,000 Hz. For example, when using a 200,000 Hz A-scan swept source and capturing 20 volumes/second, each volume consists of 10,000 A-scans. In some embodiments, one can configure a 100 A-scans per B-scan, and 100 B-scans per volume scanning pattern. In such an exemplary embodiment, the resonant scanning can be configured to 2,000 Hz.

In some other embodiments, the fast scanning mirror comprises a polygon rotating mirror to achieve a higher speed. In some embodiments, the polygon mirror scanner is utilized for its linear characteristics of the scanning angle. In some embodiments, the rotating speed and the start-of-scan signal from the polygon scanner are used to calibrate the scanning field. In some embodiments, ball bearings are utilized to allow the scanner to be oriented in an arbitrary direction.

In some embodiments, polygon mirror scanners with ball bearings have a maximum rotation per minute (RPM). In some embodiments, the configuration of the appropriate number of facets of the polygon mirror and the RPM should match the rest of the scanning optics to maximize the scanning duty cycle, because, in some embodiments, the higher the scanning duty cycle, the faster the system can acquire data, thereby producing less motion artifacts. In some embodiments, if the scanning optics requires a +/−5° optical scanning angle from the fast axis, the required mechanical scanning angle at the polygon mirror is halved, which is a total of 5° per facet. In some embodiments, extra mechanical scanning angle is employed for tolerance stacking and the introduction of the start-of-scan signal. In some embodiments, the polygon mirror may have 6° per facet, which results in a 60 facet polygon mirror (360%/6° per facet). In some embodiments, to achieve, for instance, 2,000 Hz fast axis scan rate, the polygon mirror can be configured to rotate at 2,000 RPM. In some embodiments, the mechanical scanning angle is 101% to 200% of the required optical scanning angle.

In some embodiments, a mirror mounted on a Microelectromechanical system (MEMS) can be used to replace the mirror on the fast axis or both mirrors. In some embodiments, small MEMS mirrors can be configured to scan in two axes. By reducing the size of the mirror and limiting the scanning angle, the MEMS mirror may be configured to scan at a few thousand kilo-Hertz.

In some embodiments, wherein an OCT system uses the swept laser as the light source, the sampling frequency h can be determined by multiple factors, e.g., the A-scan rate, center wavelength, sweeping bandwidth, laser sweeping duty cycle, beam steering duty cycle and the imaging depth, etc. In some embodiments, the reflected light signal is digitized by an A/D digitizer. In some embodiments, the A-scan rate is as high as possible to minimize the motion artifacts in the C-scans, as long as the sampling rate is within the capacity of the digitizer. In some embodiments, the high-end swept laser can scan as fast as more than 1,000,000 A-scans per second.

In some embodiments, a system configuration comprises at least about a 6 mm by 6 mm field of view with the raster scanning, and 10 C-scans per second. In some embodiments, an 8 mm by 8 mm field of view with the raster scanning, and 25 C-scans per second is provided. In some embodiments, higher C-scan rate is desired because each C-scan will have fewer motion artifacts. In some embodiments, the lateral spacing between A-scans, or the lateral sampling resolution, is optimized by considering the average motion speed of the scanning probe. In some embodiments, if the average motion speed is high, it means there will be fewer C-scans capturing data for one tooth. In some embodiments, higher lateral sampling resolution would make sure that the system has sufficient data to reconstruct the tooth. In an example, assuming that the sampling resolution is 100 um, in an 8 mm by 8 mm field of view and 25 C-scans per second system, each C-scan has a scan pattern of at least 80 points by 80 points (8 mm divided by 100 μm). In some embodiments, a square pattern is utilized for isotropicity in the fast and slow axes.

In some embodiments, a raster scanning system scans in the slow axis with about 100% duty cycle with various technologies, for example, a galvo scanning mirror. The fast axis, on the other hand, may have a less than 100% duty cycle due to mirror flyback/reset (as in the galvo, resonant or MEMS scanner) or the extra time to identify the start of scan (as in the polygon scanner). Therefore, the actual A-scan per C-scan may be estimated as 80*80/(fast axis duty cycle). In some embodiments, a 75% duty cycle is used, which results in at least 8,534 A-scans per C-scan and A laser sweeping at least at 213,333 Hz. Therefore, a swept-source may sweep at least at 100,000 Hz, 200,000 Hz, or higher.

Scanning Patterns

In other embodiments, various beam steering/scanning paths can be applied, including but not limited to raster scanning with a sawtooth unidirectional scanning path, raster scanning with a triangular unidirectional or bi-directional scanning path, raster scanning with a sinusoidal unidirectional or bi-directional scanning path, raster scanning with an arbitrary waveform unidirectional or bi-directional scanning path, Lissajous path, spiral path, circular path, radial path, etc. In some cases, applying an alternate scanning pattern as described herein can reduce motion artifacts resulting from movement of the subject during scanning. In a standard raster scanning, the distance between the first pixels in each row (e.g., at 0,1; 0,2; 0,3 in an x-y coordinate plane) and the distance between the first and last pixels scanned, takes the longest time between scans, and creates the possibility of significant motion artifacts between the pixels rendered from these scans. When scanning in an alternate pattern as described herein, the greatest time delay is not between pixels of adjacent rows, but is instead between pixels of irregular intervals about the target scan.

For example, in the standard raster scanning, the laser sweeps across (covers) a 2D region, and two significantly different scan frequencies are used-a fast scan rate along a typically horizontal line, and a slow scan rate along the y axis. Often the second scan is held constant during the first scan sweep. For example, a first fast scan in the horizontal (x) direction without any movement in the second vertical (y) direction. This results in a high sampling rate along the first direction with little to no motion artifacts. But, across the entire frame and depending on the scan rate in the second direction, there can be a significant delay between the first line and the last, possibly resulting in motion artifacts across the entire frame. The time delay gradually increases along the slow scan axis, which may create a motion error drift, usually in the diagonal direction. Such a gradual drift could pose a problem when rendering a scan image for stitching multiple volumes if not corrected, as the drift could accumulate across subsequent scans.

A Lissajous scan pattern, or other alternative scanning pattern described herein, may effectively redistribute the scan points in the scan field, therefore interleaving scan points with large and small motion artifacts. Samples may be captured across the entire frame at the rate of the greatest common denominator of the two scanning frequencies. While the sampling in a single "image" is sparser across the entire frame than with a raster scan approach, motion artifacts may be significantly reduced or eliminated. Denser sampling is accomplished by capturing a multiplicity of frames and registering (or stitching) them together to achieve desired coverage and sampling density. Motion artifacts may be further reduced by applying a smoothing filter or taking multiple scans with small amounts of spatial displacement. Lissajous scanning, or other alternative scanning pattern described herein, may be implemented with a polygon mirror, a galvo scanner, a resonant scanner, or a MEMS scanner, or other scanners and reflectors known within the art, and is not limited to the structures described herein. Alternative configurations of the OCT system may be utilized to permit for the alternate scanning patterns. In some embodiments, the system may comprise dual x-y resonant scanners.

MEMS Lissajous Pattern

In one exemplary embodiment, the optical scanning system is a MEMS scanner with a single mirror and a two axis actuator. A single mirror system has the potential to greatly reduce the space required. In general, the larger the mirror size, the slower it scans. Therefore, a small mirror is preferred for ultrafast scanning. On the other hand, the mirror size needs to be at least similar to or bigger than the optical scanning beam size, therefore setting an upper limit for the beam size. Smaller beam size in general reduces the back-scattering photon collection efficiency for OCT, which will reduce OCT signal-to-noise ratio. A proper size mirror should be determined to balance the tradeoff between the scan speed and the signal-to-noise ratio. The mirror size can be determined empirically.

In one embodiment, the mirror size can be 0.5 mm to 6 mm, preferably 2 mm to 3 mm. The scan speed can be 100 Hz to 5,000 Hz, preferably 500 Hz to 1,000 Hz.

In one embodiment, the scan pattern can be sinusoidal along the fast scan axis, and linear along the slow scan axis, which forms a raster scanning pattern. In another embodiment, the two scanning axes can be two sinusoidal waveforms with different frequencies. It is highly preferable to configure the greatest common divisor (GCD) of the two scanning frequencies to be around 50 Hz to 3,000 Hz. The GCD is the frequency of the scanner performing the Lissajous pattern. In one embodiment, the GCD can be 100 Hz to 1,000 Hz. The ratio between the slower scanning frequency and the faster frequency is preferably greater than %. A higher ratio allows the Lissajous pattern to scan the FOV more evenly, therefore reducing the sampling error. In one embodiment, the ratio between the slower scanning frequency and the faster frequency can be ⅔, ¾, ⅘, etc.

Galvo Lissajous Pattern

In another exemplary embodiment, the optical scanning system consists of two galvo scanners, each of which has a motorized mirror. Although the galvo scanner is larger in size, it can usually reach a higher scanning speed for the same size mirror. The aforementioned mirror size and scanning frequency specifications apply.

Ultrafast Lissajous Scanning Calibration

The calibration for Lissajous pattern can be challenging when a high calibration accuracy is required. Knowing the exact position of each A-scan can be affected by different sources of error. The motor control signal and the OCT A-scan may have a synchronization error. The scanning mirror may deform during scanning. There will also be scanning field distortion and aberration. In a dense and evenly distributed scanning pattern, calibration is relatively simple. A common calibration method is to scan a phantom with known geometry. Because the scan pattern is dense and even, it is straightforward to identify the markers on the phantom, which can be used for calibration. In a Lissajous pattern on the other hand, the scan trajectory is less well defined. The FOV is unevenly scanned. In an ultrafast Lissajous pattern, the field is sparsely scanned to increase scanning speed. It may be difficult to register the scanning data to spatial coordinates to recover the object. Calibration is still possible if the Lissajous pattern is repeatable, and one can identify the spatial position of the scanning beam when an A-scan is captured.

To make the Lissajous pattern repeatable, in one exemplary embodiment, the Lissajous scanning should be synchronized with the OCT A-scan rate. OCT A-scan rate is usually much higher than the Lissajous scanning. The system can be so configured that the Lissajous scanning drive waveform is phase locked by the OCT A-scan. That way the sampling positions in each Lissajous cycle is highly repeatable. In one exemplary embodiment, the phase lock can be done by detecting the exact timing of the A-scan trigger, removing the jitter in the trigger, upsampling the trigger to generate a jitterless clock which is then used to generate the scanner drive waveform. The A-scan trigger in a swept-source OCT system can be a start-of-sweep signal or an optical feedback when the light source sweeps to a certain wavelength. Jitter removal and upsampling can be done by a phase lock loop chip, a microcontroller, etc.

To identify the spatial position of the A-scan, in one embodiment, the calibration for an ultrafast Lissajous scanning pattern involves the use of OCT imaging and an imaging sensor. The OCT imaging system can be the system which has the ultrafast Lissajous scanner. The imaging sensor can be those which are sensitive to the wavelength of the OCT system. Common OCT systems use infrared wavelengths, therefore the imaging sensor can be based on Si, InGaAs or Ge. The sensor can be a linear array, or preferably, an area array. The sensor preferably has global shutter and a short exposure time.

In one exemplary embodiment, the image sensor is so selected that the image size of the sensor is equal to or larger than the FOV of the OCT system. The image sensor is positioned in the FOV so that the OCT FOV falls into the sensor area. The image sensor is preferably positioned near the focal plane of the OCT scanning optics such that the scanning beam spot size is small in the sensor. A small spot size improves the detection accuracy of the beam position.

The exposure of the image sensor should also be synchronized with the OCT A-scan rate. The purpose is to trigger the sensor exposure at a designated position of the Lissajous trajectory. Because the exposure time is short, such a trigger mechanism allows the sensor to capture only a few OCT A-scans. These few OCT A-scans are only a fraction of the Lissajous cycle, which appears as a dotted curve with a start and an end in the imaging sensor. The coordinates of these beam spots can be used to identify the spatial position of the scanning beam when each A-scan is taken. By triggering different segments of the Lissajous pattern, a full calibration of the Lissajous pattern can be performed.

In some embodiments, the imaging depth of the OCT is at least 5 mm, 10 mm, or higher.

In some embodiments, the swept-source has a −15 dB wavelength bandwidth from about 30 nm to 200 nm. In some embodiments, the smaller the bandwidth, the lower the maximum RF frequency. However, a smaller wavelength bandwidth may result in a larger point spread function which reduces the OCT axial resolving power. Therefore, the bandwidth selected may be a tradeoff between the axial resolving power and RF signal bandwidth.

In some embodiments, the swept-source without using a buffer system has a duty cycle between 40% to 70%. In some embodiments, the higher the sweeping duty cycle, the lower the maximum RF frequency. In some embodiments, using a buffer system, as depicted in FIG. 4, further reduces the maximum RF frequency.

In some embodiments, after configuring the A-scan rate, center wavelength, sweeping bandwidth, laser sweeping duty cycle, beam steering duty cycle, and imaging depth, the RF signal bandwidth may be estimated. In some embodiments, the RF signal bandwidth is 500 MHz or higher. In some embodiments, a fast digitizer may be required, with at least 500 MHz bandwidth and 1 GS/s sample rate. In some embodiments, due to the accuracy requirement of the system, synchronization among the laser, the beam steering system, and the digitizer is critical. In some embodiments, the digitizer includes additional input ports and receives the start signals of the A-scan, B-scan, and C-scan for later 3D reconstruction.

Figure 6:
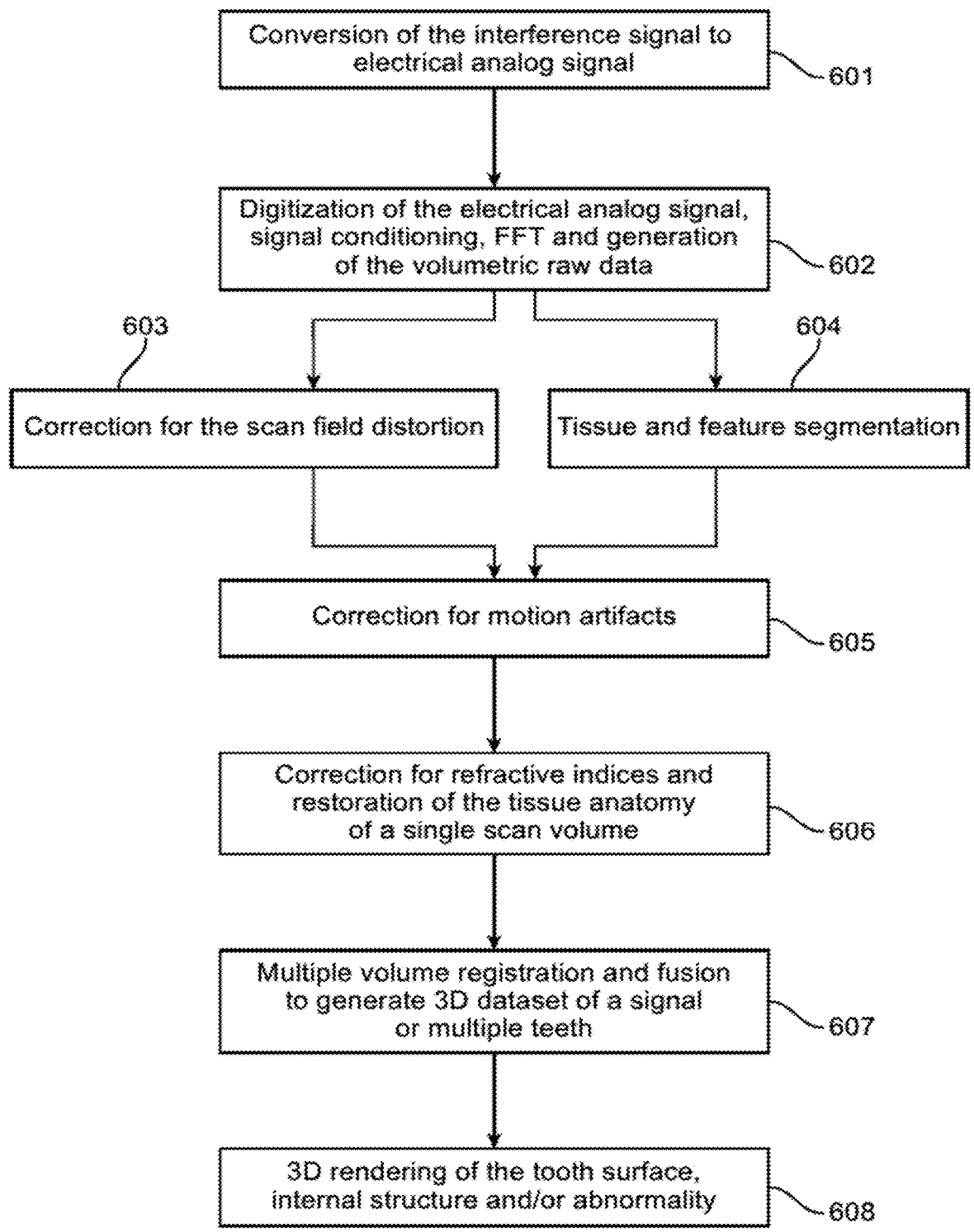
FIG. 6 depicts a data flow which consists of different acquisition, conditioning, correction, processing, and display modules, according to some embodiments.

FIG. 6 depicts an example of the data flow which consists of different acquisition, conditioning, correction, processing, and display modules. A module may be a hardware or a software subsystem. In some embodiments, the OCT system comprises a detection module 601 to convert detected photons to electrical signals for further processing. Such conversion may result in an electrical analog signal, which can then be digitized in the digitization module 602. The digitization module 602 may receive many reference, trigger, and synchronization signals from the scanning system to achieve high image quality and find the spatial distribution of the scanning pattern. In some embodiments, the swept-source OCT system may receive the wavelength sweeping temporal references to correct for wavelength sweeping non-linearity. The OCT system herein may be capable of high accuracy tooth scanning taking into account the scan beam steering pattern for accurate structural reconstruction. In some cases, the digitization module 602 may receive the start and end of scan synchronization for each beam steering axis. In some embodiments, the output of this module is the volumetric raw data.

Scan field distortion may not be ignored in most scanning systems. In some embodiments, a scan field correction module 603 uses pre-calibrated reference data to correct for the scan field distortion. In some embodiments, the scan field correction module calculates how the scan beam is steered during operation. In some embodiments, a motion artifact correction module 605 is provided. In some embodiments, the scanning probe remains stationary with respect to the teeth. In such an example, knowing the beam scanning pattern is equivalent to knowing the spatial coordinates of the tissue being scanned. Relative motion between the scanning probe and the teeth is inevitable. In some embodiments, determining the spatial coordinates of the scanned tissue takes the motion into consideration, which is the purpose of the motion artifact correction module 605.

The scan beam may be further affected if it interfaces with other objects in the scan field, which is determined by the refractive indices. In some embodiments, refractive index correction module 606 is used for determining the beam propagation path in tissue or other material. Knowing the real propagation path may be critical for the restoration of true tissue anatomy. In some embodiments, a segmentation module 604 is applied to the volumetric raw data from the digitization module 602, the motion corrected data 605, and/or to the restored data from the refractive index correction module 606. FIG. 6 depicts an example of how data may be processed, according to some embodiments. In some embodiments, the order or data flow of modules 603, 604, 605 and 606 can be configured in different ways by someone with ordinary skill in the art as long as the distortions are corrected and the tissue features are segmented.

In some embodiments, the scanning system acquires 3D data volumes continuously. In some embodiments, volumes are captured with the scanning probe in different positions and orientations. In some embodiments, registration module 607 is provided within the data processing pipeline to determine the spatial relationships of the 3D data volumes and fuse the data into a meta 3D dataset of one or multiple teeth. In some embodiments, a display module 608 is used to visualize the information that can be used for decision making.

In some embodiments, motion correction module 605 obtains motion information of the scanning probe and/or the patient to correct for the image distortion introduced by such motions during imaging. In some embodiments, such motion is termed bulk motion. In some embodiments, because the OCT system uses scanning technology, there is a time delay from one scan point to the next, however small it might be. In some embodiments, the bulk motion is the relative motion between the scanning probe and the target teeth (linear and/or angular) during this time delay. In some embodiments, this bulk motion may introduce an error to the orientation and/or the position of the next scan point with respect to the current scan point. In other words, the orientation and/or the position of the next scan point may not be solely determined by the beam steering module.

In some embodiments, the bulk motion information includes the orientation, position, linear or angular velocity, linear or angular acceleration, etc. It may be obtained by ways of the motion tracking devices, e.g., the inertial measurement unit (IMU), accelerometer, gyroscope, magnetometer, electromagnetic navigation system, optical navigation system, etc. In some embodiments, correction for such errors is accomplished by obtaining the motion information from the tracking devices, combining the bulk motion with the motion caused by the beam steering module 501 (which can be calibrated and deterministic) to calculate the true positions and orientations. In some embodiments, the goal for the correction of the motion artifacts is to correct the bulk motion that occurs in the volumetric scan data, which has a scan data coordinate system. In some embodiments, the motion tracking devices bulk motion information within its own device coordinate system. In some embodiments, there can be a calibration during manufacturing or field service to obtain the transformation matrix from the device coordinate system to the scan data coordinate system.

In some embodiments, such correction can be done on each A-scan, B-scan or even C-scan, depending on the acceptable error specifications. In some embodiments, if the expected bulk motion is fast enough such that the motion artifacts in neighboring A-scans become unacceptable, motion correction for each A-scan is desired. In some embodiments, there is a scanner system using a dual galvo mirror beam steering system. In some embodiments, the motion tracking system obtains the change in position $\Delta P$ and orientation $\Delta \Theta$ for one B-scan. $\Delta P$ and $\Delta \Theta$ are vectors. Assuming the B-scan consists of n A-scans. The bulk motion correction for each A-scan can be written as follows:

$$A\text{-scan}\#1:=\Delta P/n; \Delta\Theta/n$$

$$A\text{-scan}\#2=2*\Delta P/n; 2*\Delta\Theta/n$$

$$A\text{-scan}\#3=3*\Delta P/n; 3*\Delta\Theta/n \ldots$$

In some embodiments, the expected bulk motion is slow such that the motion artifact within a B-scan may be acceptable, motion correction may be on for each B-scan, assuming the motion for all A-scans in the same B-scans are the same. In some embodiments, the motion correction module 605 may analyze the motion information from the motion tracking devices and determine whether there is significant motion. In some embodiments, if the motion is tolerable, e.g., all data points have linear motion errors of less than 100 µm, preferably less than 20 µm, the module may choose not to perform motion correction.

In some embodiments, the system may incorporate a video camera, which can be used for motion tracking. A variety of video motion tracking technologies may apply, e.g., the block-matching algorithm, contour tracking algorithm, cross-correlation, optical flow, feature based method, etc.

Figure 7:
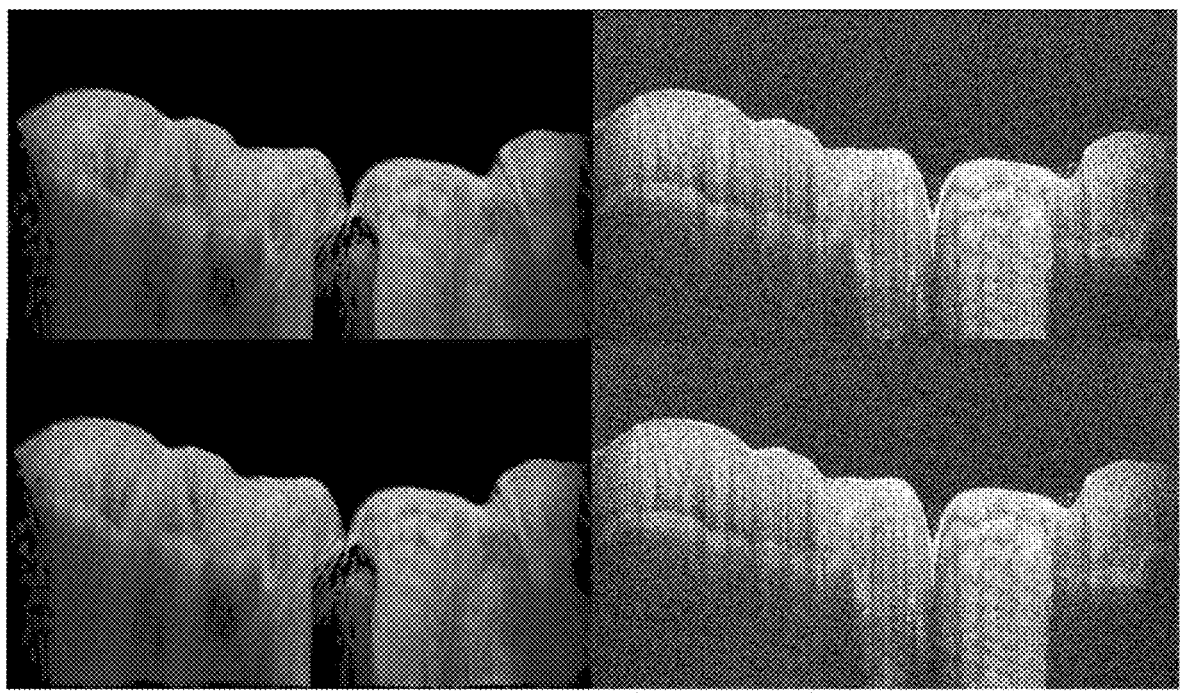
FIG. 7 depicts exemplary reconstruction results from the raw OCT scans, according to some embodiments.

In some embodiments, the OCT volumetric data set may be used for motion tracking by matching the consecutive surface topographies of the object being scanned. The surface topography may be extracted using various detection algorithms. Assuming that the topographies overlap partially, various surface matching algorithms may be used to track the motion, e.g., the Iterative Closest Points, Coherent Point Drift, Normal Distribution Transformation, and their variations, etc. In some embodiments, such surface matching algorithms can be applied to a subset of each volume, The index of refraction in enamel has been estimated to be close to 1.6, or similar to that of glass. When light beams, including laser beams, enter the enamel region, some of the rays may refract into different directions instead of staying parallel. They may also become shorter with a higher refractive index. In some embodiments, the OCT sensor will take the returned laser beams and reconstruct the resulting scan image with the assumption that the beam remained straight. In some embodiments, to correct for this, we first use computer vision algorithms to detect the enamel surface. In some embodiments, these algorithms are detailed in registration module 607. In some embodiments, for each A-line, the portion underneath the enamel surface is rescaled to be accurate with respect to the ray shortening effect. In some embodiments, plane normals are calculated at each point on the enamel surface, and a local slope is calculated using surrounding points. In some embodiments, 3D Snell's law is used to calculate the ray direction from the enamel surface. In some embodiments, the image section underneath the enamel is rotated in the appropriate direction as found by the ray tracing as described. FIG. 7 depicts an exemplary reconstruction result from the raw OCT scans, according to some embodiments. The raw scans are on the left, and the reconstructed scans are on the right.

Figure 8:
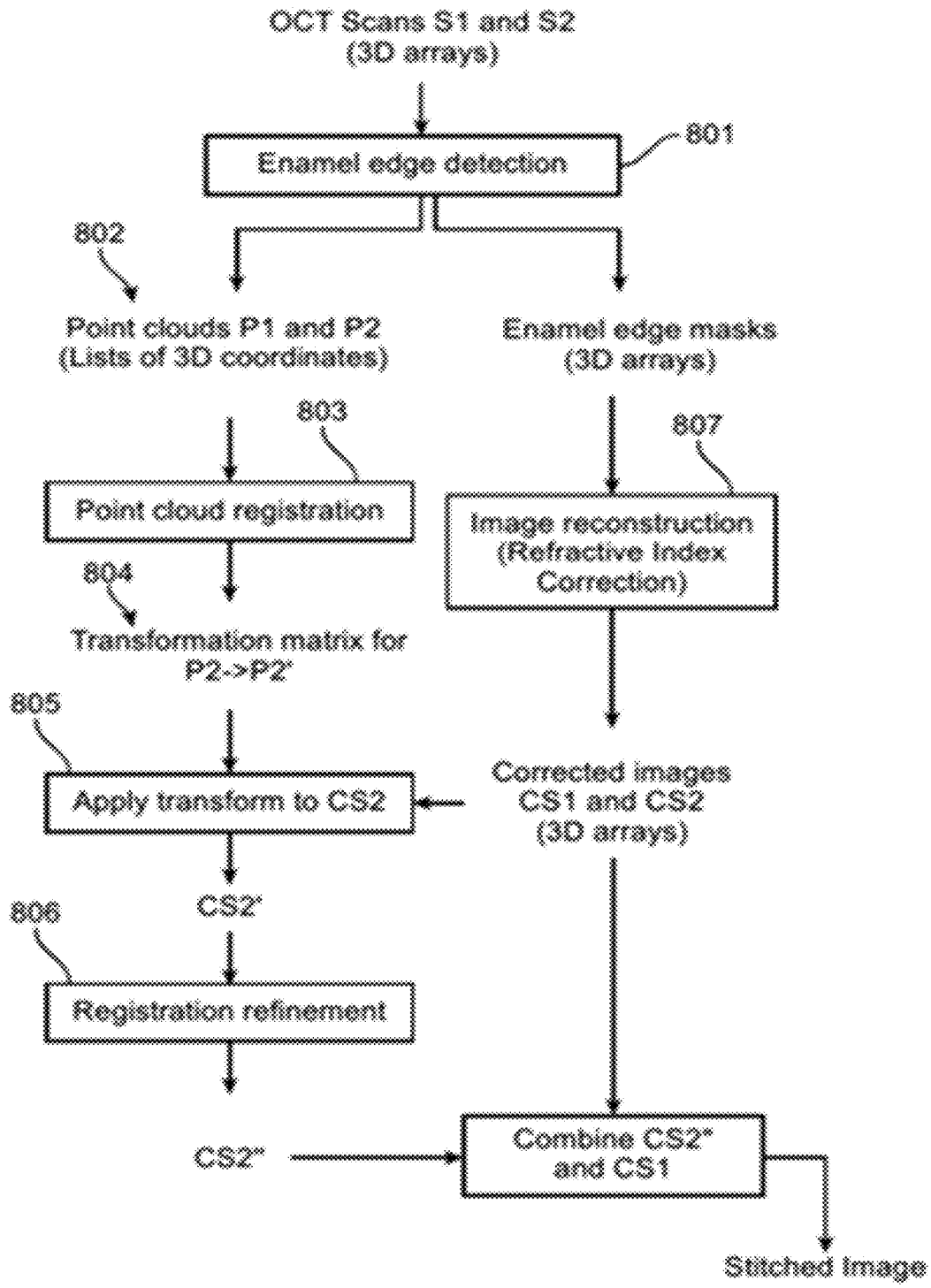
FIG. 8 depicts a stitching and fusion process; according to some embodiments.

FIG. 8 depicts an exemplary embodiment of the stitching and fusion module 607. In some embodiments, the topography of the tissue surface on which the sample beam is first incident upon, e.g., the enamel edge, may be utilized for volume stitching, because prior to the incidence, the light travels in air with no image distortion caused by the imaging subject. In some embodiments, the enamel edge 801 can be detected by finding the locations with the strongest back-scattering or the greatest gradient of back-scattering, or by using one of the many Convolutional Neural Network methods for tissue boundary classification, etc.

Assuming that the topographies from two neighboring scan volumes overlap partially, various algorithms may be used to determine the overlapping region. For instance, the topography may be represented by a 3D point cloud (802 of FIG. 8), triangle mesh, or any other 3D rendering technique. Examples of point cloud registration 803 techniques may include Iterative Closest Point, Coherent Point Drift, and Normal Distribution Transformation. The optimal criterion of matching the two topographies within the overlapping region, as termed the objective function, may be the mean squared error, mean absolute error, etc. An initial matching of the two-point clouds may be proposed as the start of the algorithm. In some embodiments, the initial matching is facilitated by using a motion tracking device to estimate the movement of the scanning device. In some embodiments, optical flow or other keypoint based methods are used to estimate movement as the initial matching.

The variables for optimization may be linear translations and rotations of the coordinates in the two volumes, or even a non-rigid coordinate transformation to compensate for the hand motion artifact. The optimization may be done using exhaustive searching, gradient descent, stochastic gradient descent, etc. In some embodiments, constraints are added to the variables to avoid overfitting. One example is the maximum number of linear translations or rotations that can occur between two consecutive scan volumes. Other constraints may include the number of iterations of optimization, introduction of regularization terms in the objective function, a stop threshold for the objective function, etc.

In some embodiments, the matching is accomplished when one determines the transform matrix 804 (in FIG. 8) of the two coordinate systems of the topography. In some embodiments, the stitching algorithm is implemented such that stitching neighboring volumes in real time is achieved. In some embodiments, this stitching problem, partially or as a whole, can be resolved by a machine learning approach, including a deep-learning approach. For example, for deformable registration, deep learning, or other computer vision methods such as optical flow can be used to find local warp fields for images, as can non-machine learning methods. Deformable registration may be useful after the initial stitching proposal to account for small discrepancies in the scan due to noise or movement, and in order to align features that are internal to the tooth structure.

In some embodiments, the transformation matrix is applied to the 3D data 805. In some embodiments, refinement 806 is done, such as removing outliers and applying deformable registration under constraints. In some embodiments, correction for refractive index 807 is done before the two scan volumes are combined together. FIG. 9B demonstrates the result of such a combination.

Figure 10:
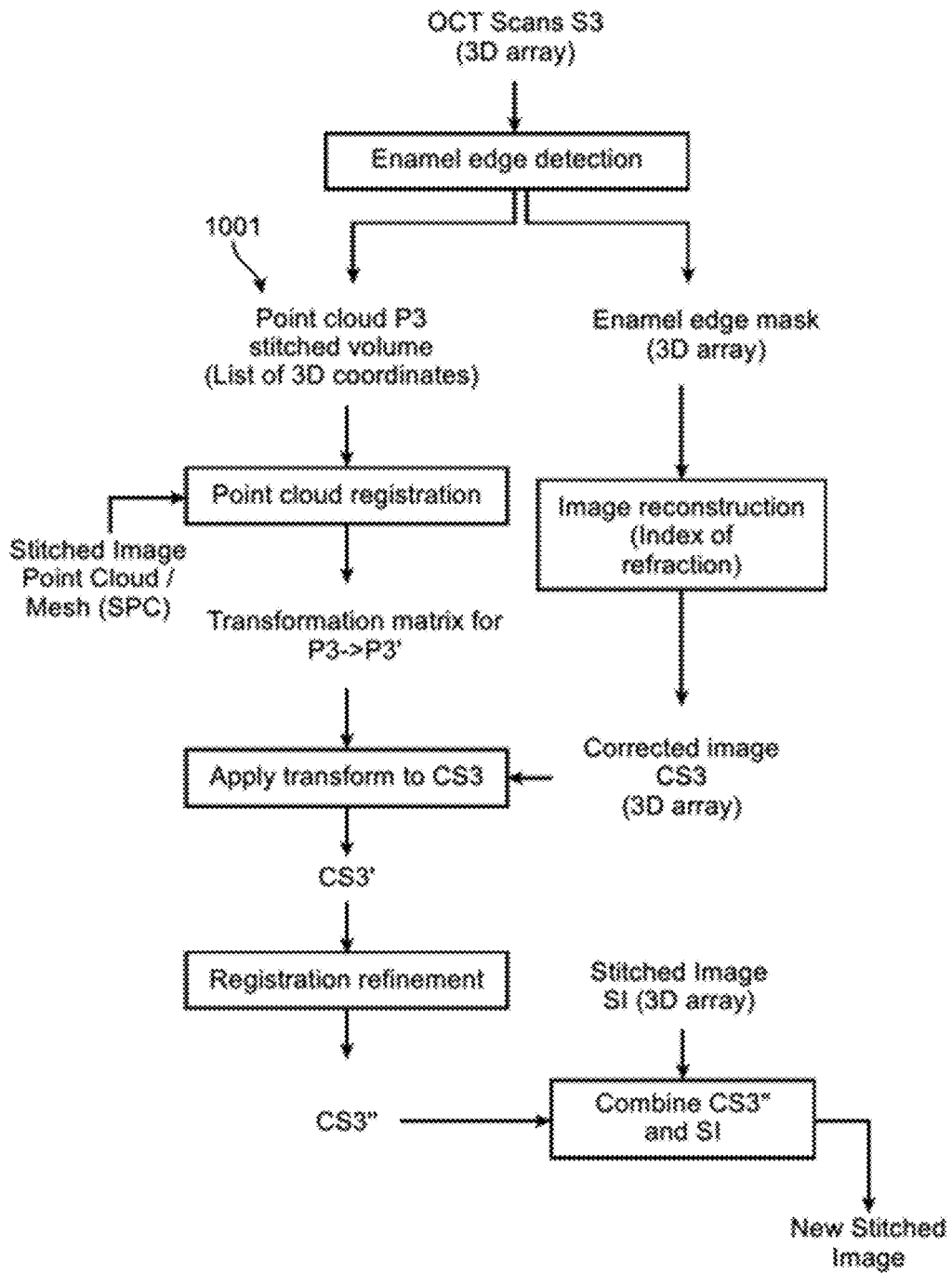
FIG. 10 depicts stitching additional volume data to an existing stitched volume data set, according to some embodiments.

FIG. 10 depicts stitching additional volume data to an existing stitched volume data set, according to some embodiments. In some embodiments, the modification to the algorithm, as compared to FIG. 8, is the volume data, which is used for point cloud registration, which are the point cloud P3 to be stitched, and the volume which combines the previously stitched volumes.

Figure 11:
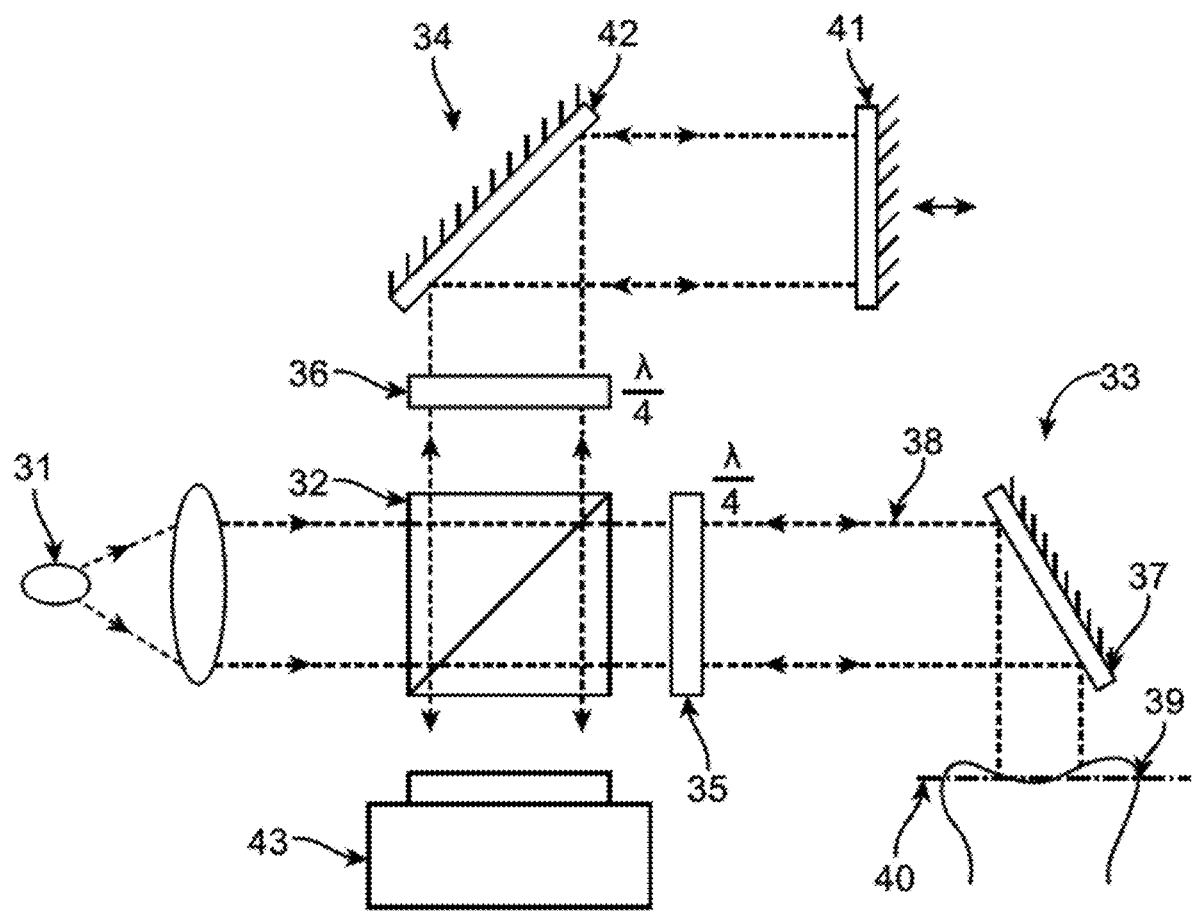
FIG. 11 depicts an intraoral scanner with a full-field OCT configuration, according to some embodiments.
Figure 12:
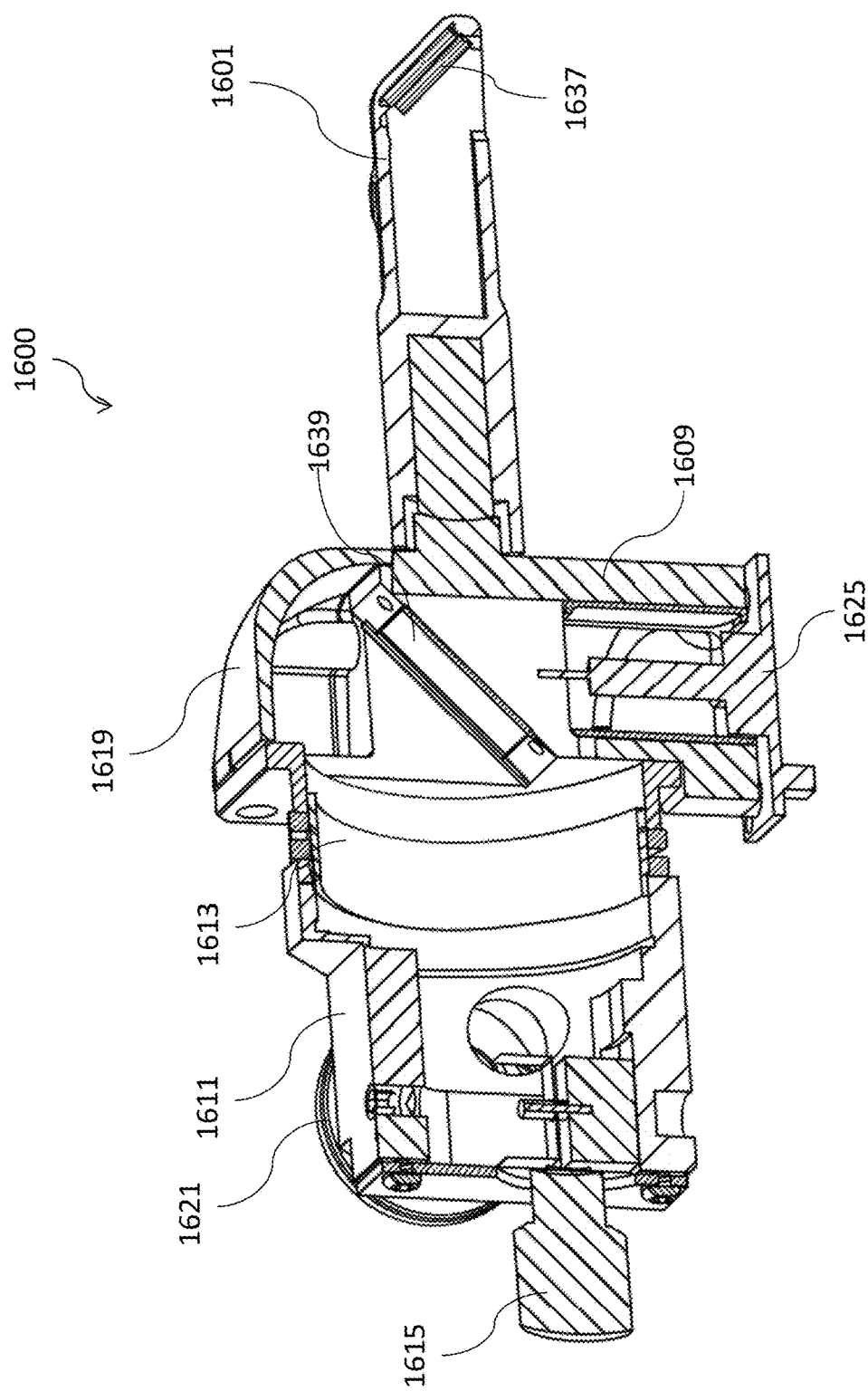
FIGS. 12-18 depict a scanning probe, according to some embodiments.
Figure 13:
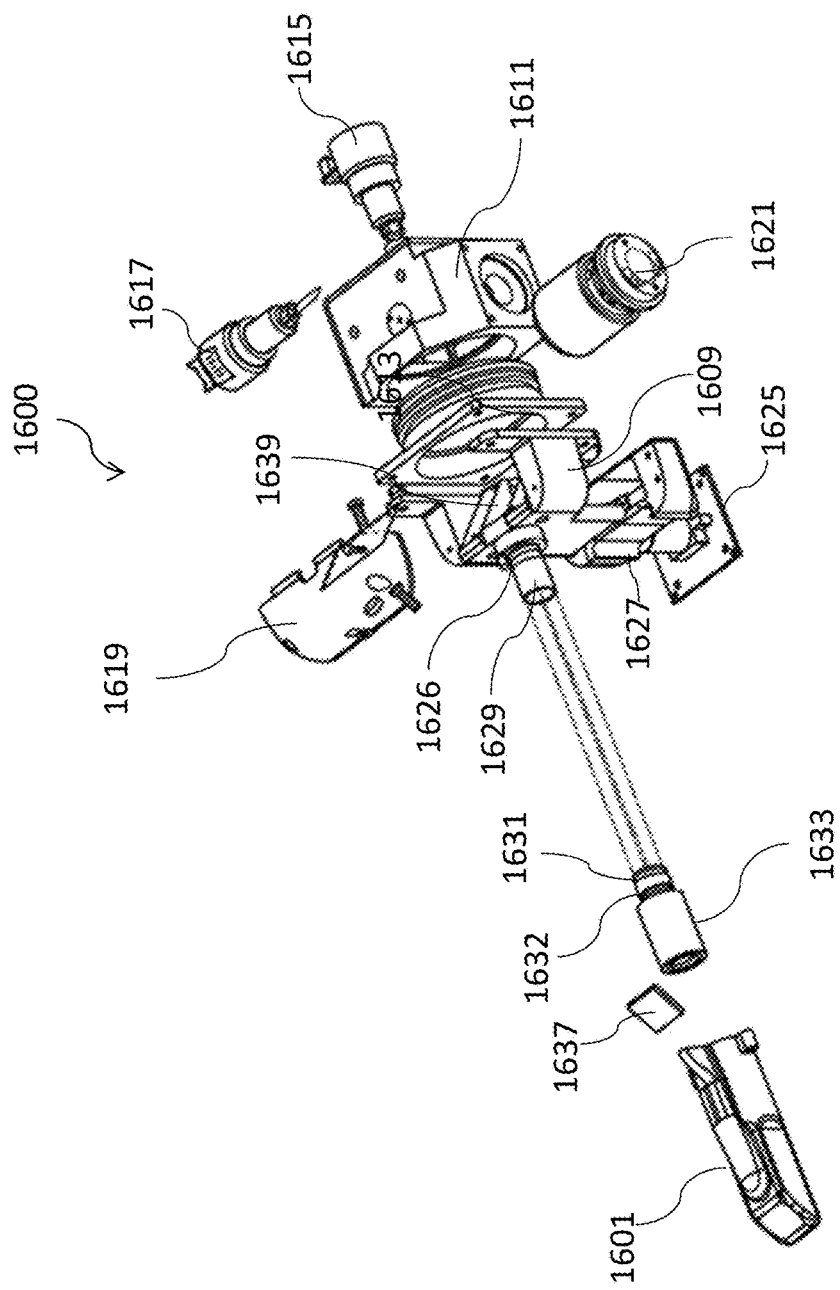
Figure 14:
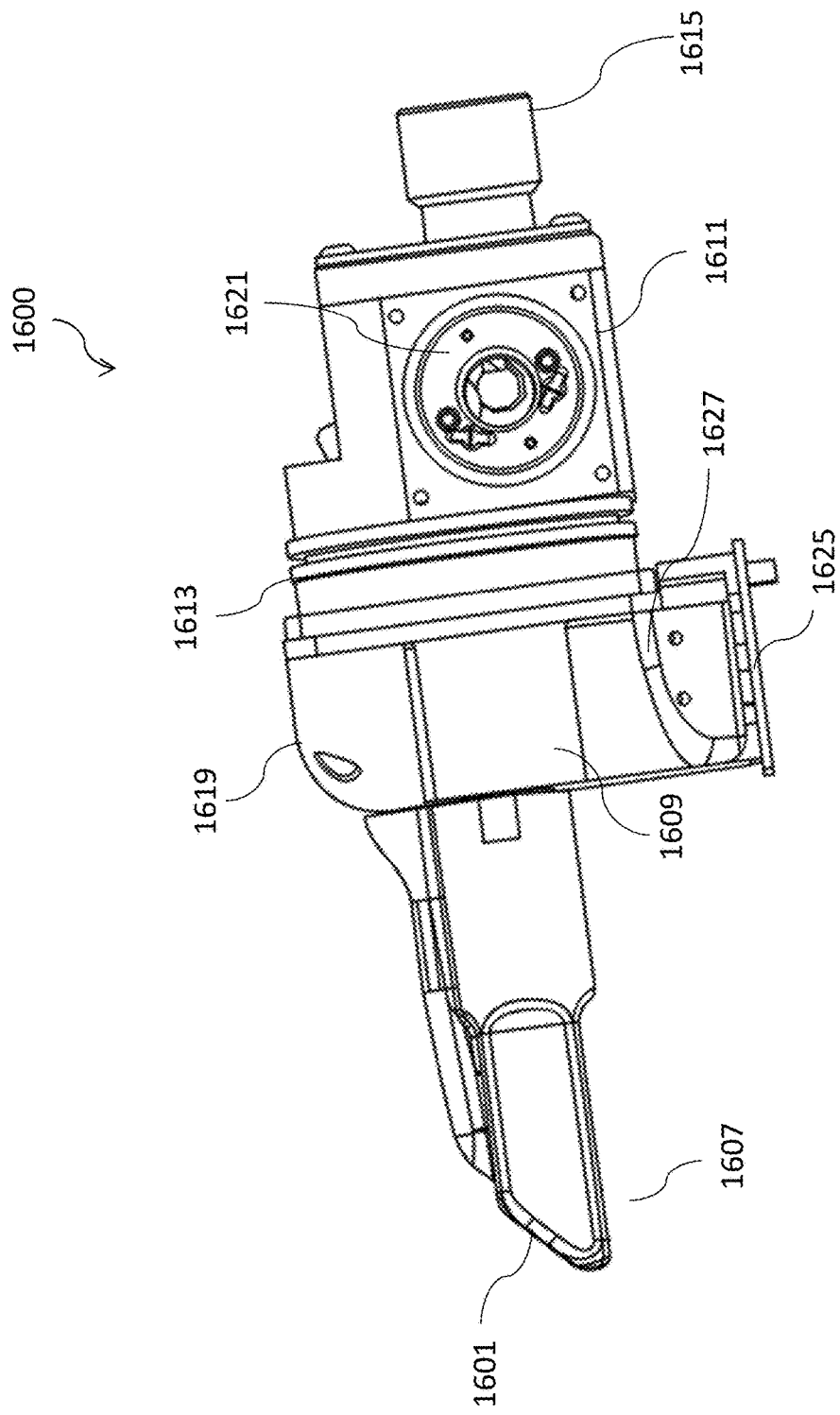
Figure 15:
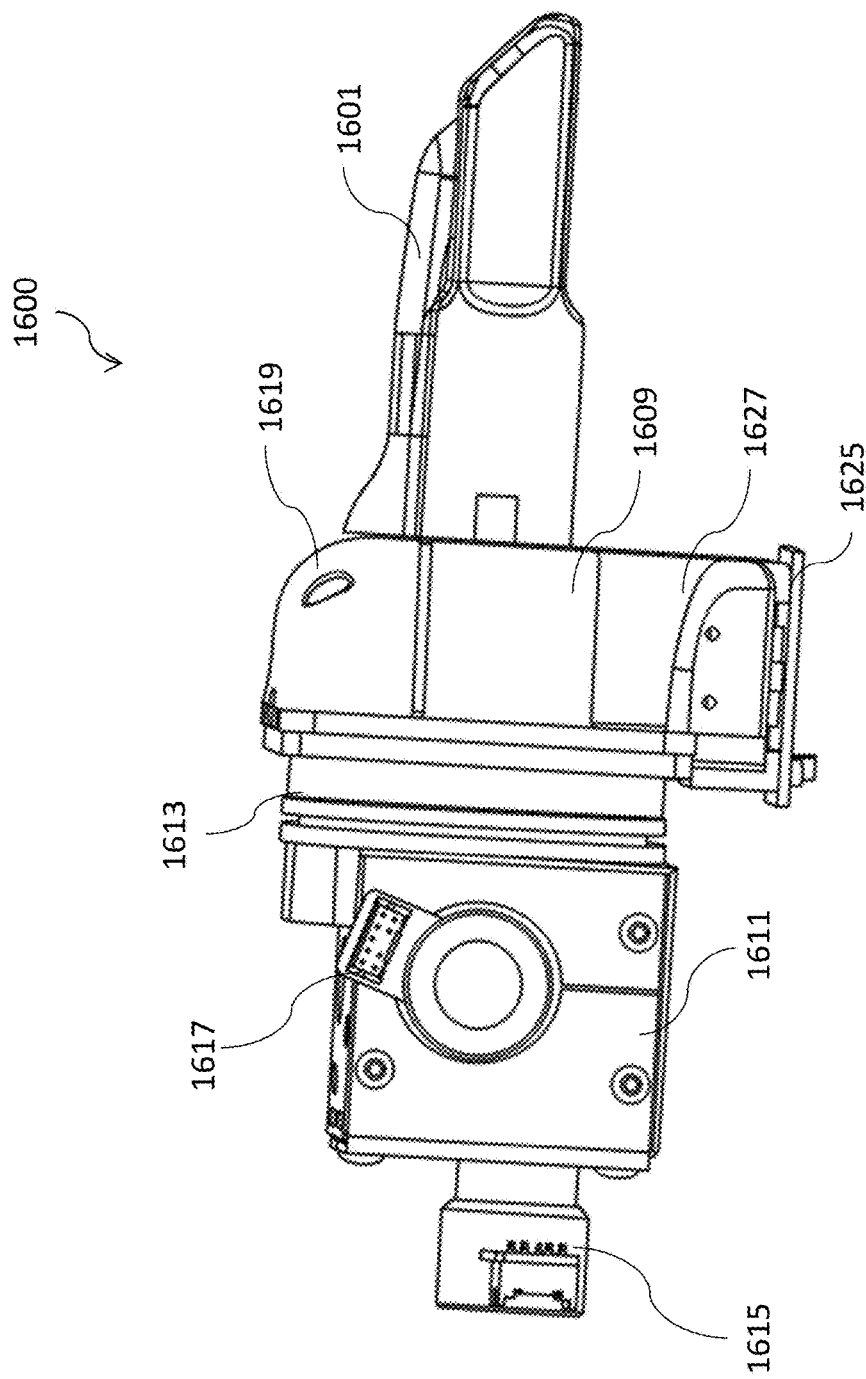
Figure 16:
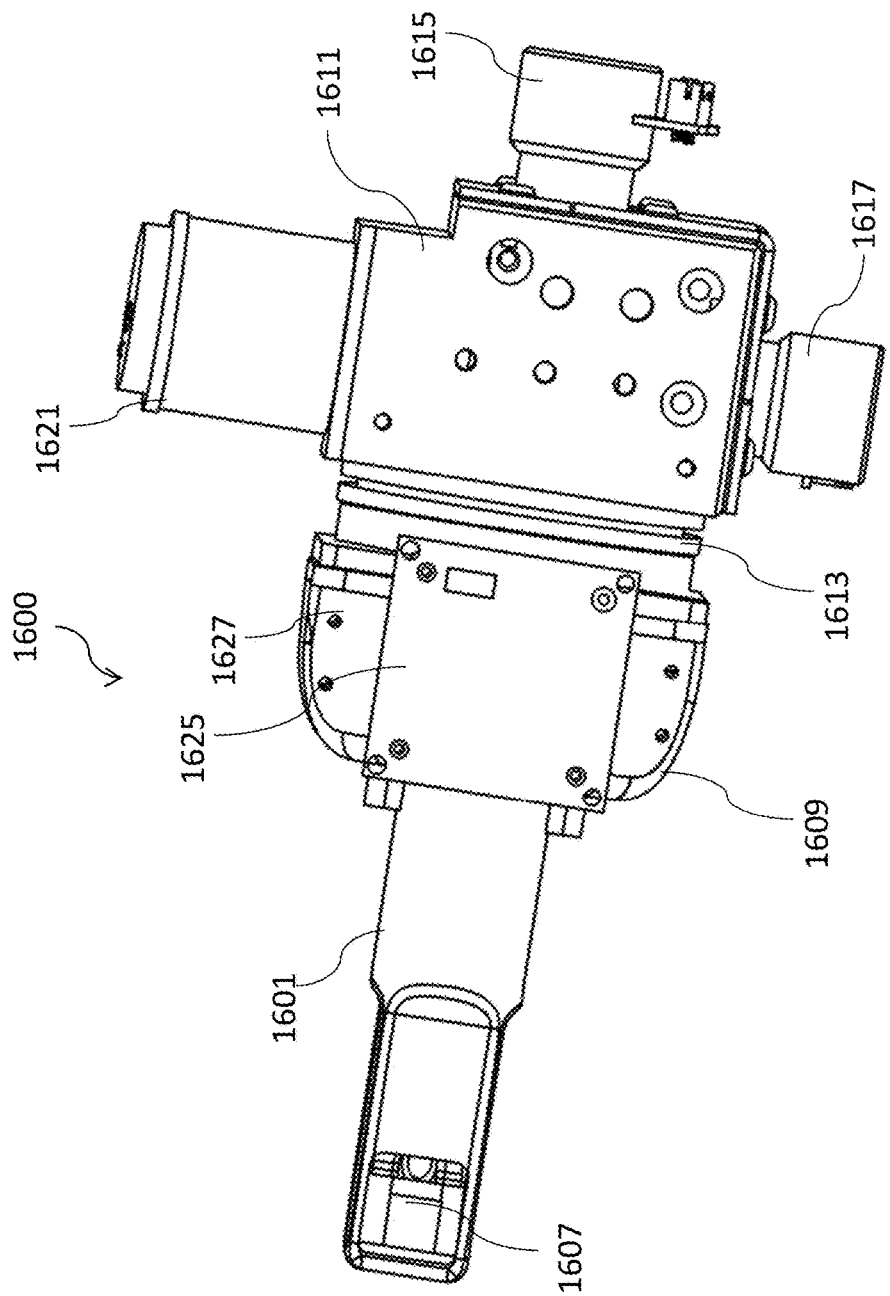
Figure 17:
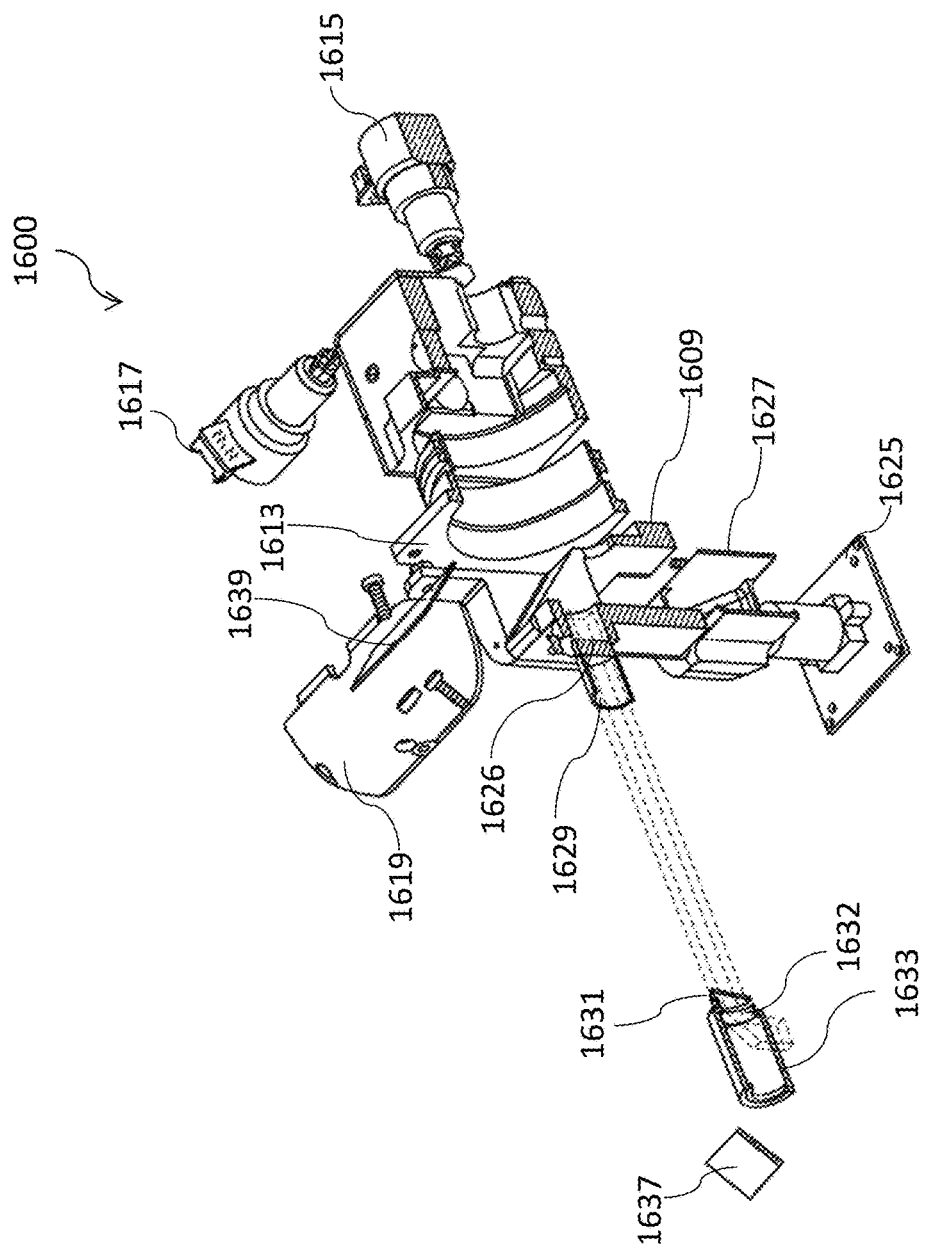
Figure 18:
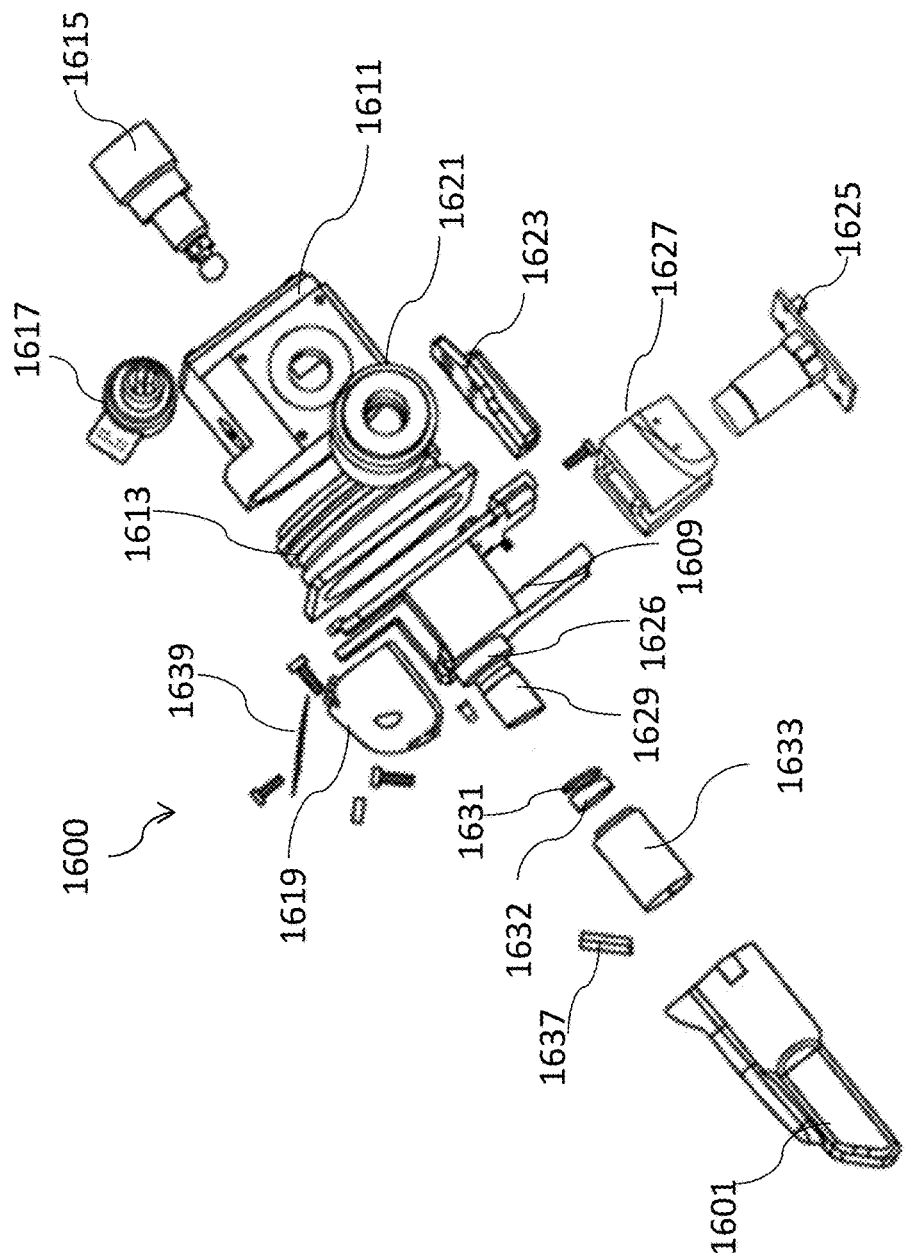

In some embodiments, the OCT system can be configured in other architectures, e.g., time-domain OCT, spectral-domain OCT, full-field OCT, line field OCT, etc. FIG. 11 depicts an intraoral scanner with a full-field OCT configuration, according to some embodiments.

In some embodiments, the beam from the light source 31 is collimated before entering the beam splitter 32 where the beam is split into the sample arm 33 and the reference arm 34. In some embodiments, the beam splitter 32 may be a polarizing beam splitter in conjunction with two quarter wave plates 35 and 36 in the two arms for a higher collection efficiency. In some embodiments, a mirror 37 in the sample arm reflects the probing beam 38 towards the subject of interest 39.

In some embodiments, the mirror 41 in the reference arm is installed onto a motorized linear translational stage. In some embodiments, by varying the position of the stage along the beam propagation direction, one can change the imaging plane 40 in the sample arm and thus establish the optical sectioning. In some embodiments, by stepping the reference arm mirror 41 through a predefined range, one can achieve the volumetric imaging of the subject. Another mirror 42 or mirrors may be used to bend the reference beam to reduce the spatial extension of the open air configuration. In some embodiments, the beams reflected from the two arms are recombined and interfered at the beam splitter 32. In some embodiments, a 2D camera 43 is used to convert the optical signal into the electrical signal. The post-processing of this spatial coherence OCT signal may be similar to that of the temporal coherence OCT.

In some embodiments, one of the advantages of the spatial coherence OCT is that the optical sectioning is captured in a snapshot, therefore minimizing in-frame motion artifacts, while the temporal coherence OCT may have more noticeable motion artifacts in the en-face plane. The open air configuration of the spatial coherence OCT may be larger in size and have a lower signal-to-noise ratio.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying, or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

I. Exemplary Embodiments

FIGS. 11-18 depict an exemplary embodiment of the scanning probe 1600. In some embodiments, the scanning probe 1600 comprises a galvanometer optical scanner mount (galvo mount) 1611 at a proximal end of the scanning probe. In some embodiments, the galvo mount receives a first galvo scanner 1615 and second galvo scanner 1617. In some embodiments, the galvo mount 1611 further comprises a kinetic mount 1621. In some embodiments, the kinetic mount 1611 allows the scanning probe to be mounted to a robotic arm. In some embodiments, the kinetic mount 1611 allows the scanning probe to be mounted to handle to provide a handheld OCT scanning system as described herein. In some embodiments, the galvo mount 1611 comprises at least one galvo mirror. In some embodiments, the galvo mount 1611, first galvo scanner 1615, second galvo scanner 1671, and at least one galvo mirror is referred to herein as a beam steering module. In some embodiments, a sample arm light is collimated and guided into a beam steering module. The beam steering module may have two mirrors as the beam reflecting elements. In some embodiments, the mirrors are mounted on oscillating components such as two galvo motors, which form a galvo mirror subsystem. The galvo mirror subsystem can be used for its deterministic motion feedback and control, and the scanning linearity, which may be desirable for simplified data reconstruction in later processing stages. The oscillating axes of the two mirrors may be perpendicular for easy position control, so that one mirror controls the beam sweeping across one direction and the other mirror controls the orthogonal direction. In some embodiments, the galvo mirror subsystem is configured to scan as fast as possible, but also has minimum scan field distortion and high repeatability. Therefore, the subsystem may be configured to scan unidirectionally, and use only the linearly scanning portion.

In some embodiments, the beam steered by the galvo mirror subsystem is then refocused by a lens 1626, reflected by a mirror 1637, and exits through an imaging window 1607. In some embodiments, a transparent window is installed to prevent contamination of the lens system.

In some embodiments, the galvo mount 1611 is coupled to aligner 1609 via adapter 1613. In some embodiments, the aligner houses a dichroic mirror 1639. In some embodiments, a video camera 1625 couples to the aligner 1609. In some embodiments, the dichroic mirror 504 is configured to transmit OCT light and reflect visible light. In some embodiments, the visible light is reflected or scattered by the tooth and redirected to the camera 1625. In some embodiments, a camera lens system 1627 is provided for the camera 1625 and attaches to aligner 1609. In some embodiments, the camera lens system 1627 is configured to match the focal plane and the depth of focus of the OCT beam profile. In some embodiments, the aligner 1609 further comprises a cover 1619. The cover 1699 may facilitate access to the dichroic mirror 1639 housed within the aligner 1609. In some embodiments, lens 1626 is coupled to the aligner. In some embodiments, the OCT lens system comprises lens 1626, first angle spacer 1629, window 1631, second angle spacer 1632, and lens tube 1633. In some embodiments, the lens tube 1633 houses the components of the OCT lens system.

In some embodiments, sleeve 1601 is provided at a distal end of the scanning probe 1600. In some embodiments, the sleeve 1601 couples to the aligner and houses the OCT lens system components. In some embodiments, the sleeve 1601 comprises a mirror 1637 to direct the sample arm through the imaging window 1607. In some embodiments, the imaging window comprises a transparent cover to prevent contamination of the lens system.

In an aspect, the present disclosure provides optical coherence tomography scanning systems that perform fast, sparse scans and stitch together multiple such scans to yield dense images. As described above, conventional OCT scanning technology may have limitations that restrict its use in dentistry, such as limited penetration depth, a small field of view (FOV) that prevents full arch imaging, a long capture time that can cause motion distortion within a single volume, and a need for complex registration to achieve surface trueness required of an intraoral scanner (IOS) or to guide automated tooth preparation surgery. The present disclosure may address the above limitations by providing improved OCT scanning systems and methods. For instance, OCT scanners according to the present disclosure may beneficially avoid unacceptable amounts of motion blur by traversing their respective scan patterns quickly, typically completing an entire two-dimensional frame faster than a conventional raster scanner completes one raster line segment. In order to traverse their scan patterns quickly, systems and methods herein may provide a sparse sampling method by reducing the number of A-scans per length of scan pattern. For instance, fewer A-scans per length of scan pattern may be taken compared to conventional OCT scanners as described above. To compensate for the sparsity of the sample points along their respective scan line segments, and for gaps between respective line segments of the trajectory, these embodiments acquire and combine several partially overlapping frames for each study.

Optical coherence tomography (OCT) is an imaging technique that uses low-coherence, typically near-infrared, light to capture micrometer-resolution, two- and three-dimensional images from within optical scattering media, such as biological tissue. OCT is based on low-coherence interferometry. In conventional interferometry with long coherence length, i.e., laser interferometry, interference of light occurs over a distance of meters. However, in OCT, this interference is shortened to a distance of micrometers, due to the use of broad-bandwidth light sources, i.e., sources that emit light over broad ranges of wavelengths, such as superluminescent diodes and lasers with extremely short pulses (femtosecond lasers).

Figure 19:
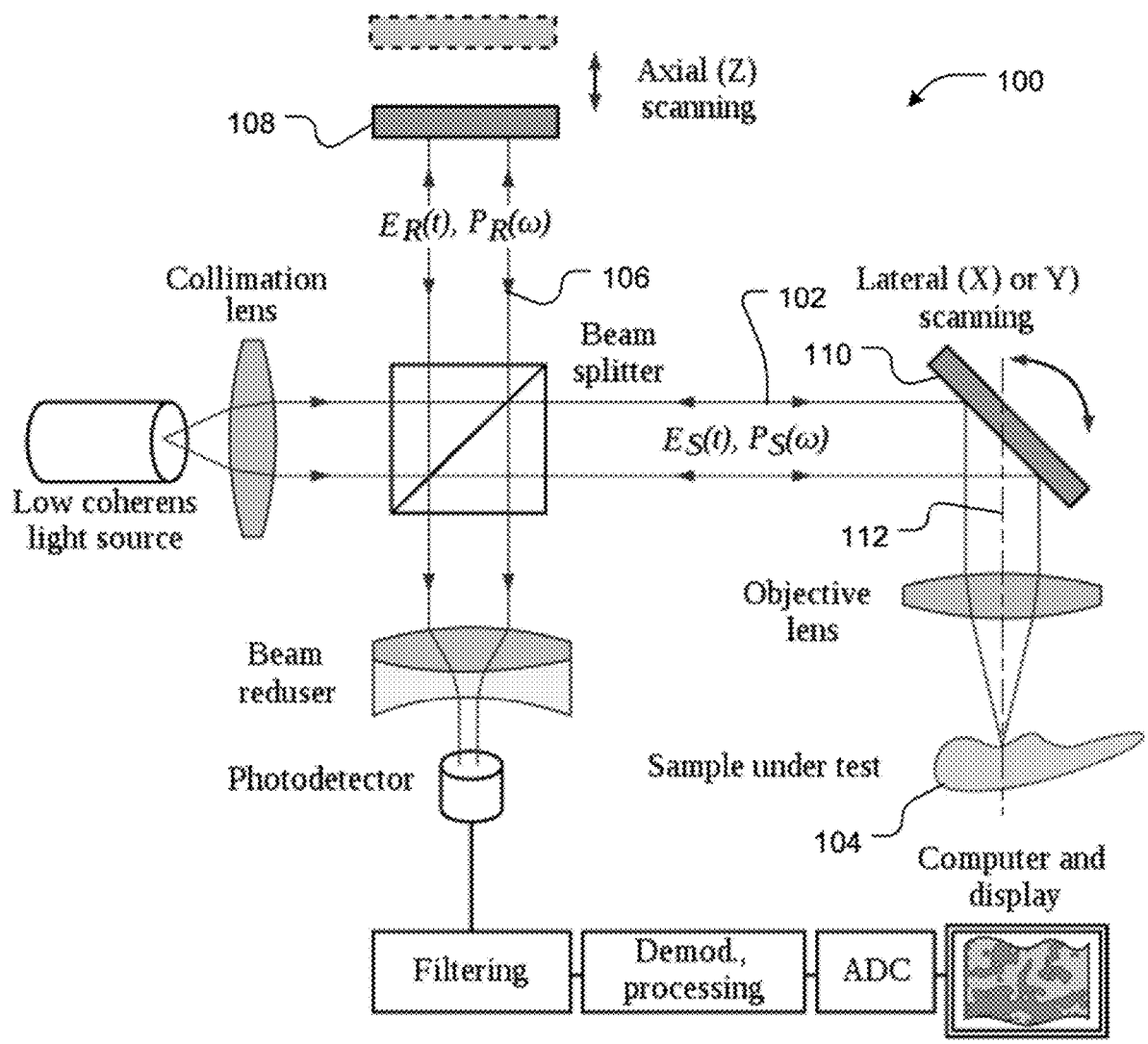
FIG. 19 is a schematic block of an optical coherence tomography system, according to the prior art.

FIG. 19 is a schematic block of an optical coherence tomography system 100, according to the prior art. Light in the OCT system 100 is broken into two arms: a sample arm 102 containing an item under test 104, and a reference arm 106, usually containing a mirror 108. A combination of reflected light from the sample arm 102 and reference light from the reference arm 106 gives rise to an interference pattern, but only if the light from both arms 102 and 106 have traveled equal optical distances, i.e., distances that differ by less than a coherence length of the light. By scanning the mirror 108 in the reference arm 106, a reflectivity profile of various depths of the item 104 can be obtained. The amount of interference is proportional to the amount of reflected light, which enables distinguishing portions of the item under test 104 having different reflectivity characteristics at different depths. Any light that is outside the short coherence length does not interfere, enabling the OCT to interrogate specific depths of the item under test 104 and produce the reflectivity profile. The reflectivity profile, called an A-scan, contains information about spatial dimensions and structures within the item of interest. An A-scan (axial or depth scan) represents data recovered from various depths of a single "hole" conceptually drilled into the item under test 104.

Figure 20:
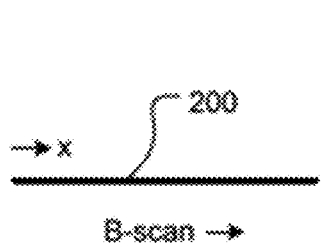
FIG. 20 illustrates a line segment on a surface of an item under test, according to the prior art.

A cross-sectional tomogram (B-scan) may be achieved by laterally combining a series of these axial depth scans (A-scans) or scanning a mirror 110 in the sample arm 102. For example, scanning the mirror 110 in one dimension moves the light of the sample arm 102, so as to project the light onto progressive points along a line segment (as viewed down the sample arm 102 axis 112) on a surface of the item under test 104. Line 200 in FIG. 20 illustrates the line segment on the surface of the item under test 104. Modern OCT systems sample individual points along the line 200, yielding individual pixels (not shown) along the line 200.

Figure 21:
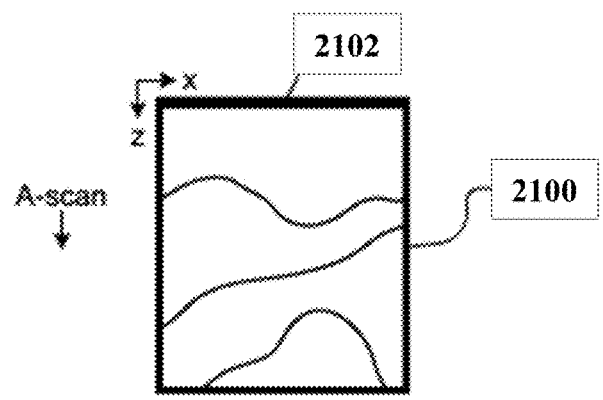
FIG. 21 illustrates an exemplary combination of multiple A-scans along a B-scan to produce a two-dimensional reflectivity profile, according to the prior art.

An OCT system can combine multiple A-scans along a B-scan to produce a two-dimensional reflectivity profile, for example as illustrated at 2100 in FIG. 21. The plane of two-dimensional reflectivity profile 2100 represents a "slice" taken through the item under test 104. The top line 2102 (shown in heavy line) of the two-dimensional reflectivity profile 2100 of FIG. 3 corresponds to the line 200 in FIG. 20.

Figure 22:
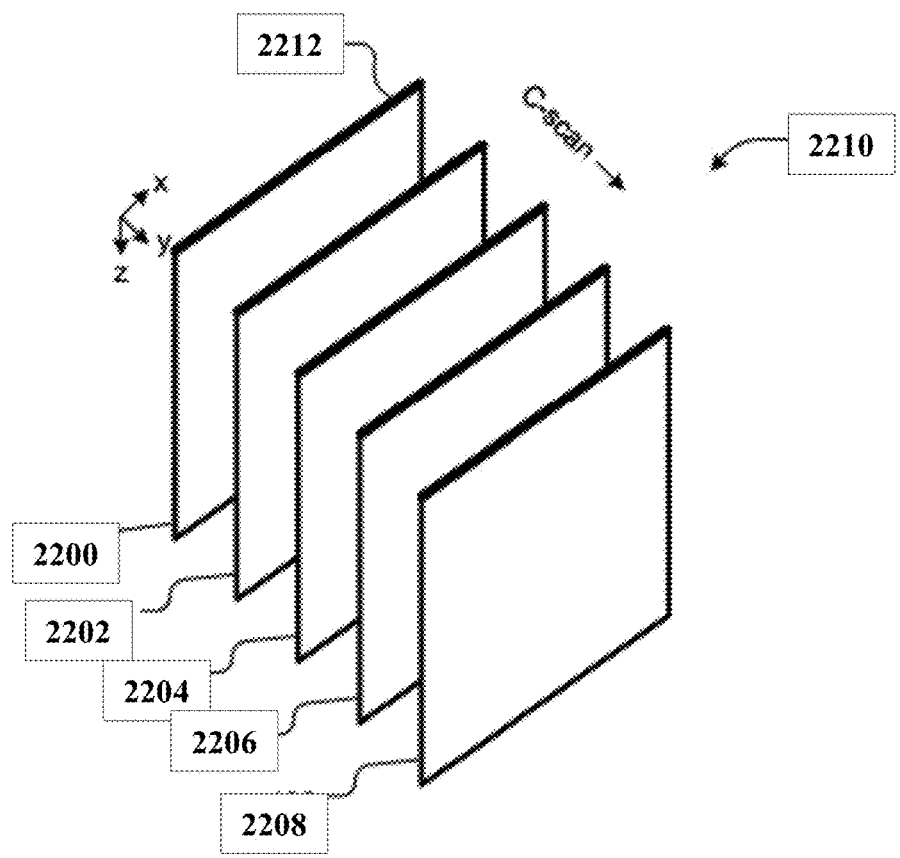
FIG. 22 illustrates an exemplary combination of multiple A/B scans along a C-scan to produce a three-dimensional reflectivity profile using a raster scan, according to the prior art.

An OCT system can combine multiple A/B scans, for example as represented by scans 2200, 2202, 2204, 2206, and 2208 in FIG. 22, to produce a three-dimensional reflectivity profile 2210. Top heavy lines in FIG. 22, represented by heavy line 2212, correspond to line 2100 in FIG. 21 and line 200 in FIG. 20.

Figure 23:
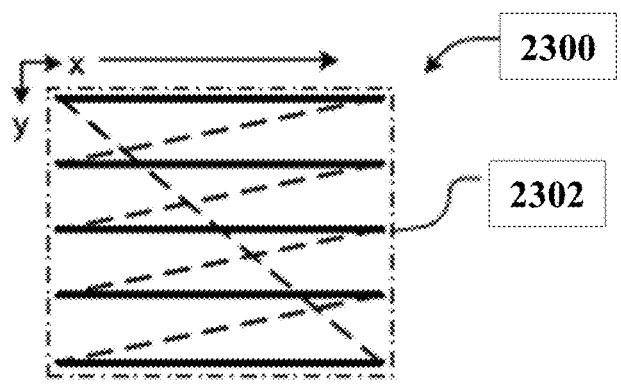
FIG. 23 illustrates a conventional raster, according to the prior art.

A conventional approach to performing a combined B/C scan is to cause the reference arm light beam to be projected toward the item under test 104 onto progressive points along a raster 2300, as illustrated in FIG. 23. A raster is characterized by a plurality of parallel, spaced-apart scan line segments. FIG. 23 illustrates retrace line segments in dashed line and a direction of scan by an arrow. However, depending on how the light of the reference arm is redirected, the raster may have no retrace line segments. For example, two rotating polygon mirrors can produce a raster without a retrace.

One complete raster scan, i.e., one traversal of a pattern, like the one shown in FIG. 23, is referred to as a frame. A region generally covered by one traversal of the pattern is referred to as being outlined by a two-dimensional scan area outer boundary or bounding box, as exemplified by two-dimensional scan area outer boundary 2302.

Figure 24:
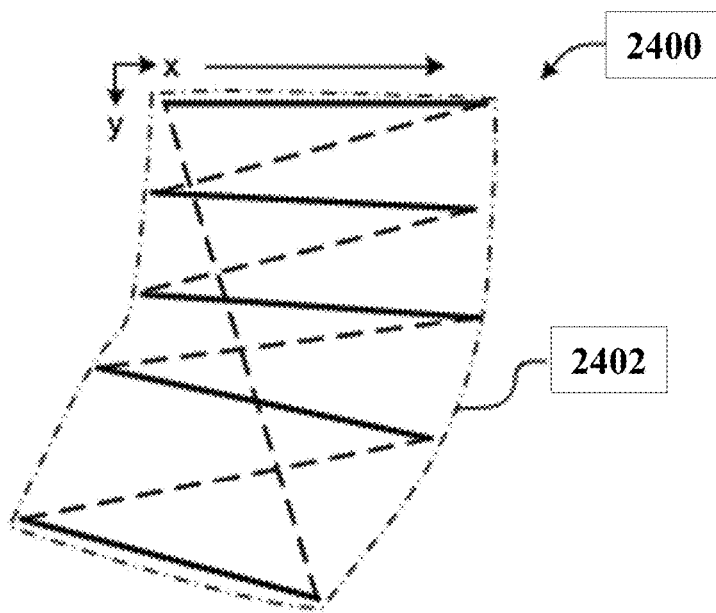
FIG. 24 illustrates a problem (motion blur) conventional raster scans exhibit, due to movement of a scanning wand during a frame, according to the prior art.

Unfortunately, conventional intraoral OCT scanning methods and apparatus are too slow, particularly for handheld scanning wands. A conventional single-frame raster scan would take on the order of several seconds to complete, during which time the system would experience an unacceptable amount of motion blur due to unintended movement of a hand of a human operator. For instance, in the exemplary scanning pattern 2400 as illustrated in FIG. 24, unintended movement of a scanning wand could result in: uneven spacing between successive raster line segments, x and/or y distortion of the raster pattern leading to x and/or y distortion of the two-dimensional scan area outer boundary 2402, and curvature (not shown) of individual raster line segments. Furthermore, it is impossible to estimate an extent of the motion blur, because a single raster pattern has no sample point where two raster lines cross. Therefore, no common reference points exist, where two raster line segments interrogate the same point on an item under test and can, therefore, be used to detect or measure the unintended movement. Some prior art systems include an additional camera to detect the unintended movement, but such systems are big, expensive, and awkward to use.

A conventional OCT scan frame typically covers too small an area to completely image a large tooth or a relatively large portion of a mouth. Consequently, multiple OCT scan frames may need to be combined to form a single image of item(s) under test. However, holding a scanning wand still for each such frame, and controllably moving the wand only between frames, is extremely challenging or impossible for a human operator.

Figure 25:
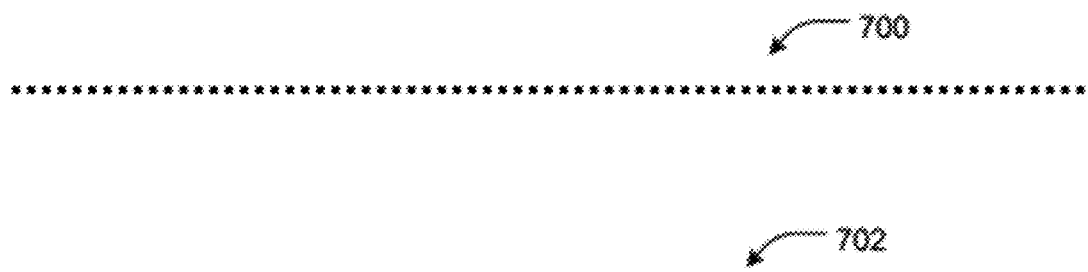
FIG. 25 illustrates a hypothetical conventional OCT system dense scan line segment consisting of individual sample points (pixels), as well as a hypothetical sparse scan line segment of an embodiment of the present invention.

Systems and methods of the present disclosure may solve these and other problems associated with the conventional OCT scanning technology as mentioned above. In particular, the OCT systems and methods herein may beneficially avoid unacceptable amounts of motion blur by traversing their respective scan patterns within a short period of time (e.g., typically completing an entire two-dimensional frame faster than a conventional raster scanner completes one raster line segment). In some cases, the shortened scanning time may be achieved by taking fewer A-scans per length of scan pattern than conventional OCT scanners. Compared to conventional scanners that typically conduct "dense" scans, systems and methods herein may be capable of conducting "sparse" scans without compromising imaging quality. As described in FIG. 20, conventional OCT systems sample individual points along the line 200, yielding individual pixels (not shown) along the line 200. FIG. 25 illustrates a hypothetical conventional OCT system dense scan line segment 700 consisting of individual sample points (pixels), as well as a hypothetical sparse scan line segment 702 of an embodiment of the present disclosure. Notice that the sample points of the line segment 700 are much more densely positioned along the line than the sample points along the line segment 702, although the specific ratio of sample spacings shown in FIG. 25 is merely for illustration.

Figure 26:
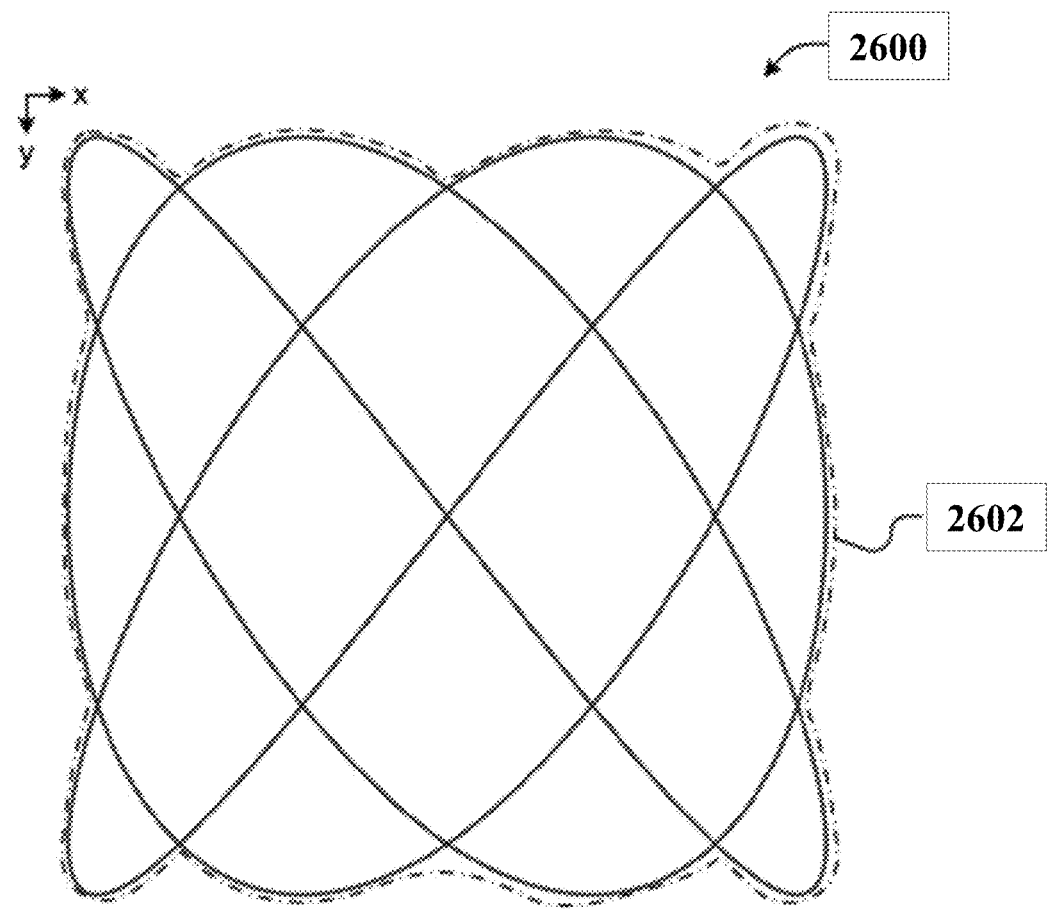
FIG. 26 illustrates an exemplary Lissajous figure used by embodiments of the present invention.

Some embodiments of the present disclosure utilize curved scan patterns, such as Lissajous figures or spirals. FIG. 26 illustrates an exemplary Lissajous FIG. 2600. The Lissajous figure can be the same as the Lissajous scanning path as described above.

Figure 9A:
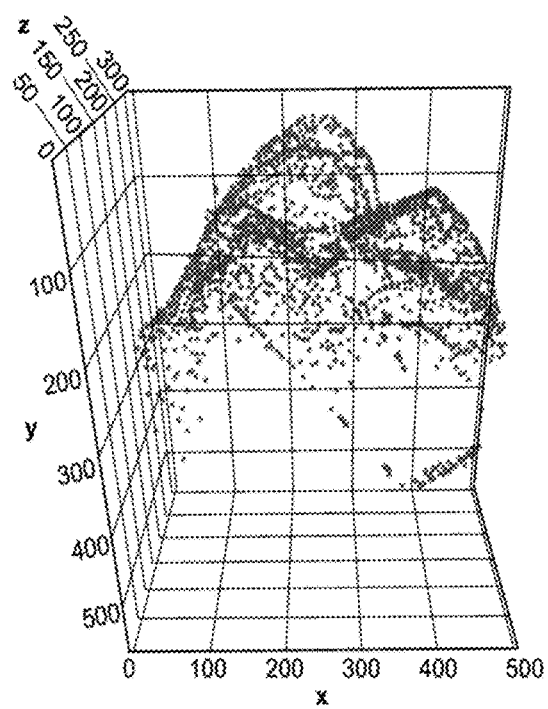
FIGS. 9A and 9B depict a combination of multiple scans; according to some embodiments.
Figure 9B:
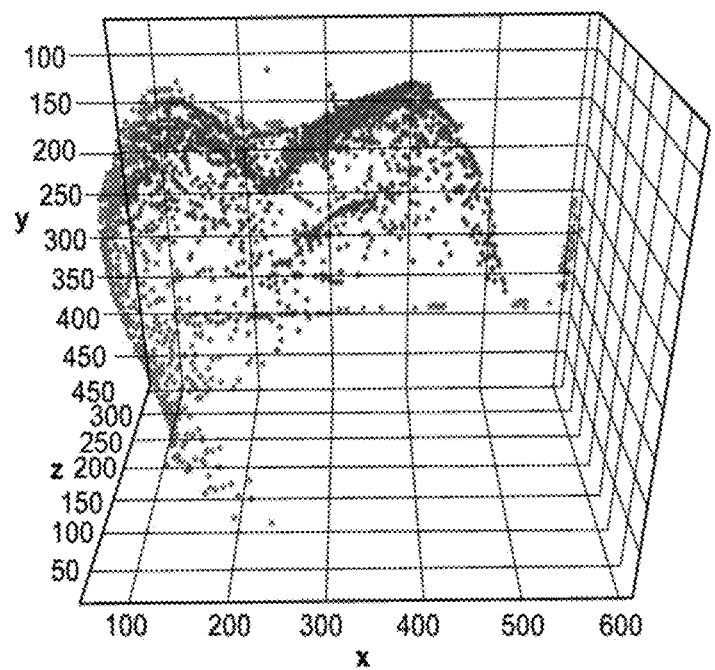

As shown schematically in FIG. 9, a tomography system 900 according to an embodiment of the present invention includes an OCT system 902 with an optical detector 903, a probe housing 904 of a scanning wand, and a movable mirror system 906 disposed within the housing. The mirror system 906 is configured to redirect, such as by reflecting, a portion of a sample arm 908 of the OCT system 902. A redirected portion 910 of the sample arm 908 extends outside the probe housing 904, into free space 912, via a window 914 in the probe housing 904. A controller 916 drives a motor 918 to repeatedly alter orientation of the mirror system 906 about two different axes (exemplified by axes at 920 and 922) to thereby repeatedly scan a surface 924 of an anatomic item under test 926 with light of the sample arm 908 along a trajectory 928 according to a deterministic smooth two dimensional scan pattern, exemplified by Lissajous pattern 930 shown in an Insert of the drawing. If the motor 918 oscillates the mirror system 906 about the two orthogonal axes 920 and 922 according to respective sine wave signals, a suitable Lissajous pattern can be achieved, based on relative frequencies and phases of the sine wave signals. Other exemplary Lissajous figures are shown in FIG. 10. As noted, other scan patterns may be used.

Returning momentarily to FIG. 26, a dashed line 2602 indicates an elastic bounding shape around the Lissajous FIG. 2600. As used herein, the term two-dimensional scan area outer boundary means a single closed loop elastic bounding shape tightly fitted to enclose an entire scan pattern, as exemplified by the dashed line 2602, and as viewed down an axis 932 (FIG. 27) of the sample arm 908, toward the item 926, i.e., as projected onto the surface 924 of the item 926. A locus of points on the anatomic item 926 that is illuminated by the sample arm 908 during a scan may have a shape distorted from the scan pattern, as viewed from a perspective other than from the window 914, due to topography of the surface 924.

Figure 29:
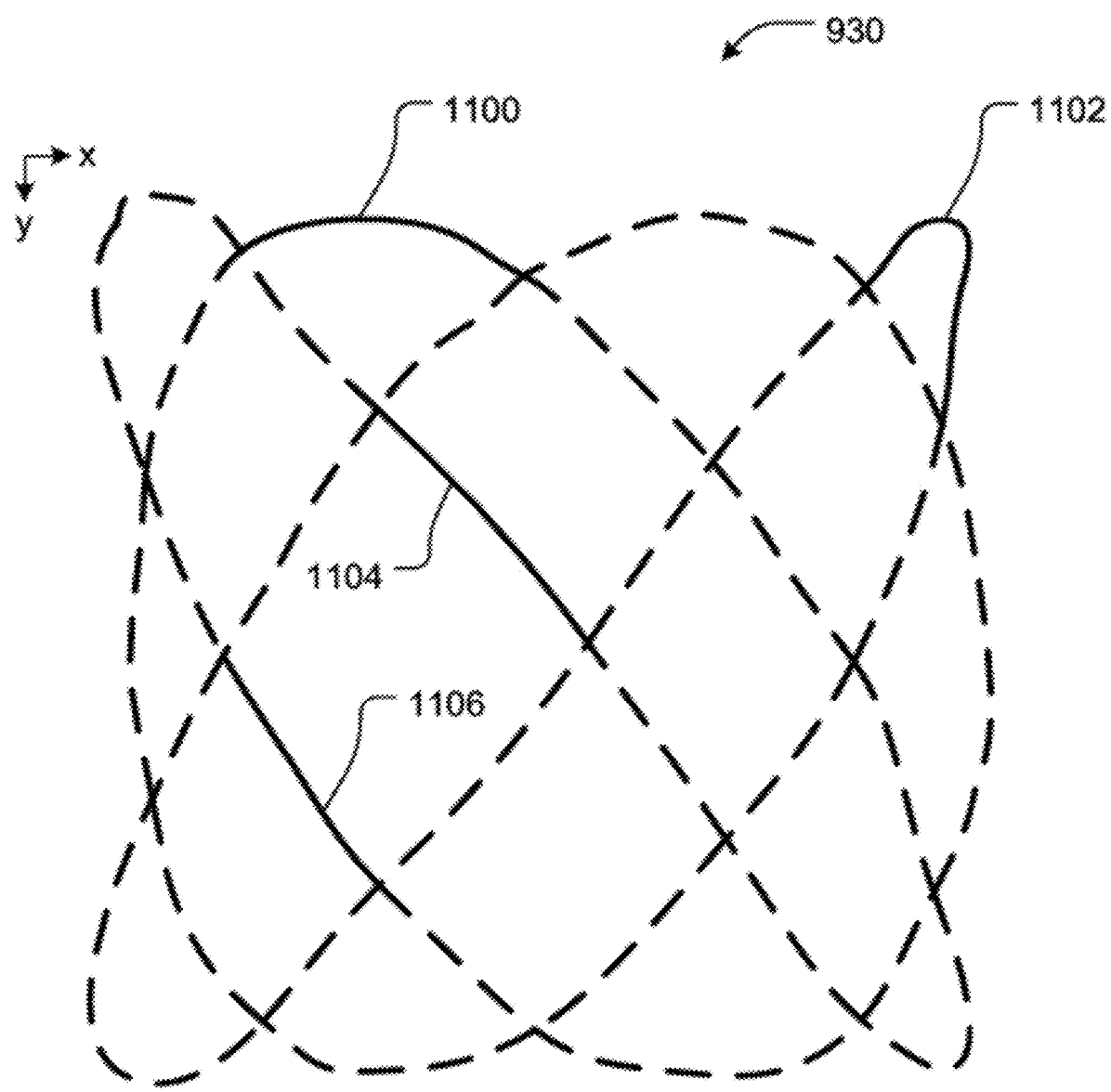
FIG. 29 shows the Lissajous figure of FIG. 9, largely in dashed line, to illustrate a concept of line segments, in relation to embodiments of the present invention.

Although, in each frame, the tomography system 900 of FIG. 9 scans portions of the item under test 926 within the two-dimensional scan area outer boundary, each frame includes samples from only a subset of the area of the two-dimensional scan area outer boundary. Specifically, each frame includes samples taken along a line (typically a curved and possibly self-crossing line, such as the Lissajous FIG. 930) that corresponds to the trajectory 928 of the sample arm light beam. Consequently, portions of the item 926 remain unsampled during each frame. For example, regions 934 and 936 (see FIG. 27 Insert) are unsampled by the Lissajous FIG. 930. The trajectory 928, particularly a complex trajectory, such as a Lissajous FIG. 930, can be considered to consist of a plurality of not-necessarily-straight line segments, as exemplified in FIG. 29. FIG. 29 shows the Lissajous FIG. 930, largely in dashed line. However, example line segments 1100, 1102, 1104, and 1106 are shown in solid line, for clarity. These line segments can be any length. The line segments need not necessarily begin and end at intersections with other lines or line segments of the trajectory.

Each traversal of the scan pattern defines a plurality of gaps between respective line segments of the trajectory. As noted, these gaps, exemplified by regions 934 and 936, are unilluminated by the light of the sample arm 908 during the traversal.

Figure 27:
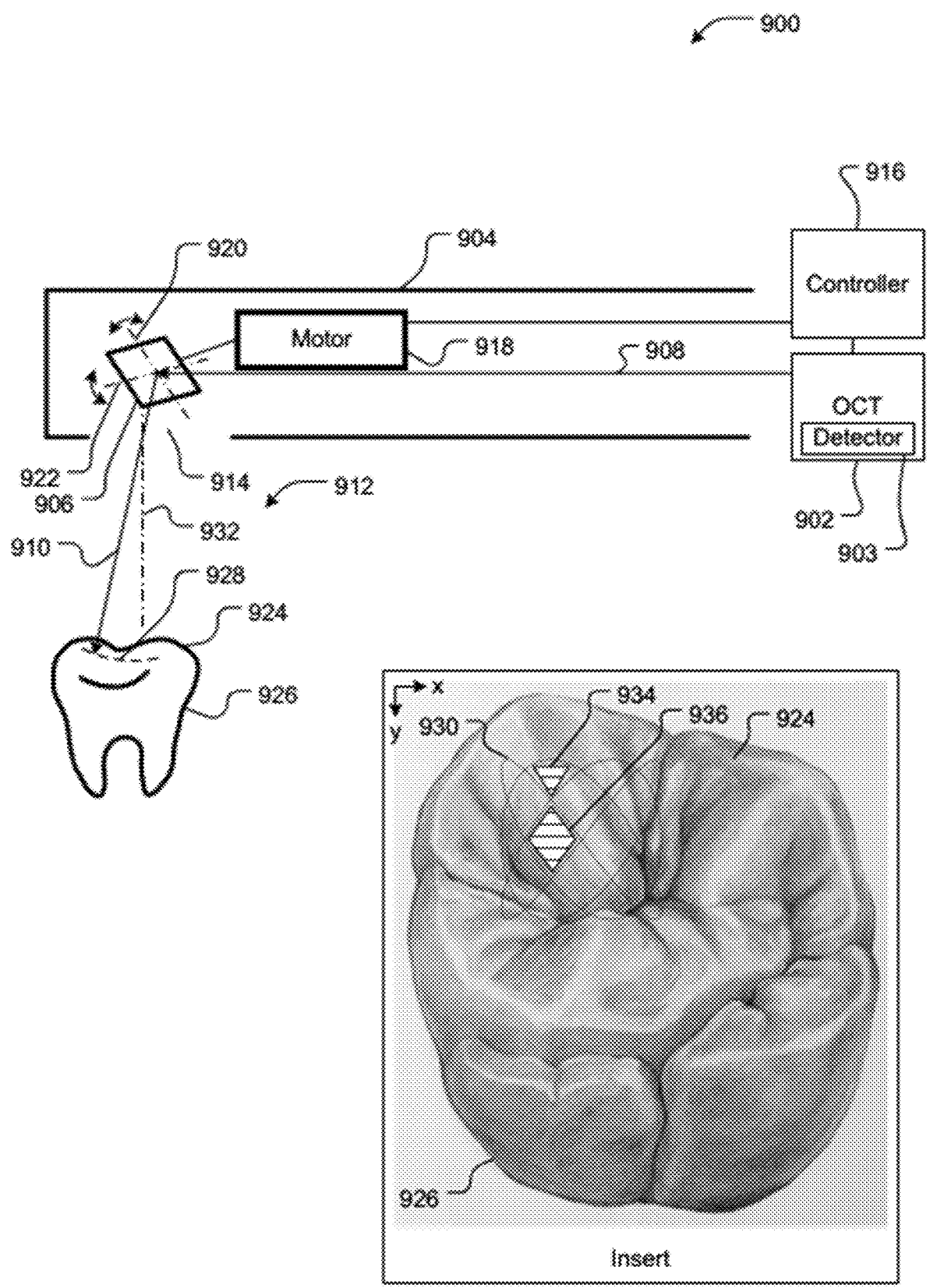
FIG. 27 is a schematic block diagram of a tomography system, according to embodiments of the present invention. An Insert in FIG. 9 illustrates an aspect of using the tomography system of FIG. 9.
Figure 28:
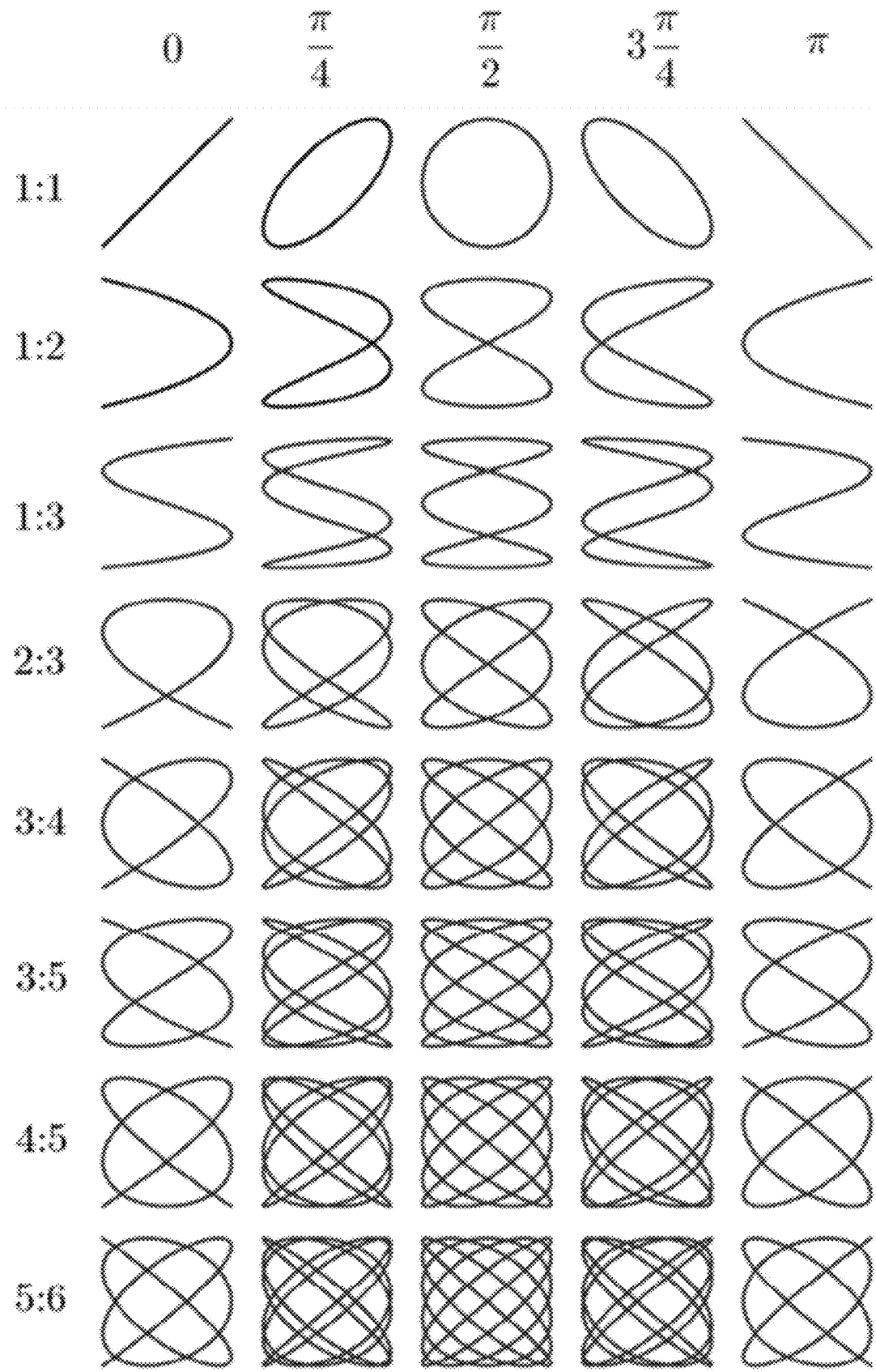
FIG. 28 illustrates other exemplary Lissajous figures that may be used by embodiments of the present invention.
Figure 30:
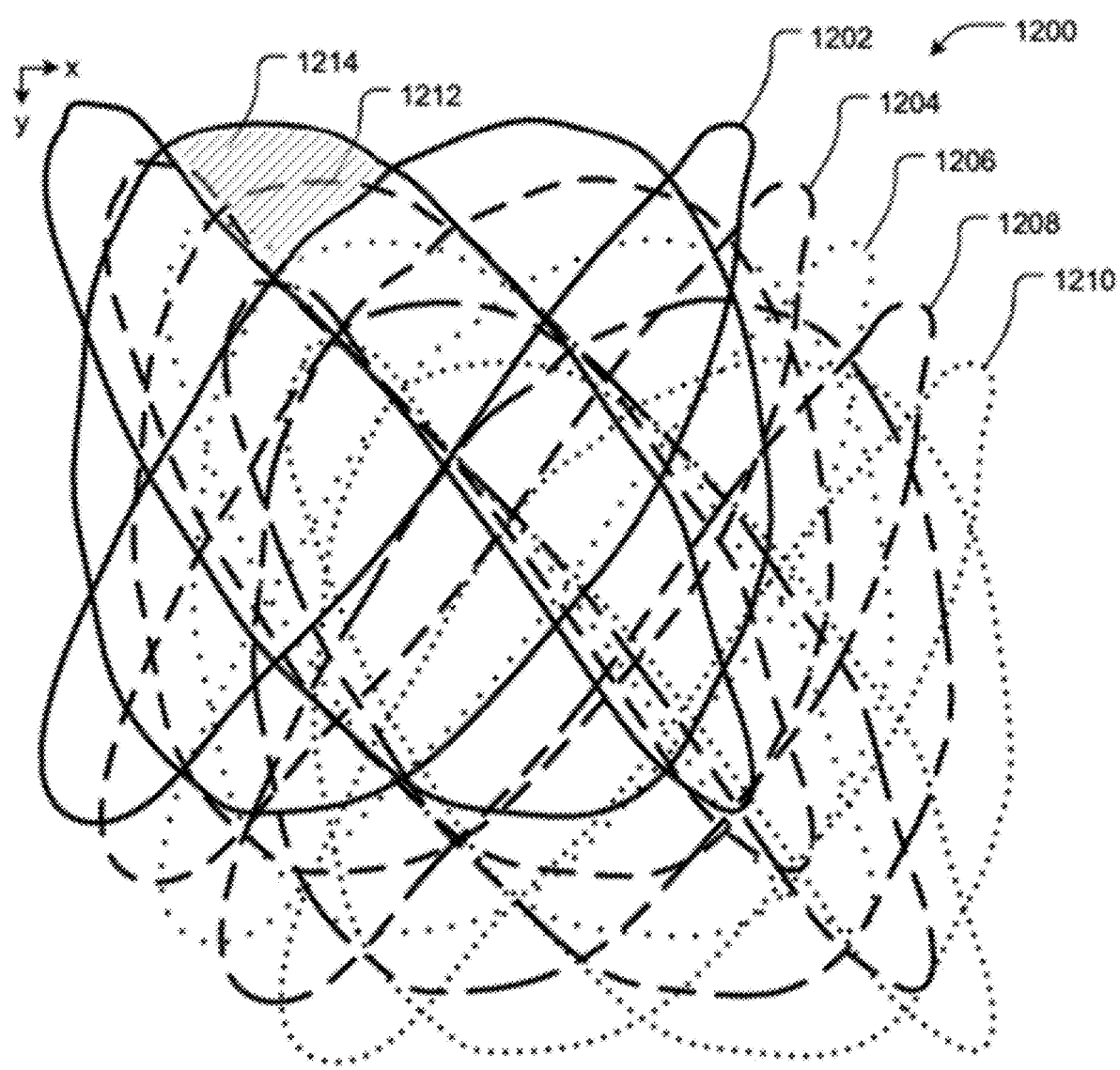
FIG. 30 illustrates a plurality of partially overlapping scan patterns, according to embodiments of the present invention.
Figure 31:
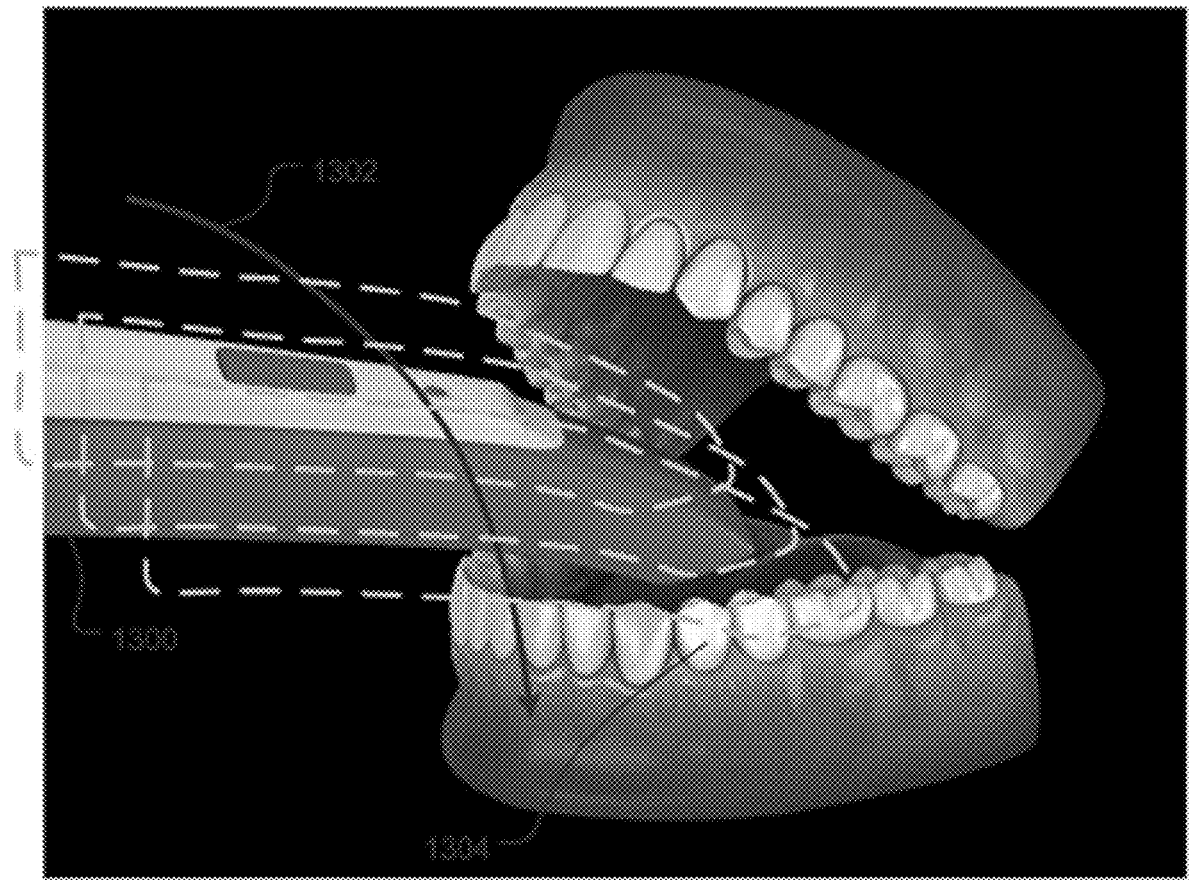
FIG. 31 illustrates use of an embodiment of the present invention and, in particular, translating a scanning wand in space along a path proximate an anatomical item under test.

To compensate for the sparsity of the sample points along their respective scan line segments discussed with respect to FIG. 25, and for the gaps between respective line segments of the trajectory discussed with respect to FIG. 27, embodiments of the present disclosure acquire and combine several partially overlapping frames for each imaging session, as schematically illustrated in FIG. 30. For simplicity of explanation, the Lissajous figures of FIGS. 26, 27, and 29 are used as the scan pattern. However, other scan patterns can be used, as discussed in more detail herein. Each such frame is acquired from a different point of view, relative to the item under test, as exemplified in FIG. 31. These view points result from a human operator or machine translating a scanning wand 1300 in space along a path 1302 proximate the anatomical item under test 1304, such as a tooth in a live patient. Thus, embodiments of the present invention take advantage of movement of the scanning wand 1300, rather than attempt to suppress the movement, as in the prior art.

FIG. 30 illustrates an exemplary plurality 1200 of successive traversals of the scan pattern 930 (FIG. 27), including a first traversal 1202, a second traversal 1204, a third traversal 1206, a fourth traversal 1208, and a fifth traversal 1210. For clarity of the drawing, each traversal 1202-1210 is shown in a different line dash type. Although five traversals 1202-1210 are shown, an imaging session can consist of any number of traversals. As noted, respective scans are performed from different locations along the path 1303 (FIG. 31) of the scanning wand 1300. In the example shown in FIG. 30, each successive scan has an upper-left corner at a progressively larger x and y coordinate than its preceding scan. Each scan has a respective scan area outer boundary (not shown in FIG. 30) that partially overlaps a scan area outer boundary of at least one other such scan. Successive traversals of the scan pattern illuminate respective portions of at least some of the gaps defined by at least one other such traversal of the scan pattern. For example, the second traversal 1204, such as a portion of the second traversal indicated at 1212, illuminates a portion of a gap, indicated by hash marks 1214, defined by the first traversal 1202.

For each traversal, the controller 916 (FIG. 27) receives pixel image data from the optical detector 903, about the respective portion of the surface 924 of the anatomic item 926. The pixel image data of each traversal 1202-1210 (FIG. 30) contains a first number of pixels. However, successive traversals 1202-1210 "fill in" portions of, i.e., interlace with, some of the gaps in other of the traversals 1202, 1210. Thus, for a plurality of successive traversals, the controller 916 stitches together the pixel image data of the plurality of successive traversals 1202-1210 to thereby generate a stitched surface image having a number of pixels greater than the first number of pixels. Any conventional two-dimensional or three-dimensional point cloud registration and stitching methodology may be used.

Although the controller 916 generates a stitched surface image having a greater number of pixels than each of the individual traversals 1202-1210, the controller does not rely on interpolation to achieve this increase in pixel density. In contrast, compressive sensing schemes, such as those described in U.S. Pat. No. 11,497,402, use random or pseudo-random samples to reconstruct a surface. Using compressive sensing-type data acquisition, it is possible to reconstruct a broad class of sparse signals, containing a small number of dominant components in some domain, by employing a sub-Nyquist sampling rate. Instead of applying uniformly-spaced signal measurements, as in Nyquist-based sampling, compressive sensing theory demonstrates that several types of uniformly-random sampling protocols yield successful reconstructions with high probability.

U.S. Pat. No. 11,497,402 discloses randomized sampling OCT in two spatial dimensions, x and y. X scan positions are generated from a first pseudo-random sequence, and y scan positions are determined using a second pseudo-random sequence. A two-dimensional sampling grid is determined by interleaving the x and y sequences. Sampling tuples ($x_i$, $y_i$) are created from $x_i$ components of the x random sampling sequence $x=\{x_1, x_2, \ldots, x_w\}$ and $y_i$ components of the y random sampling sequence $y=\{y_1, y_2, \ldots, y_D\}$. This forms a randomized or pseudo-randomized spacing arrangement that helps reduce the number of samples required to be obtained for generating an OCT reconstruction.

On the other hand, embodiments of the present invention do not rely on randomized or pseudo-randomized spacing arrangement. As used herein, the term deterministic means not random and not pseudo-random. As noted, the controller 916 drives the motor 918 to repeatedly alter orientation of the mirror system 906 about two different axes to thereby repeatedly scan the surface 924 of the anatomic item under test 926 with light of the sample arm 908 along a trajectory 928 according to a deterministic scan pattern.

Some embodiments use the stitched surface image as a map to stitch together voxel subsurface data from the optical detector 903. As used herein, pixel means a picture element of a one- or two-dimensional image or a voxel (a volume element of a three-dimensional image). For each traversal, the controller 916 receives voxel subsurface data from the optical detector 903 about a respective subsurface portion of the anatomic item 926. The voxel subsurface data of each traversal contain a second number of voxels. As in the surface stitching case, successive traversals 1202, 1210 "fill in" (interlace) portions of some of the gaps in other of the traversals 1202-1210. Thus, for the plurality of successive traversals, the controller 916 stitches together the voxel subsurface data of the plurality of successive traversals to thereby generate a stitched subsurface three-dimensional volume image having a number of voxels greater than the second number of voxels.

In some embodiments, the sample arm of the OCT 902 has a wavelength of about 1310 nm, the A-scan rate is about 200 kHz, the OCT lateral beam spot size is about 35 μm, and the imaging range is about 16 mm. The field of view is about 8 mm by 8 mm.

Applicability to Raster Scans

Although smooth scan patterns are described herein, some embodiments employ raster scans and partially overlap (interlace) two-dimensional scan area outer boundaries, as described with respect to FIG. 30. Raster lines of successive frames interleave to illuminate at least portions of gaps defined by previous raster frames.

Slight Discontinuity in Scan Pattern

Although smooth scan patterns are described herein, in some embodiments, the controller is configured to drive the motor to repeatedly alter orientation of the mirror system about two different axes to thereby repeatedly scan the surface of the anatomic item with light of the sample arm along a trajectory according to a scan pattern that is smooth along at least 80% of the trajectory. For example, the scan pattern can be a spiral, with a retrace from/to the center to/from the outer edge.

Such a system can be implemented with two galvo mirrors, or one mirror that can be reoriented in two dimensions, such as a MEMS mirror.

Motion Detection Using Intersecting Traversals of Line Segments

A place where one line segment of a scan pattern crosses (intersects) with another line segment of the same traversal of the scan pattern can provide information to quantify motion of the housing 904 (FIG. 27) between two times. For example, an intersection identified at 1216 (FIG. 30) of two line segments 1218 and 1220 of traversal 1204 can be used to quantify motion of the housing 904 between (a) a time the sample arm 908 light beam traversed line segment 1218 in the vicinity of the intersection 1216 and (b) a time the sample arm 908 light beam traversed the other line segment 1220 in the vicinity of the intersection 1216.

Ideally, if the housing 904 has not moved between times (a) and (b), the sample arm 908 light beam should interrogate the same or very similar regions of the item under test 926 in the vicinity of the intersection 1216. If, however, the controller 916 detects a significant difference, ex. greater than a predetermined amount, between portions of the item under test 926 that are interrogated by the light beam at times (a) and (b), the controller 916 may conclude that the point of view of the housing 904 has changed significantly between times (a) and (b). Optionally, the controller 916 may discard the current frame, on an assumption that the frame suffers from excessive motion blur.

Alternatively, the controller 916 may estimate an amount of change in the field of view by analyzing differences in the portions of the item under test 926 that were interrogated by the light beam at times (a) and (b). For example, based on information about a characteristic, such as reflectivity, density, or color, of the portions of the item under test 926 interrogated at times (a) and (b) and an expected spatial gradient in that characteristic of the item under test 926, the controller 916 may estimate a spatial distance between where the two samples were interrogated and, therefore, estimate an amount or rate of translation of the housing 904. The expected spatial gradient in the characteristic may be a pre-programmed assumption, or it may be a user-entered value, or the controller 916 may automatically estimate the gradient based on other samples of the item under test 926.

Definitions

As used herein, the following term shall have the following meanings, unless context indicates otherwise.

"Continually" means continuously or repeatedly, although not necessarily in perpetuity. The term continually encompasses periodically and occasionally. Continually generating a signal means generating a continuously varying signal over time or generating a series of (more than one) discrete signals over time. Continually generating a value, such as an error value, means generating a continuously varying value, such as an analog value represented by a continuously varying voltage, or generating a series of (more than one) discrete values over time, such as a series of digital or analog values.

While the invention is described through the above-described exemplary embodiments, modifications to, and variations of, the illustrated embodiments may be made without departing from the inventive concepts disclosed herein. For example, although specific parameter values, such as materials and dimensions, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

As used herein, including in the claims, an element described as being configured to perform an operation "or" another operation is met by an element that is configured to perform only one of the two operations. That is, the element need not be configured to operate in one mode in which the element performs one of the operations, and in another mode in which the element performs the other operation. The element may, however, but need not, be configured to perform more than one of the operations.

Although aspects of embodiments may be described with reference to flowcharts and/or block diagrams, functions, operations, decisions, etc. of all or a portion of each block, or a combination of blocks, may be combined, separated into separate operations or performed in other orders. References to a "module," "operation," "step" and similar terms are for convenience and not intended to limit their implementation. All or a portion of each block, module, operation, step or combination thereof may be implemented as computer program instructions (such as software), hardware (such as combinatorial logic, Application Specific Integrated Circuits (ASICs), Field Programmable Gate Arrays (FPGAs), processor or other hardware), firmware or combinations thereof.

The controller 916, etc. or portions thereof may be implemented by one or more suitable processors executing, or controlled by, instructions stored in a memory. Each processor may be a general-purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), non volatile memory (NVM), non-volatile random-access memory (NVRAM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, database schemas and the like, systems may be embodied using a variety of data structures, schemas, etc.

Disclosed aspects, or portions thereof, may be combined in ways not listed herein and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective elements, such as mirrors or traversals, from one another and are not intended to indicate any particular order or total number of mirrors or traversals in any particular embodiment. Thus, for example, a given embodiment may include only a second mirror and a third traversal.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A tomography system comprising:
  a probe housing defining a window and configured to be oriented and reoriented, and moved along a path proximate an anatomical item in a live patient, the anatomical item having a surface;
  an optical coherence tomography system comprising an optical detector and a light source configured to produce a sample, wherein, during operation, a portion of the sample arm extends outside the probe housing, in free space, via the window, in a direction that depends on orientation and position of the probe housing;
  a moveable mirror system disposed within the probe housing and configured to redirect the sample arm;
  a motor disposed within the probe housing and coupled to the mirror system; and a controller configured to automatically:
drive the motor to repeatedly alter orientation of the mirror system about two different axes to thereby repeatedly scan the surface of the anatomic item with light of the sample arm along a trajectory according to a deterministic two-dimensional scan pattern, such that:
each traversal of the scan pattern defines a respective two-dimensional scan area on a respective portion of the surface of the anatomic item, thereby collectively defining a plurality of scan areas; and
each traversal of the scan pattern yields a respective sparse data frame having a respective first pixel density captured from within the respective two-dimensional scan area, while the probe housing was at a respective orientation and position, thereby collectively yielding a plurality of sparse data frames as the probe housing is oriented, reoriented, and moved along the path;
receive pixel data from the optical detector for the plurality of sparse data frames, wherein at least some frames of the plurality of sparse data frames were captured from different respective probe housing orientations and/or positions, and wherein at least some frame pairs of the plurality of sparse data frames have partially overlapping respective scan areas; and
generate a dense surface image data frame by combining pixel data of at least partially overlapping frames of the plurality of sparse data frames, wherein the dense data frame has a second pixel density greater than the first pixels density.

2. A tomography system according to claim 1, wherein the controller is configured to analyze image features of the plurality of sparse data frames to thereby estimate respective displacements of ones of the plurality of scan areas from other ones of the plurality of scan areas.

3. A tomography system according to claim 1, wherein the scan pattern comprises a Lissajous figure.

4. A tomography system according to claim 1, wherein the scan pattern is anisotropic.

5. A tomography system according to claim 1, wherein the controller is configured to automatically:
for each traversal, receive voxel subsurface data from the optical detector, about a respective subsurface portion of the anatomic item, such that each traversal yields a respective sparse voxel volume having a respective first voxel density, thereby collectively yielding a plurality of sparse voxel volumes; and
generate a dense subsurface three-dimensional volume image by combining voxel data of a plurality of at least partially overlapping volumes of the plurality of sparse voxel volumes, wherein the dense subsurface three-dimensional volume image has a second voxels density greater than the first voxels density.

6. A tomography system according to claim 5, wherein the controller is configured to automatically:
use the pixel data to detect an enamel/air boundary of the anatomical item;
estimate an amount of refraction of the light at the enamel/air boundary based on a difference between a refractive index of enamel and a refractive index of air; and
alter coordinates of the voxel subsurface data to at least partially compensate for the refraction of the light at the enamel/air boundary.

7. A tomography system according to claim 5, wherein the controller is configured to automatically:
use the pixel data and/or the voxel subsurface data to detect an enamel surface of the anatomical item;
use the voxel subsurface data to detect an enamel/dentin boundary within the anatomical item;
estimate a thickness of the enamel between the enamel surface and the enamel/dentin boundary;
estimate an amount of refraction of the light within the enamel based on (a) the thickness of the enamel and (b) a predetermined index of refraction of enamel; and
alter coordinates of the voxel subsurface data to at least partially compensate for the refraction of the light within the enamel.

8. A tomography system according to claim 1, wherein:
the mirror system has a resonant frequency; and
the controller is configured to drive the motor to repeatedly alter orientation of the mirror system at a frequency within 50% of the resonant frequency.

9. A tomography system according to claim 8, wherein the controller is configured to drive the motor to repeatedly alter orientation of the mirror system at a frequency within 30% of resonant the frequency.

10. A tomography system according to claim 8, wherein the controller is configured to drive the motor to repeatedly alter orientation of the mirror system at a frequency within 20% of resonant the frequency.

11. A tomography system according to claim 1, wherein the two-dimensional scan pattern is smooth.

12. A tomography system according to claim 1, wherein the two-dimensional scan pattern comprises a raster.

13. A tomography system according to claim 1, wherein the two-dimensional scan pattern.

14. A tomography system according to claim 13, wherein the scan pattern comprises a spiral.

15. The tomography system of claim 1, wherein:
the mirror comprises a first mirror and a second mirror; and
the motor is configured to continually alter orientation of the first mirror along a first axis and to continually alter orientation of the second mirror along a second axis, different from the first axis.

16. The tomography system of claim 1, wherein collectively the mirror and the motor comprise a dual-axis micro-electro-mechanical system.

17. The tomography system of claim 1, further comprising:
a memory storing calibration data that characterizes per tomography system optical nonidealities; and wherein:
the controller is configured to alter data received from the optical detector to at least partially compensate for the optical nonidealities.

18. The tomography system of claim 17, wherein the optical nonidealities comprise at least one of: lens aberration, deformation of the mirror due to being driven by the motor, and optical misalignment.

19. The tomography system of claim 1, wherein the controller is configured to drive the motor to alter the orientation of the mirror system along the two axes to thereby repeatedly scan the item along a first closed-loop two-dimensional scan trajectory and a second closed-loop two-dimensional scan trajectory, wherein the first closed-loop two-dimensional scan trajectory provides more sample points than the second closed-loop two-dimensional scan trajectory.

20. The tomography system of claim 19, further comprising:
a motion detector mechanically coupled to the probe housing and configured to detect motion of the probe housing; and
the controller is configured to automatically:
detect when the probe housing motion is less than a predetermined value;
control the motor such that:
when the probe housing motion is less than the predetermined value, the motor alters the orientation of the mirror to scan the anatomical item along the first closed-loop two-dimensional scan trajectory; and
when the probe housing motion is not less than the predetermined value, the motor alters the orientation of the mirror to scan the anatomical item along the second closed-loop two-dimensional scan trajectory.

21. The tomography system of claim 1, further comprising a pulsed-to-continuous wave light buffer, comprising:
a laser configured to output a series of pulses, each pulse having a pulse width;
an N-way optical splitter coupled to an output of the laser, where N >1;
at least N−1 delay lines, a respective input of each delay line of the N−1 delay lines being coupled to a respective output of the N-way splitter; and
an N-way optical combiner; wherein:
a respective output of each delay line is coupled to a respective input of the N-way optical combiner; and
each delay line is configured to impart a delay equal to about a different integral multiple of the pulse width, plus a constant k (k >=0).

22. The tomography system of claim 21, wherein:
the laser is configured to output light according to a duty cycle (D); and $N=(1/D)-1.$ 23. The tomography system of claim 21, wherein:
the laser is configured to output light according to a duty cycle (D); and $N=1/D.$ 24. The tomography system of claim 21, further comprising:
a polarization detector optically coupled to an output of the N-way optical combiner; and
a polarization controller that is:
optically coupled between the laser and one input of the N-way optical combiner, communicatively coupled to the polarization detector, and
configured to adjust polarization of light passing therethrough to match polarization of light delivered to another input of the N-way optical combiner.

25. The tomography system of claim 1, wherein the controller is configured to automatically detect at least a portion of the surface of the anatomical item from the sparse data frame.

* * * * *

UNITED STATES PATENT AND TRADEMARK OFFICE
CERTIFICATE OF CORRECTION

PATENT NO. : 12,016,653 B2
APPLICATION NO. : 18/464014
DATED : June 25, 2024
INVENTOR(S) : Ciriello et al.

It is certified that error appears in the above-identified patent and that said Letters Patent is hereby corrected as shown below:

In the Claims

Column 42, In Claim 13, Lines 33-34, should read:
A tomography system according to claim 1, wherein the two-dimensional scan pattern is smooth along at least 80% of the trajectory.

Signed and Sealed this
Sixth Day of August, 2024

Katherine Kelly Vidal
*Director of the United States Patent and Trademark Office*